(12) United States Patent
Adams et al.

(10) Patent No.: US 9,011,466 B2
(45) Date of Patent: Apr. 21, 2015

(54) BI-DIRECTIONAL SUTURE PASSER

(75) Inventors: Ray Adams, Ansonia, CT (US); David T. Banks, West Chester, PA (US); Rudolf Bertagnoli, Straubing (DE); Joel Helfer, Cheshire, CT (US); Scott Larsen, West Chester, PA (US); Lawton Laurence, West Chester, PA (US); Adam Lehman, Northford, CT (US); Jamie Manos, West Chester, PA (US); Vincent Mata, Monroe, CT (US); Dominique Messerli, West Chester, PA (US); Tom Overes, Langendorf (CH); Wamis Singhatat, West Chester, PA (US); James Talbot, West Chester, PA (US); Ken Underhill, West Chester, PA (US); Daniel Vennard, West Chester, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 125 days.

(21) Appl. No.: 12/693,820

(22) Filed: Jan. 26, 2010

(65) Prior Publication Data
US 2011/0028998 A1 Feb. 3, 2011

Related U.S. Application Data

(60) Provisional application No. 61/147,251, filed on Jan. 26, 2009.

(51) Int. Cl.
*A61B 17/04* (2006.01)
*A61B 17/062* (2006.01)
*A61B 17/06* (2006.01)
*A61B 17/00* (2006.01)

(52) U.S. Cl.
CPC ......... *A61B 17/0482* (2013.01); *A61B 17/0469* (2013.01); *A61B 17/06066* (2013.01); *A61B 17/0625* (2013.01); *A61B 2017/00477* (2013.01); *A61B 2017/00867* (2013.01); *A61B 2017/0496* (2013.01)

(58) Field of Classification Search
USPC .......................................... 606/139, 144–150
See application file for complete search history.

(56) References Cited

U.S. PATENT DOCUMENTS

| | | | |
|---|---|---|---|
| 4,345,601 A | 8/1982 | Fukuda | |
| 5,336,229 A | 8/1994 | Noda | |
| 5,792,153 A * | 8/1998 | Swain et al. | 606/144 |
| 6,533,796 B1 | 3/2003 | Sauer et al. | |
| 6,551,330 B1 | 4/2003 | Bain et al. | |
| 6,991,635 B2 | 1/2006 | Takamoto et al. | |
| 6,997,931 B2 | 2/2006 | Sauer et al. | |
| 7,063,710 B2 | 6/2006 | Takamoto et al. | |
| 7,381,210 B2 | 6/2008 | Zarbatany et al. | |
| 7,407,505 B2 * | 8/2008 | Sauer et al. | 606/145 |
| 7,544,199 B2 | 6/2009 | Bain et al. | |
| 7,744,609 B2 | 6/2010 | Allen et al. | |
| 8,313,496 B2 | 11/2012 | Sauer et al. | |
| 2005/0154402 A1 | 7/2005 | Sauer | |

FOREIGN PATENT DOCUMENTS

| | | |
|---|---|---|
| EP | 1354558 | 10/2003 |
| WO | WO 01/01868 | 1/2001 |
| WO | WO 2008/045376 | 4/2008 |

* cited by examiner

*Primary Examiner* — Gregory Anderson
*Assistant Examiner* — Christina Lauer
(74) *Attorney, Agent, or Firm* — Baker & Hostetler LLP

(57) ABSTRACT

A bi-directional suture passing instrument configured to approach soft tissues perpendicularly, enables safer and more efficient surgical repairs and minimally invasive techniques to be employed, useful in areas such as annulus repair, meniscal repair, shoulder arthroscopy, hernia repair, laparoscopic repair, and wound closure.

28 Claims, 78 Drawing Sheets

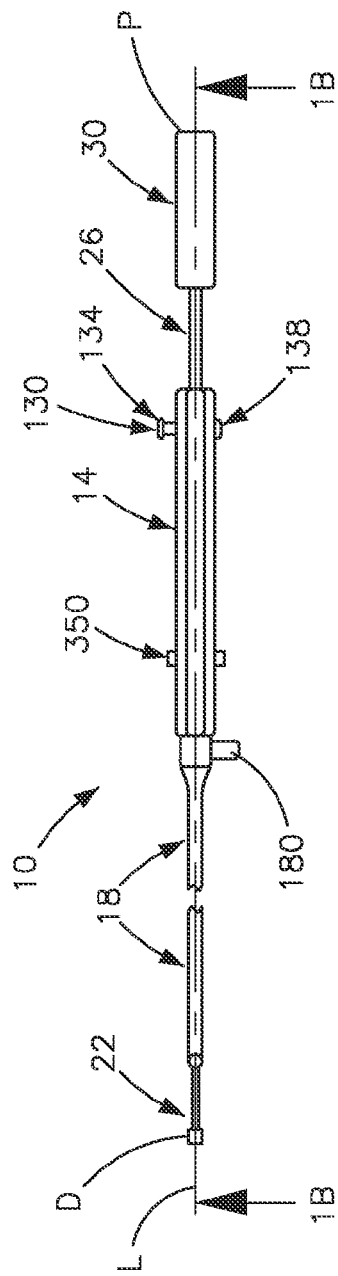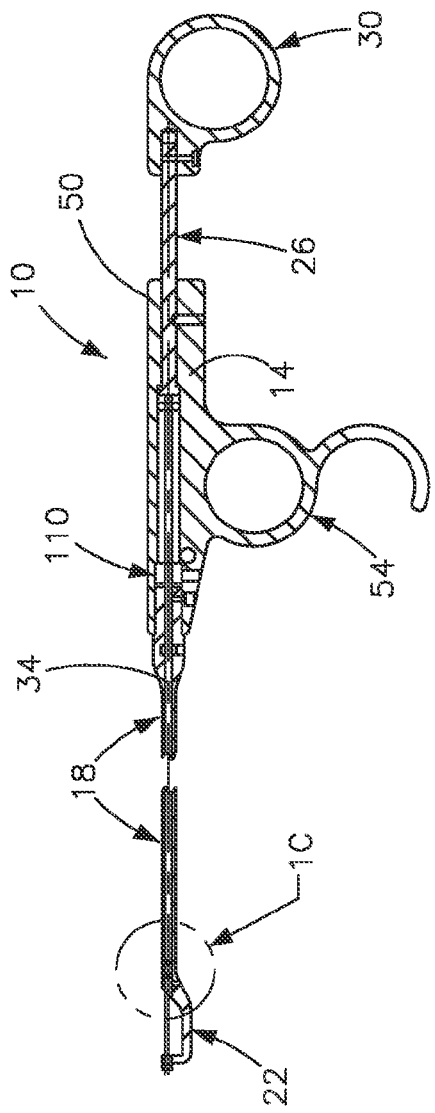

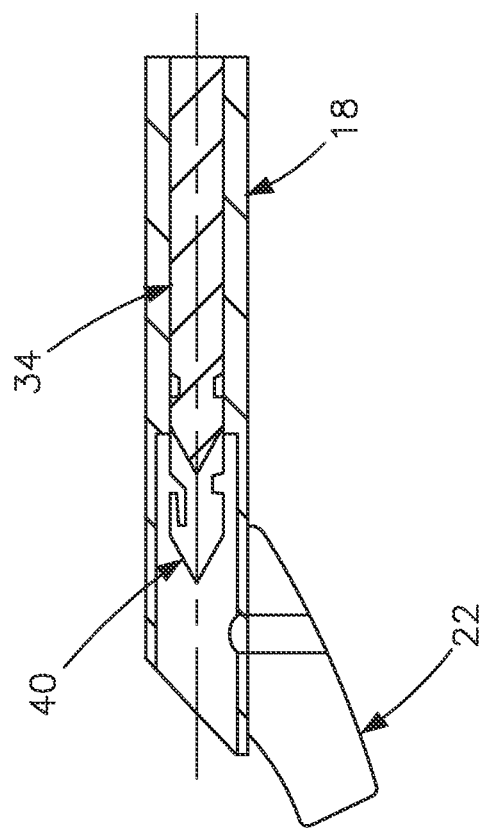

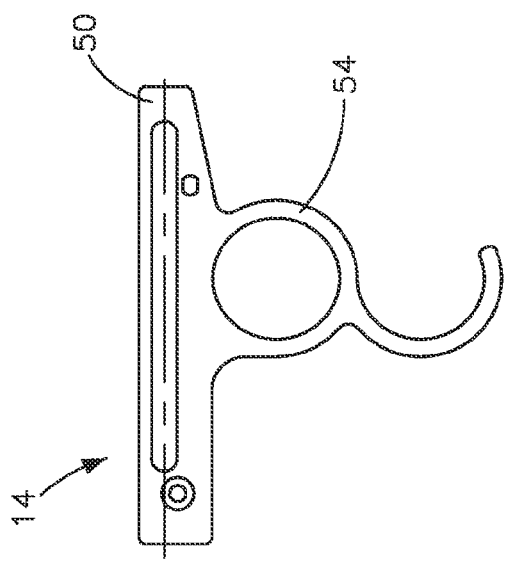
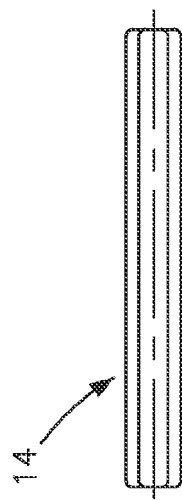
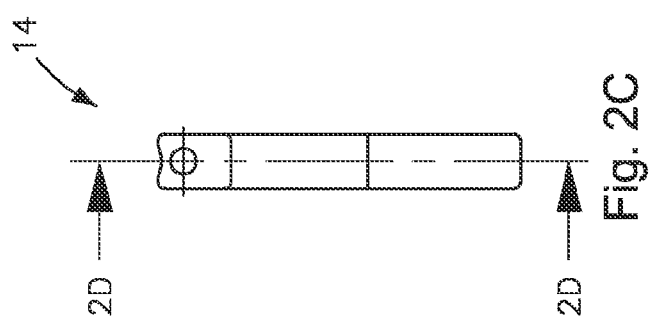

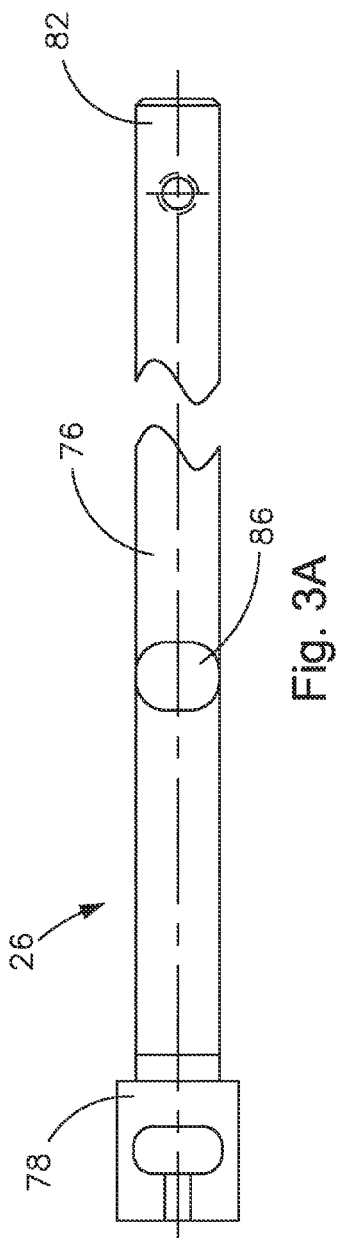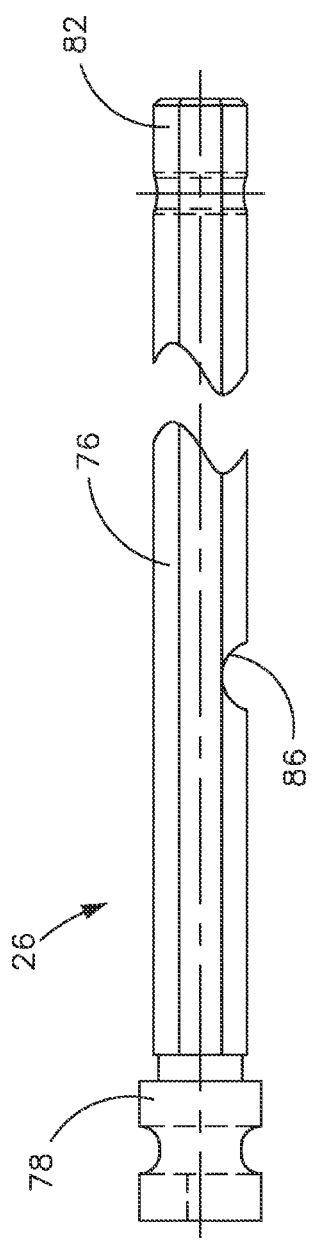

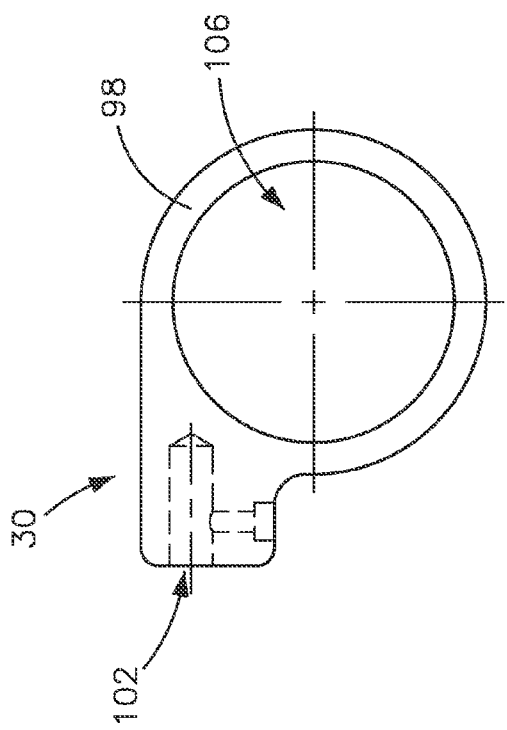
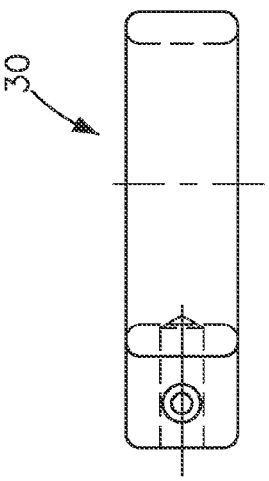
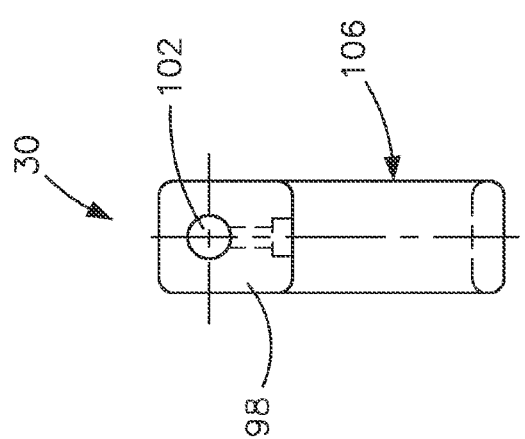

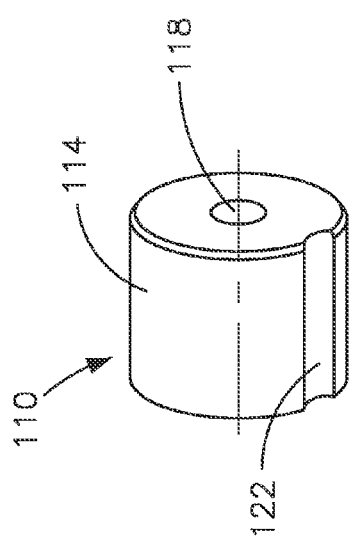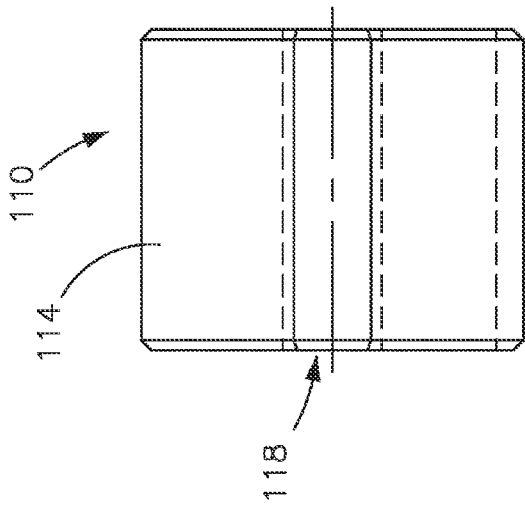

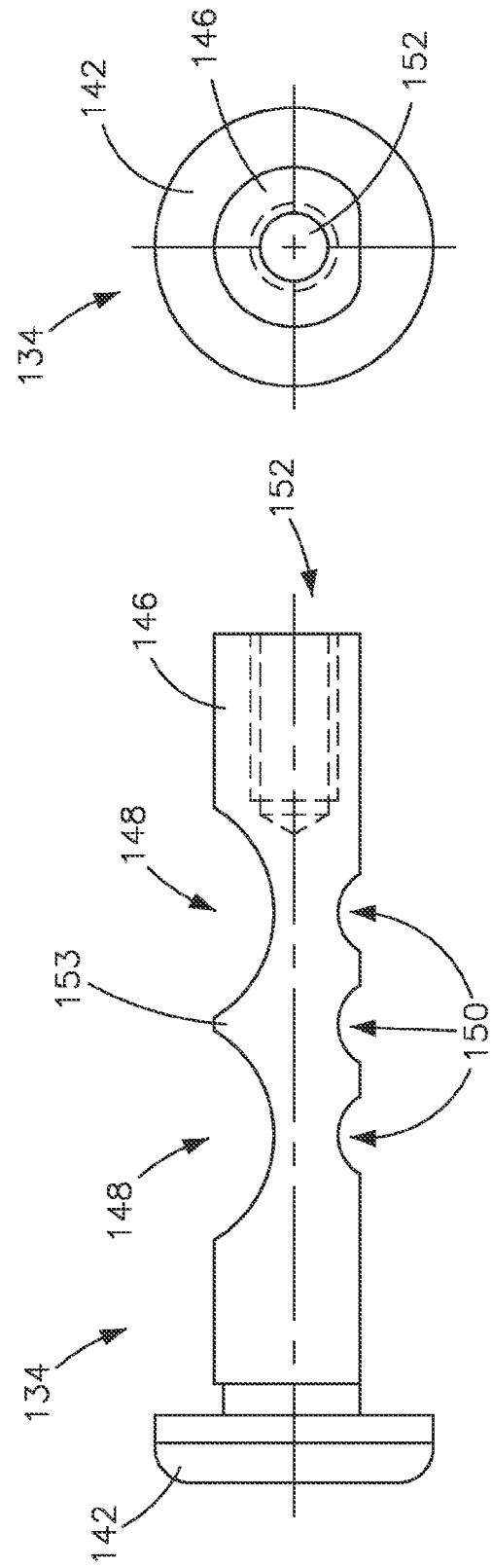

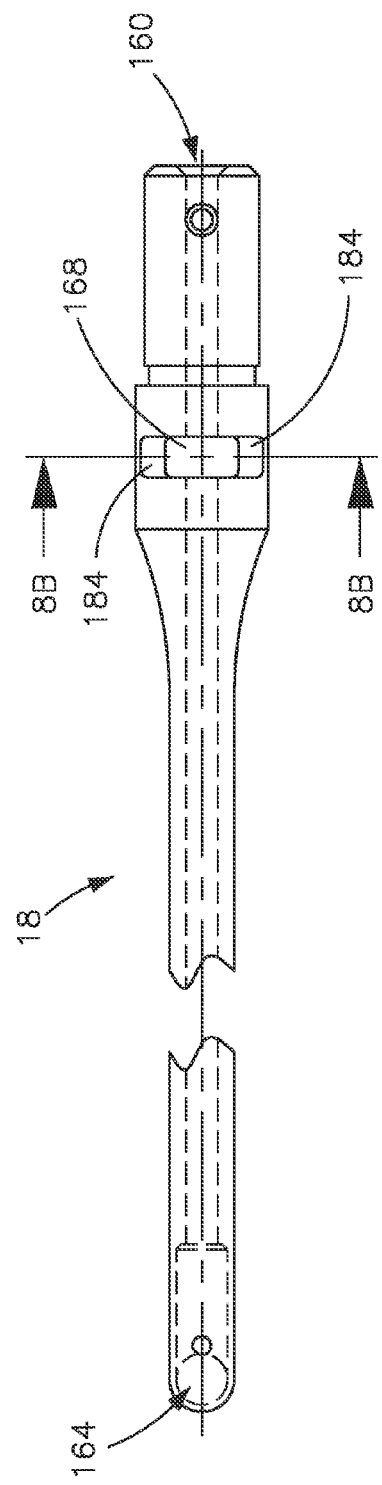
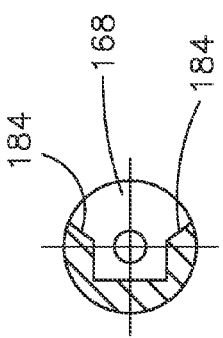
Fig. 8A
Fig. 8B

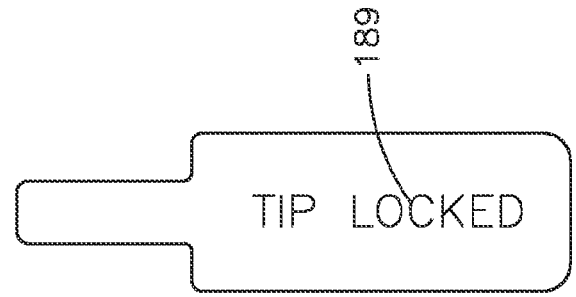
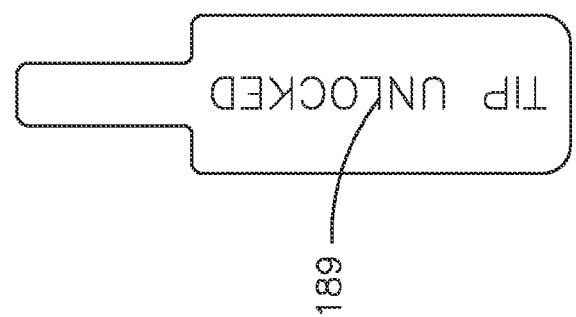
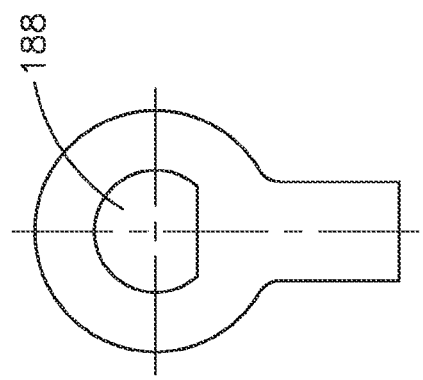
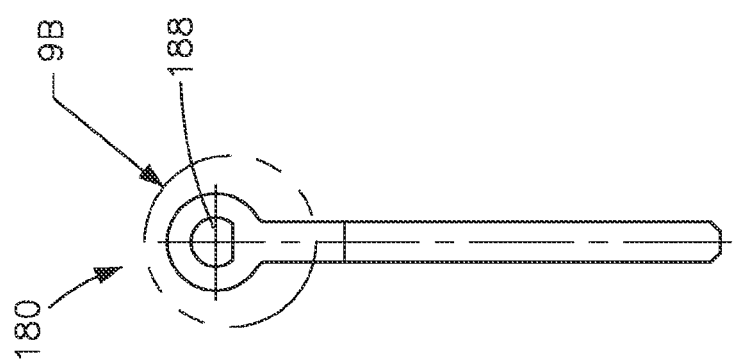

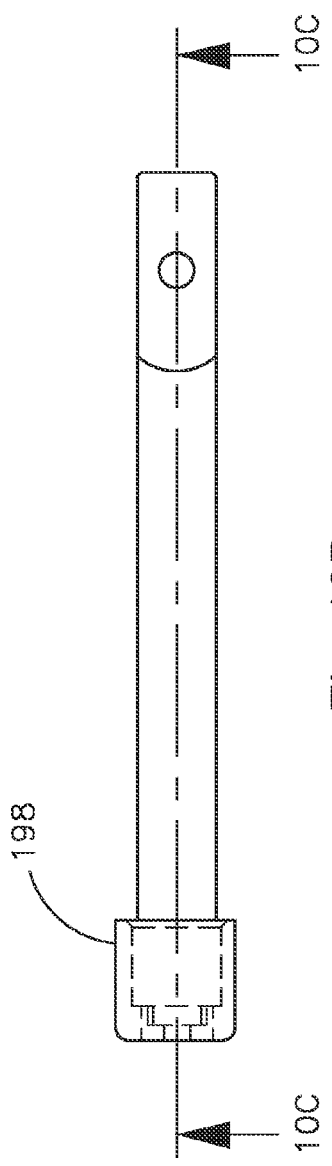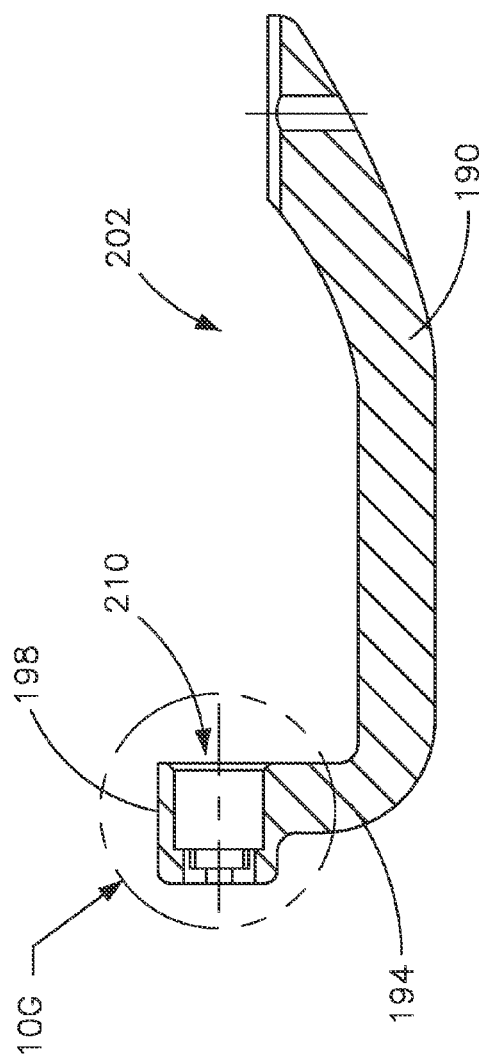

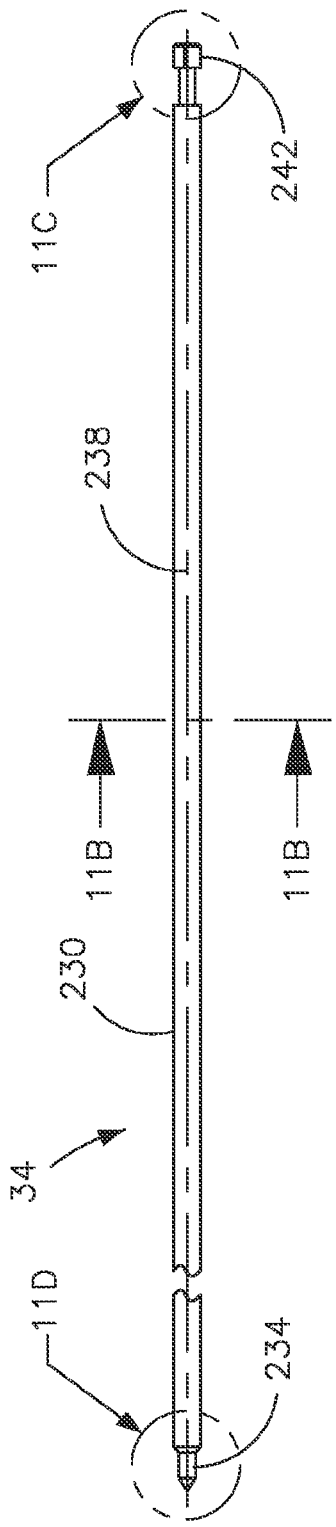
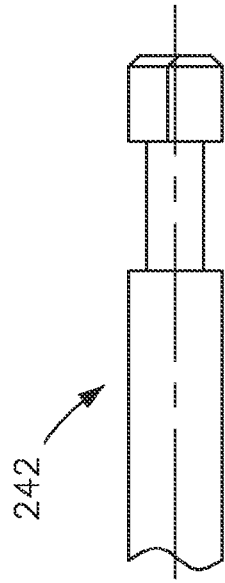
Fig. 11C
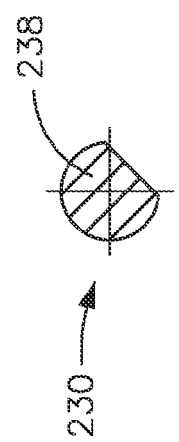
Fig. 11B
Fig. 11A

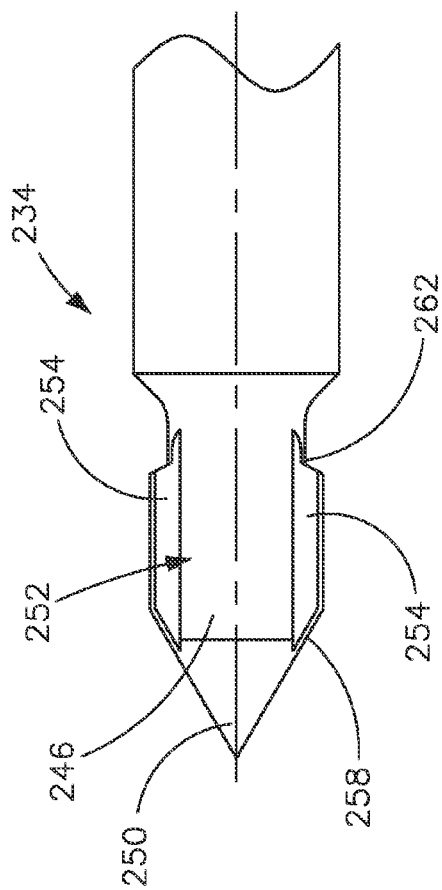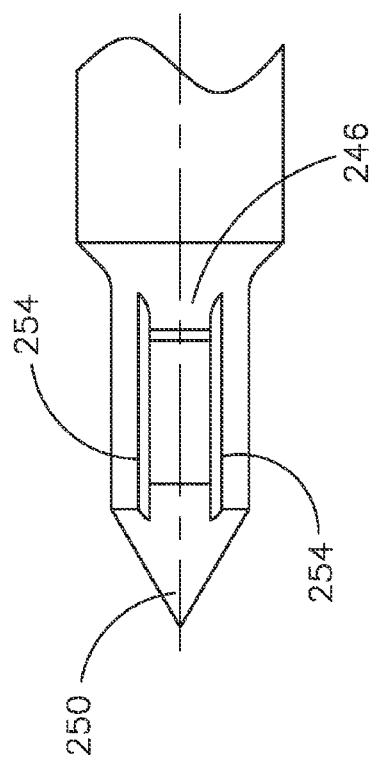
Fig. 11D
Fig. 11E

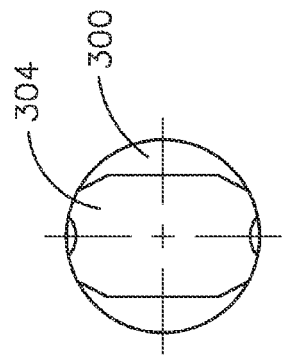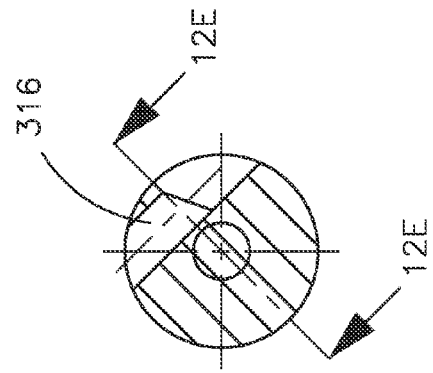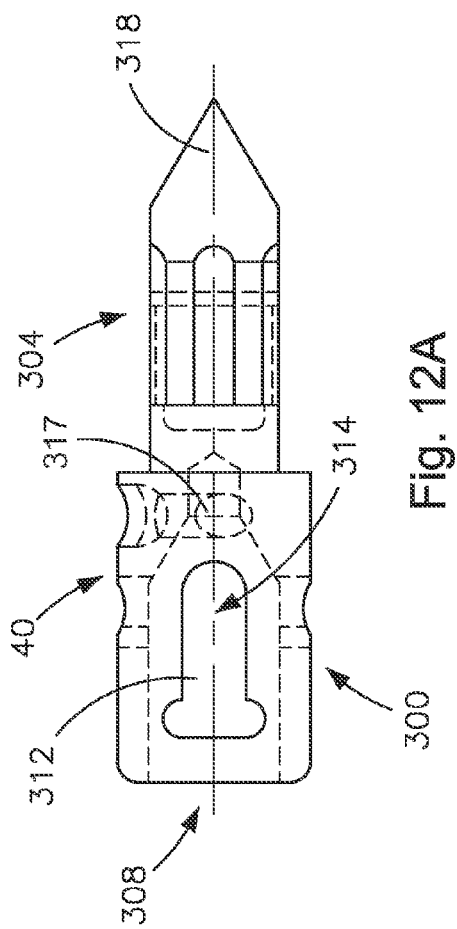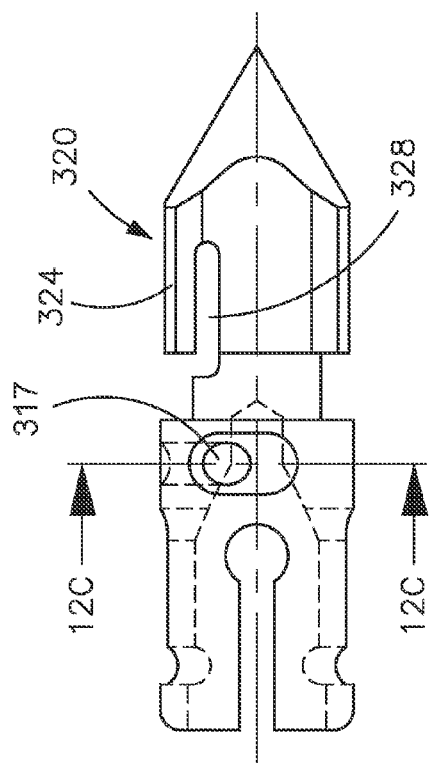

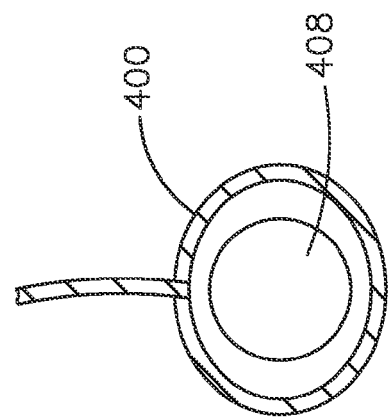
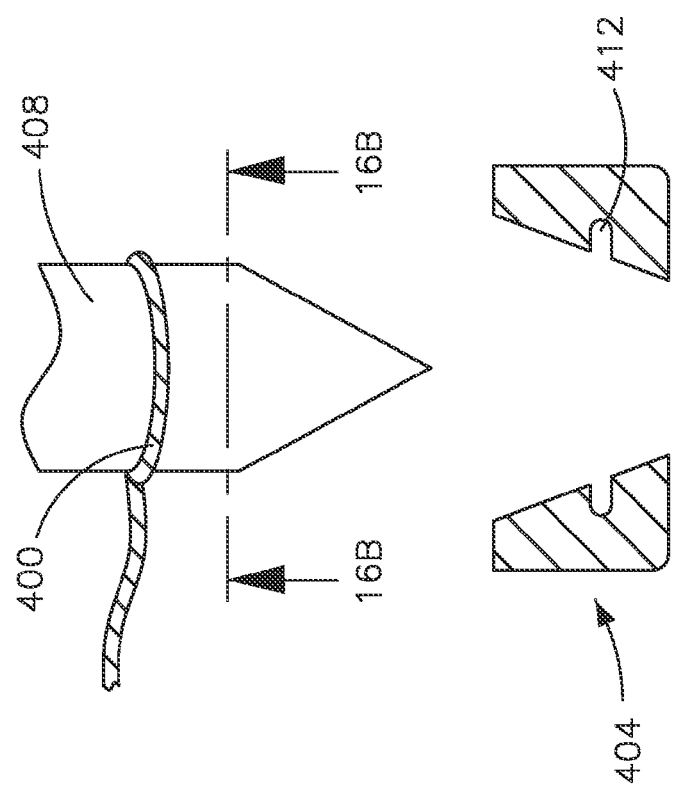
Fig. 16B
Fig. 16A

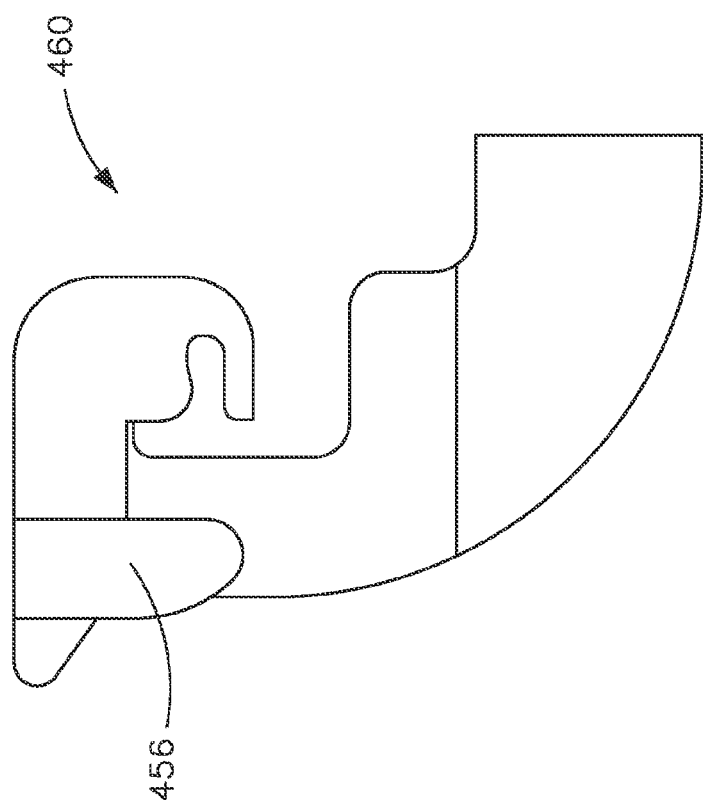

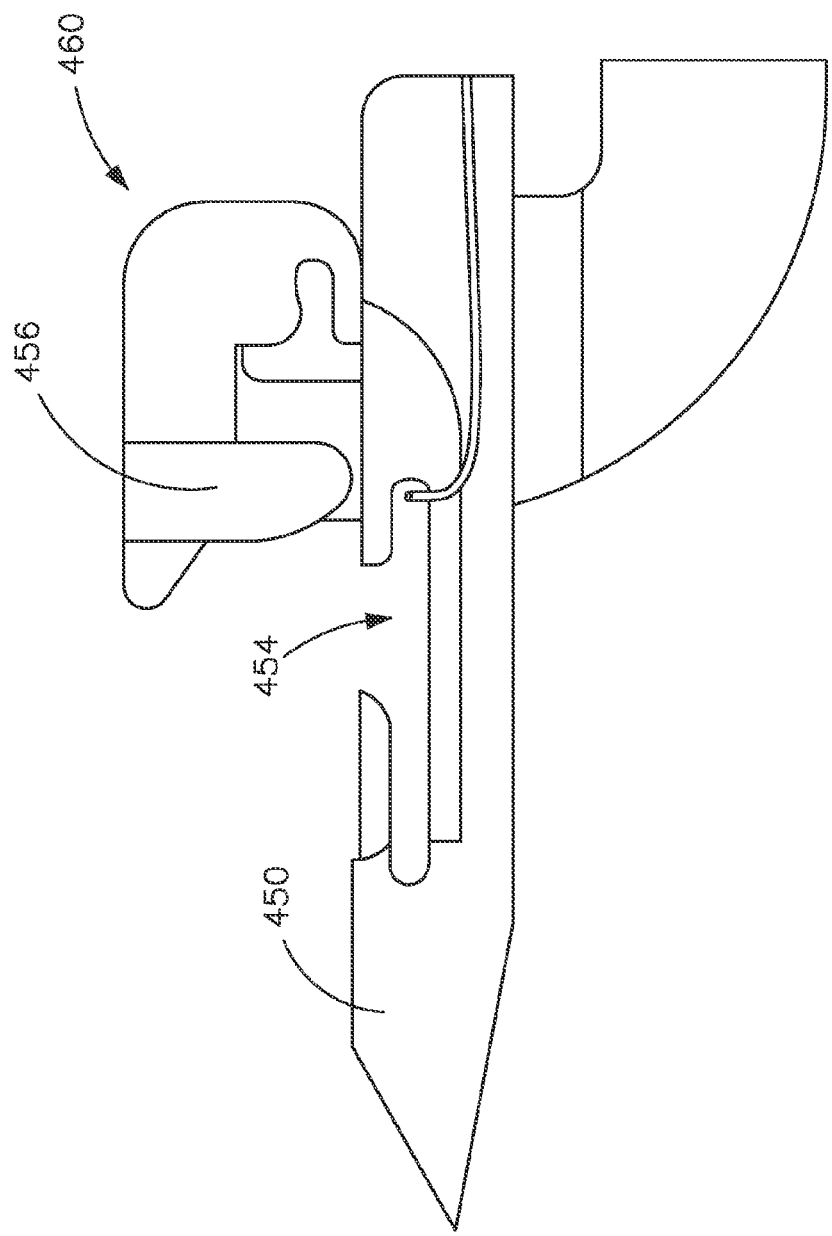

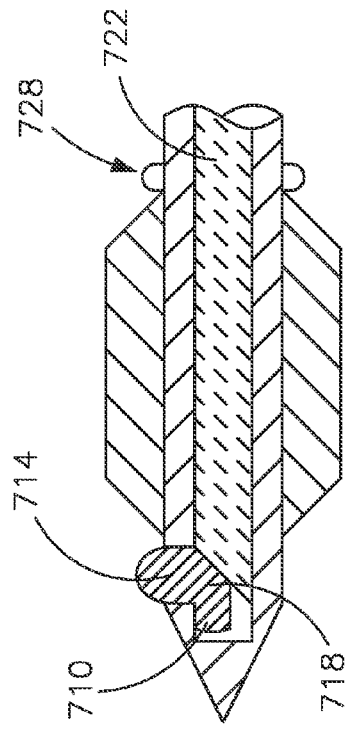
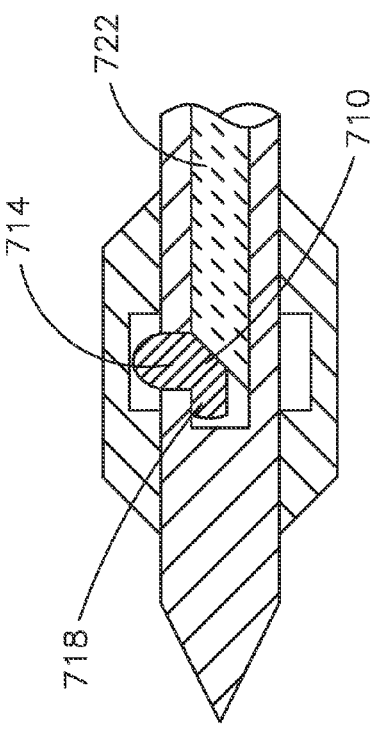
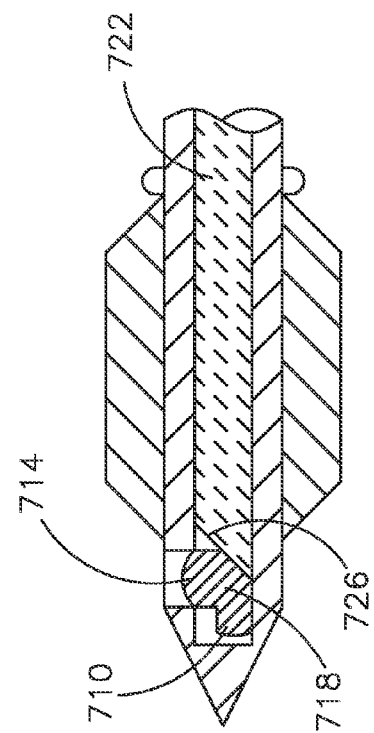
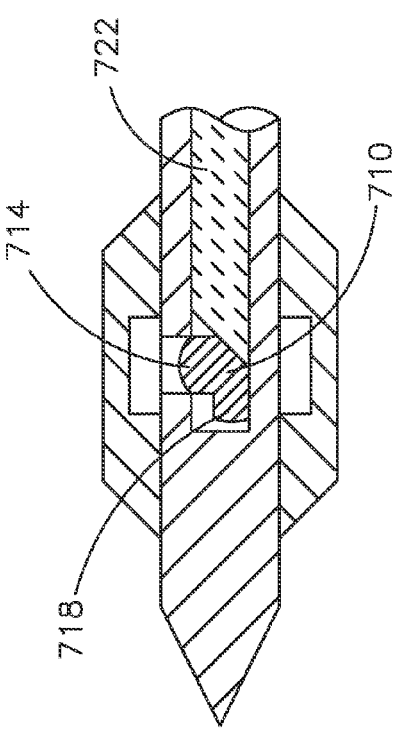

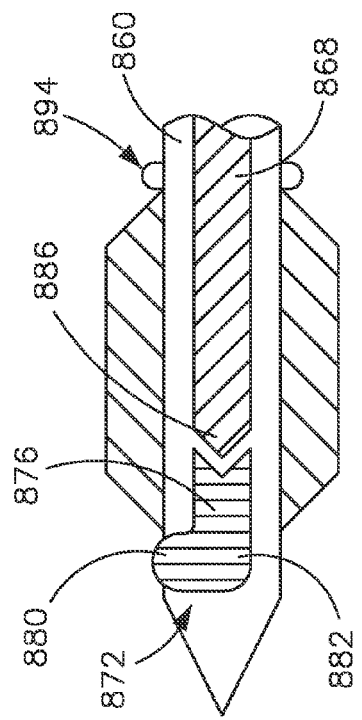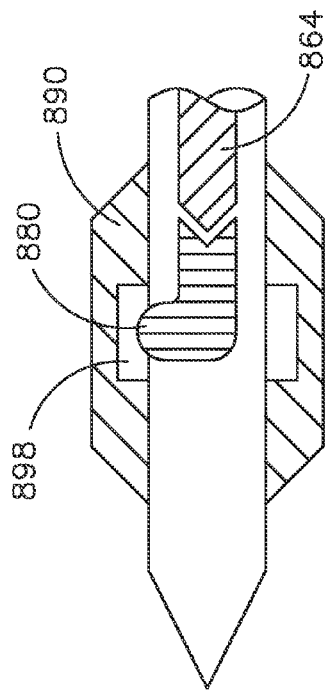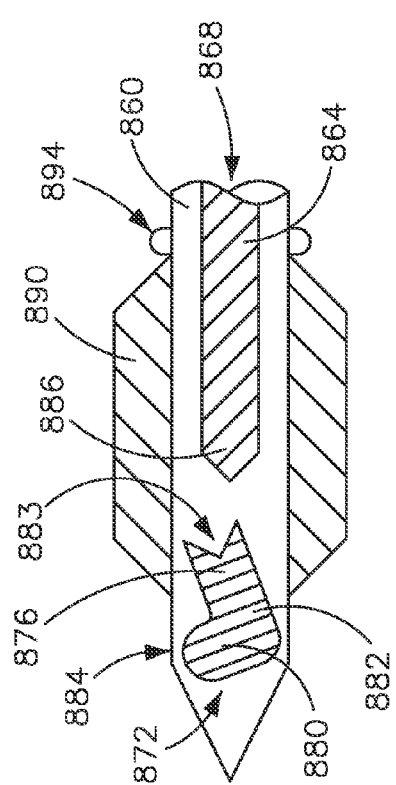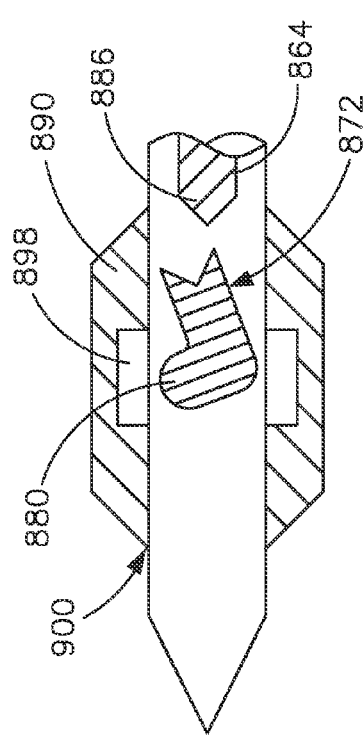

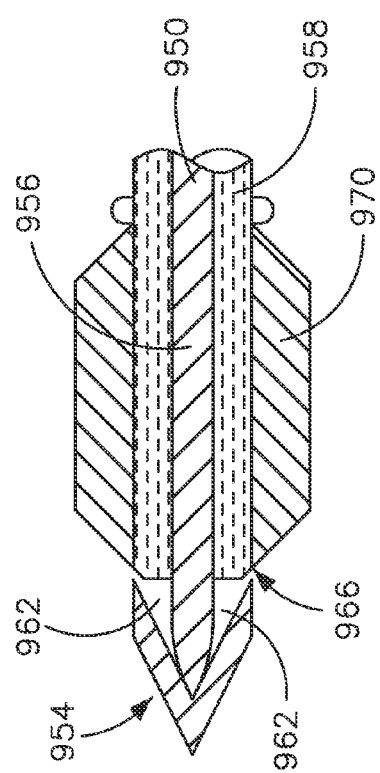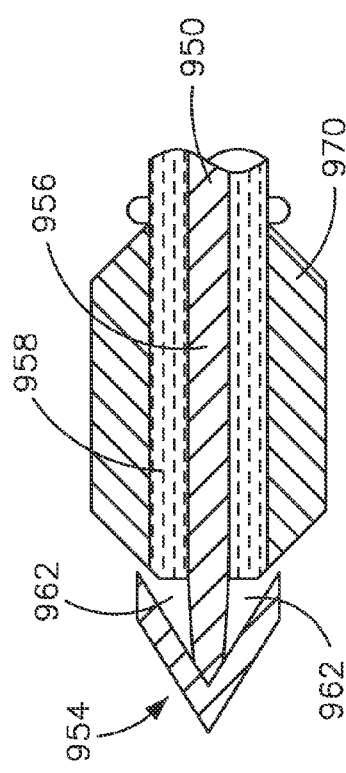

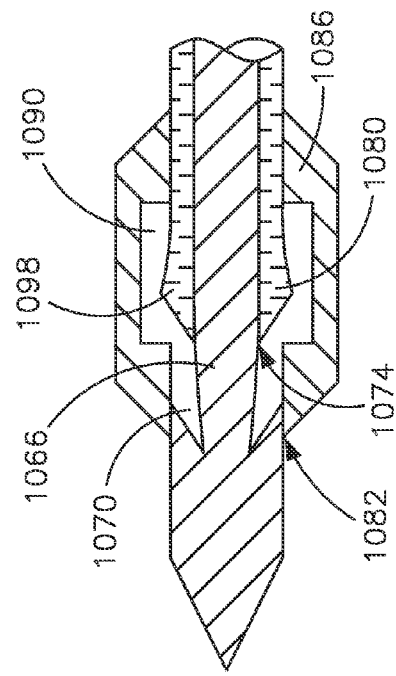
Fig. 34A
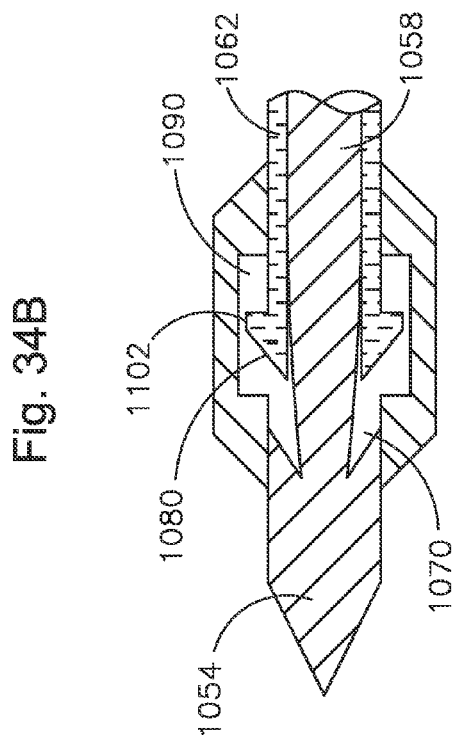
Fig. 34B
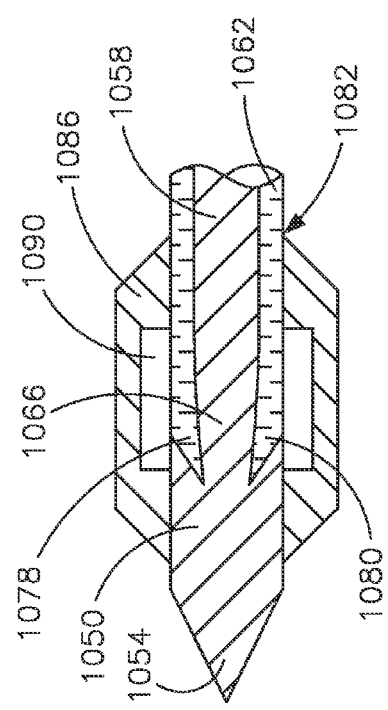
Fig. 34C
Fig. 34D

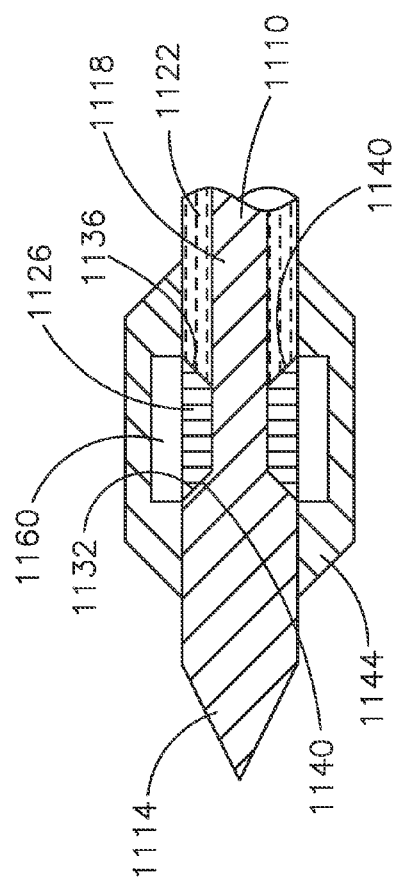
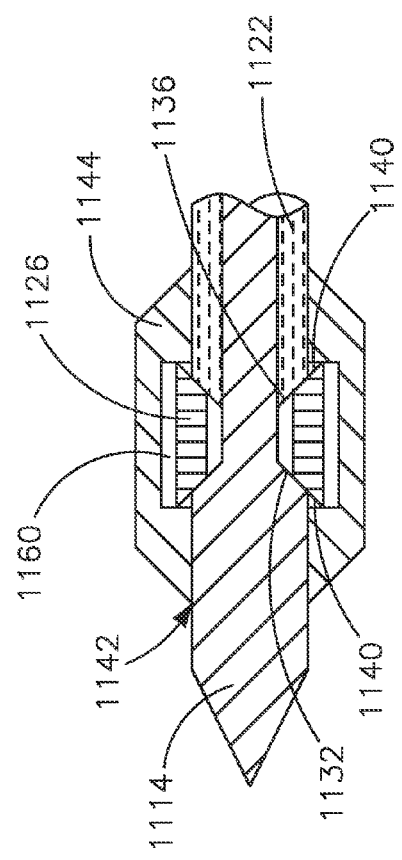

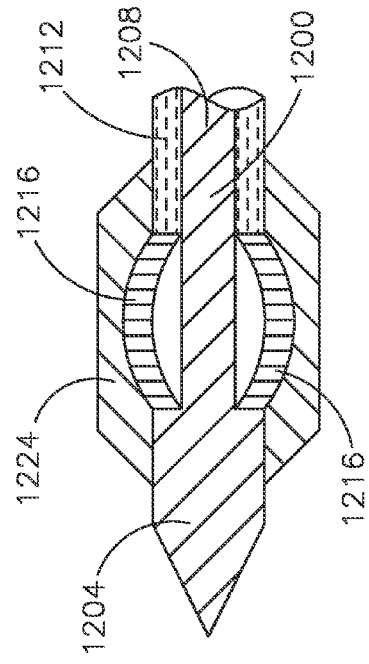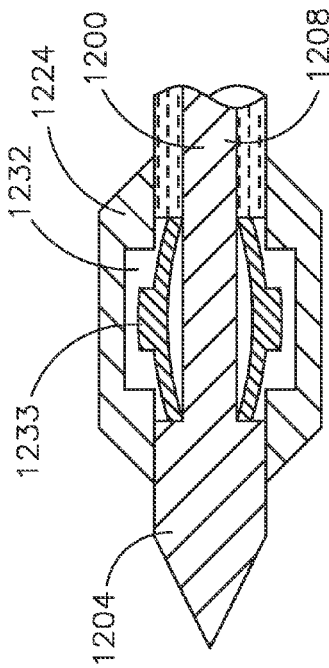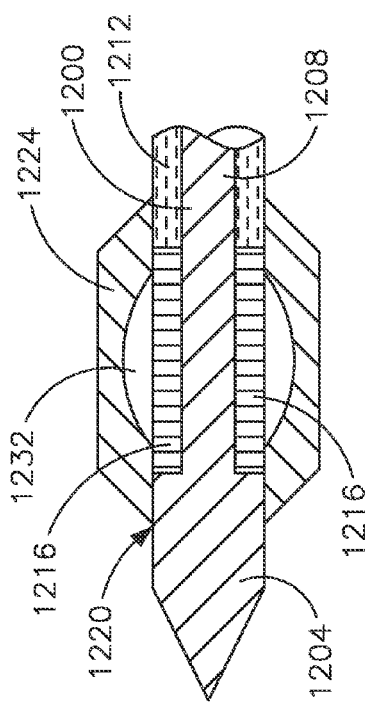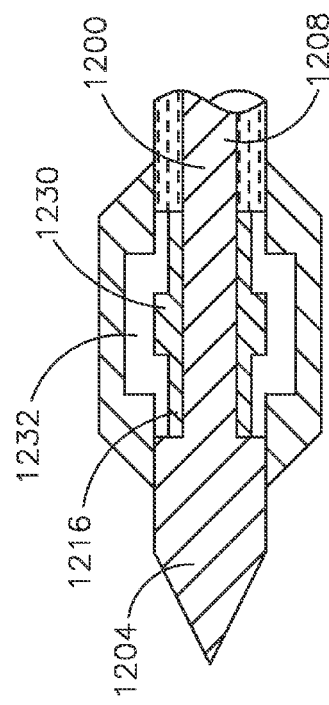

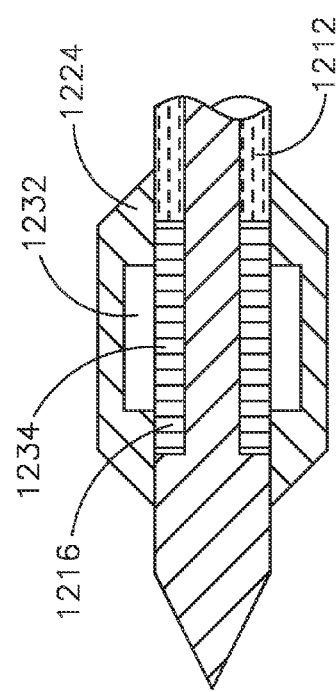
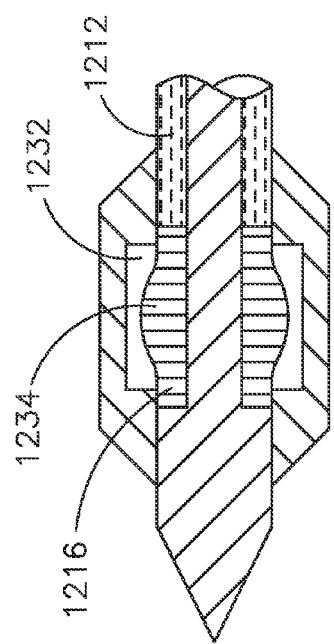
Fig. 38A
Fig. 38B

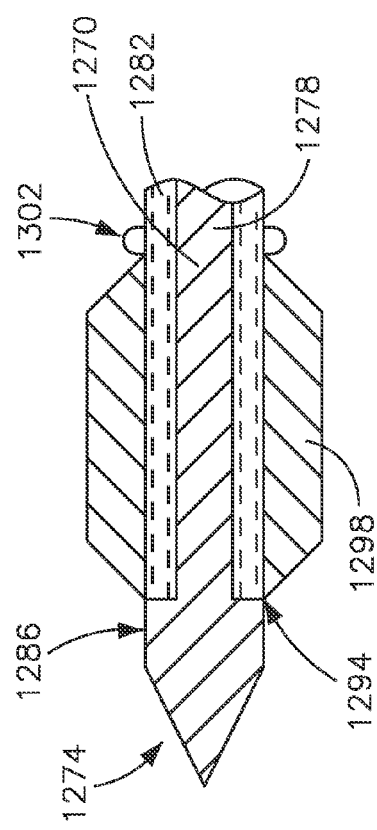
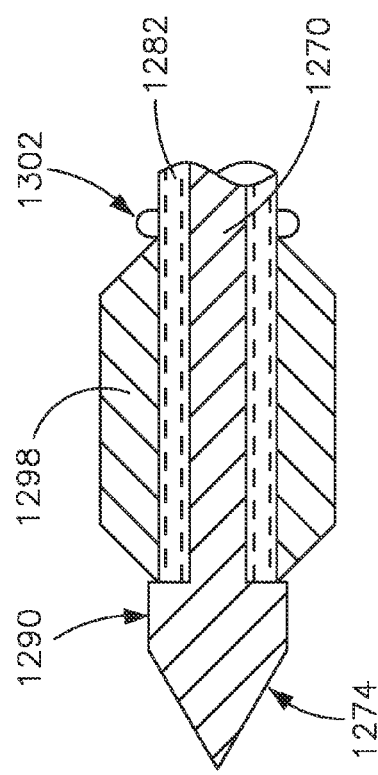

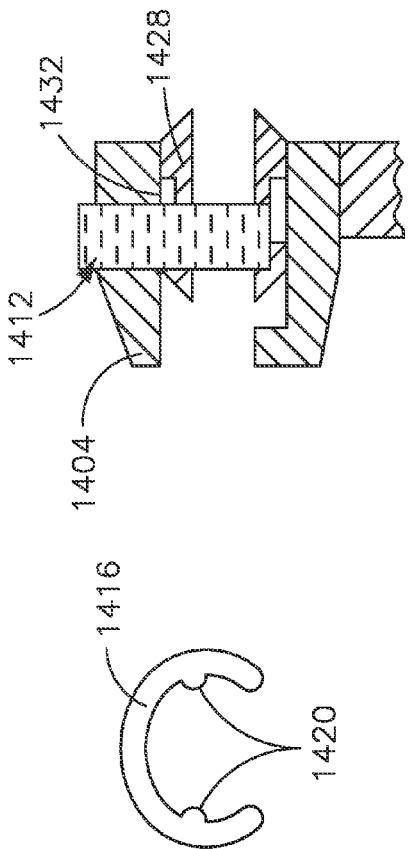
Fig. 45A
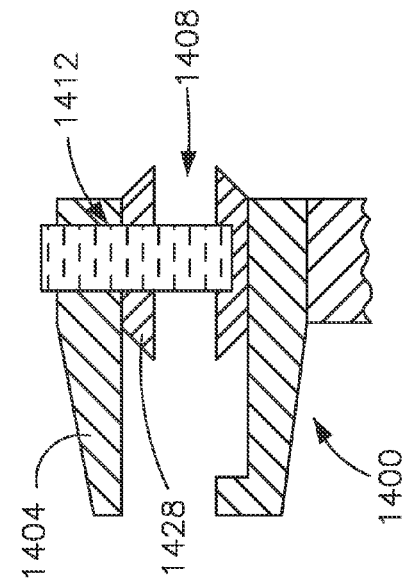
Fig. 45B
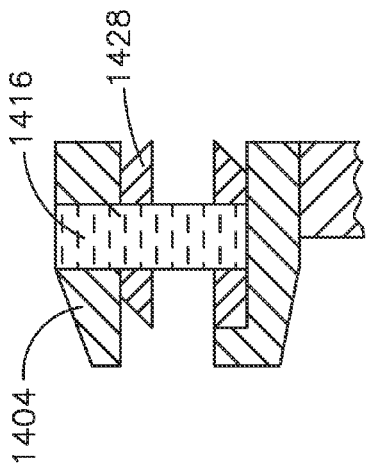
Fig. 44C
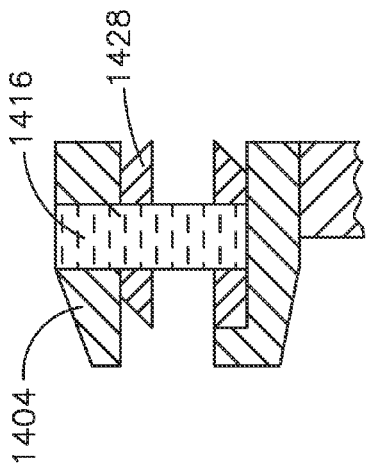
Fig. 44D
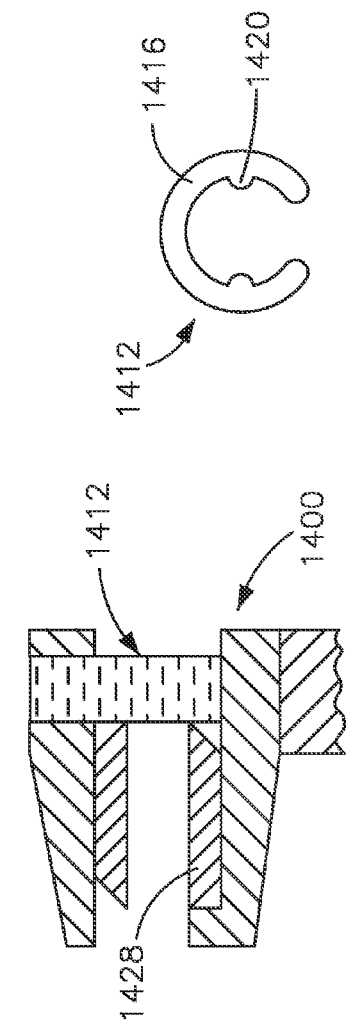
Fig. 44A
Fig. 44B

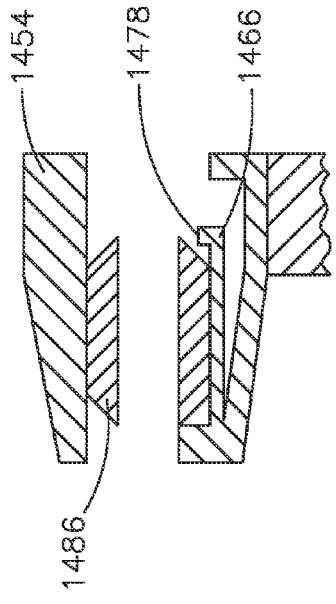
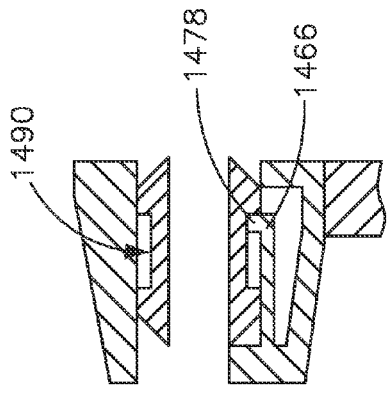
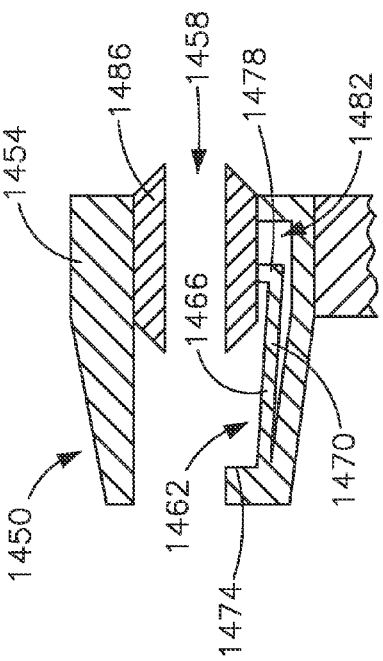
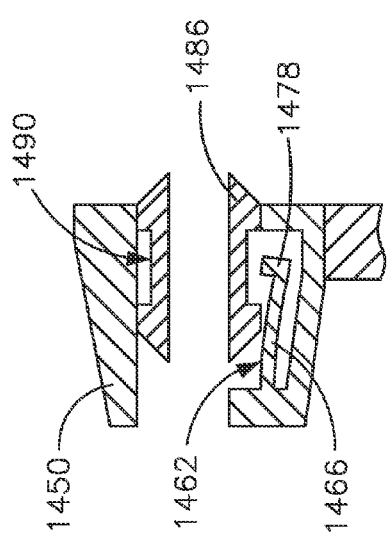

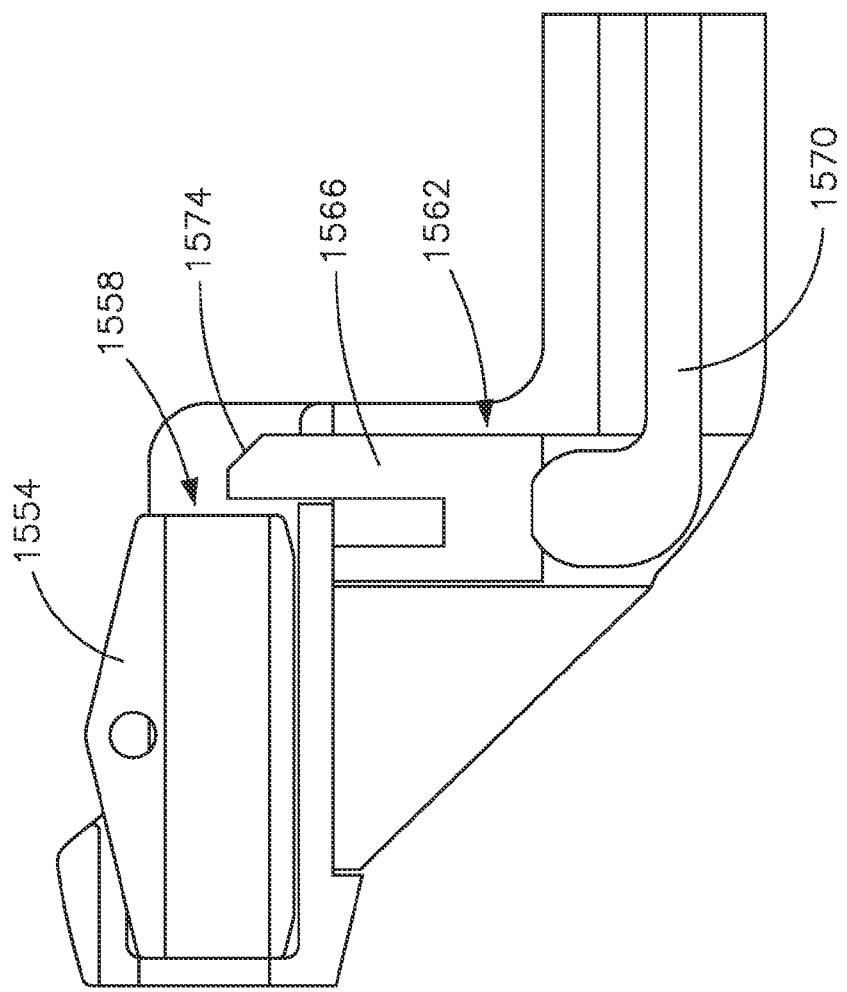

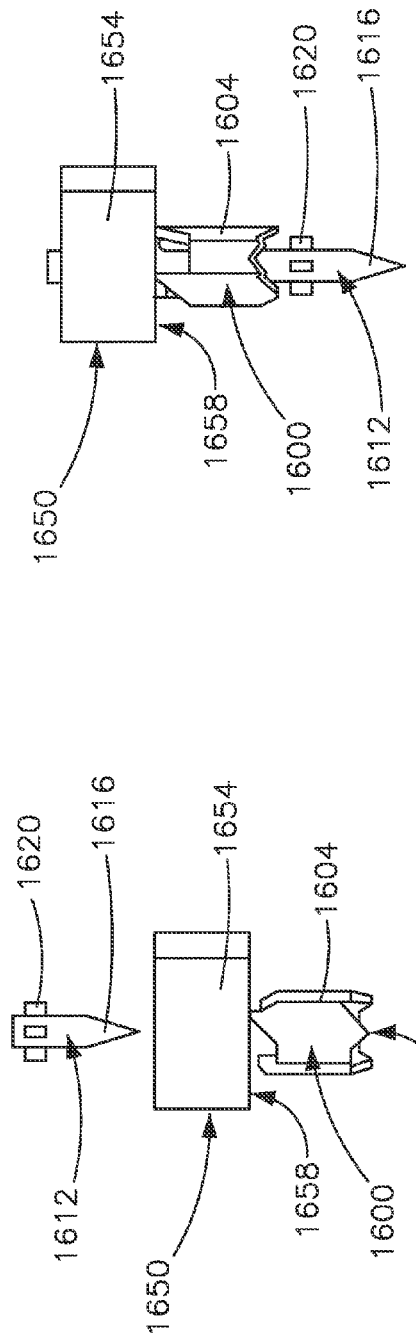
Fig. 51B
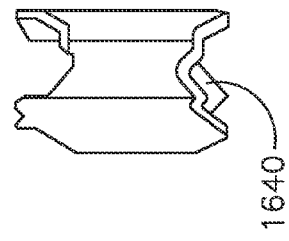
Fig. 51E
Fig. 51A
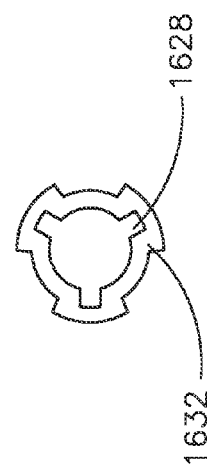
Fig. 51D
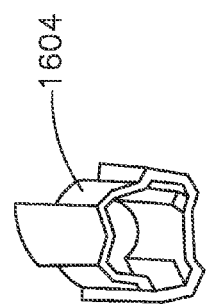
Fig. 51C

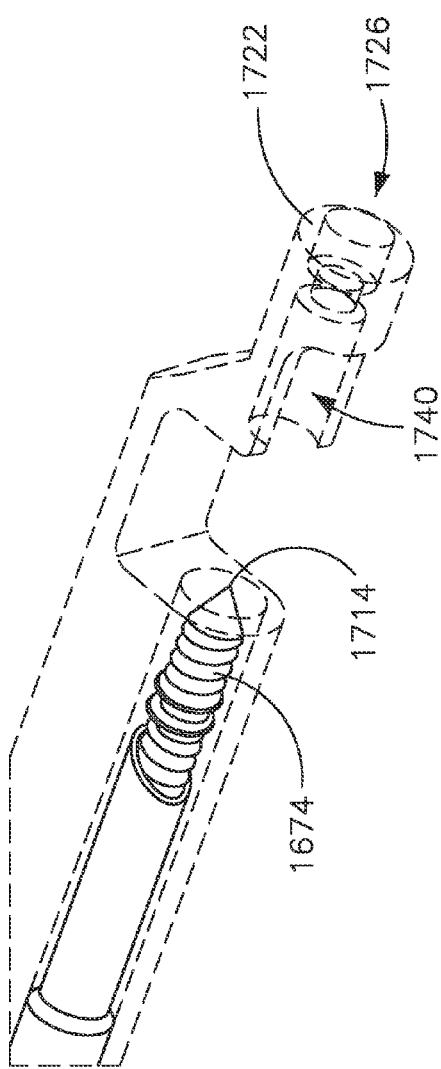
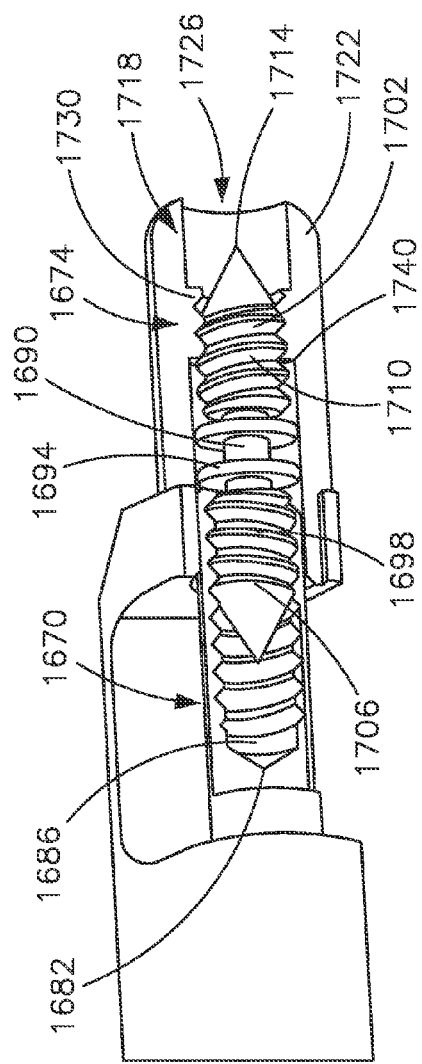

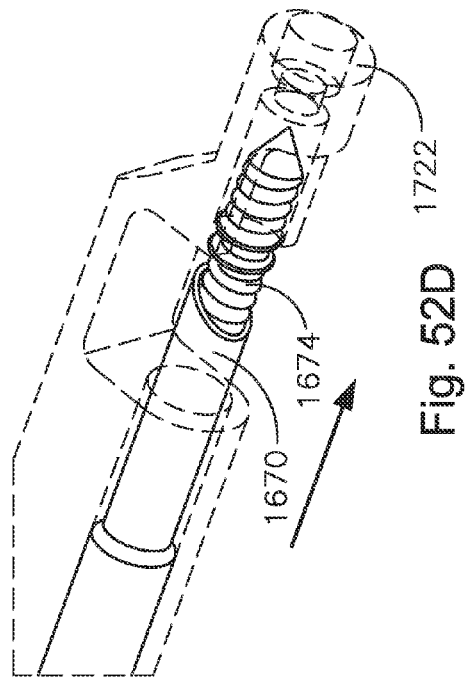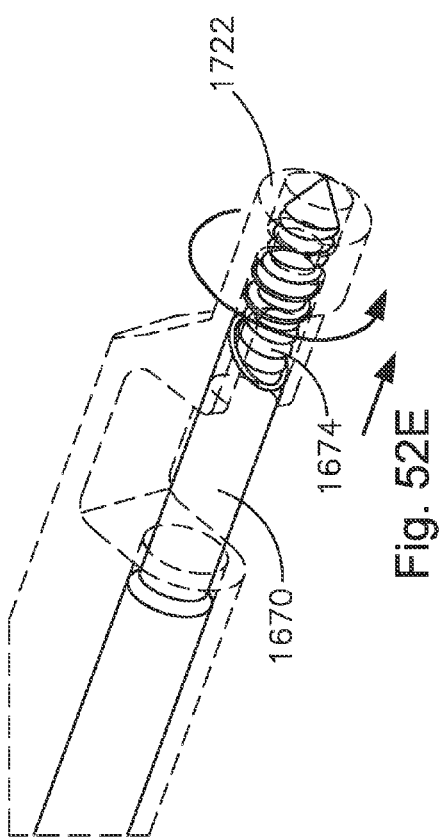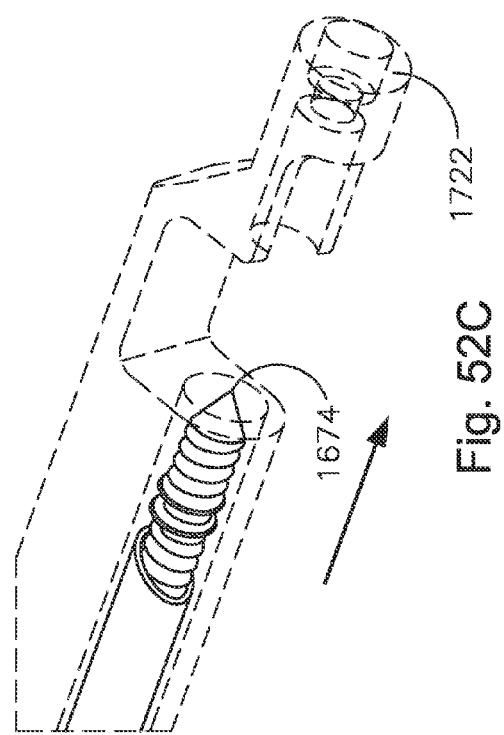

BI-DIRECTIONAL SUTURE PASSER

CROSS REFERENCE TO RELATED APPLICATIONS

This application claims priority to U.S. provisional application 61/147,251 filed Jan. 26, 2009, the contents of which are incorporated by reference in their entirety.

BACKGROUND

Suture passing is utilized in the repair of soft tissue defects. A suture is typically attached to either free needles or uni-directional suture passing instruments (instruments that pass suture through tissue in only one direction) for use in surgery.

A bi-directional suture passing instrument, one which can pass suture through tissue in a forward direction (away from the user), and in a rearward direction (toward the user), can have several advantages over uni-directional suture passing instruments. Many uni-directional suture passers require an additional step to manually retrieve and pass the suture in a reverse direction, thus increasing the complexity of the surgical technique and procedural time. Some uni-directional suture passer designs allow for instrumented retrieval and reloading of the suture to pass the suture; however these designs require that the tissue be flexible enough that it can be lifted to expose both a first and second side of the tissue to the distal end of the instrument in order to pass suture in a reverse direction and also require an additional step to reload the suture. A bi-directional suture passing instrument eliminates the manual retrieval step, decreases the complexity of the surgical technique and the procedural time, enhances the variety of stitch configurations that can be utilized, and increases the number of bodily tissues that can be surgically repaired.

Some bi-directional suture passer designs known in the art require that a tissue defect is approached generally parallel to the tissue, which is difficult for many surgical procedures such as disc annulus repair, due to the surgical approach to the disc space. Thus, it may be desirable to construct a suture passing device that enables bi-directional suture passing using an instrument that approaches the tissue defect generally perpendicularly.

Yet other bi-directional suture passer designs require that a sharp needle tip be passed through tissue in both directions. This needle passing is visible in one direction and blind in the other direction, which may result in surgical complications when working in areas adjacent to nerve roots, blood vessels, bowel, or other sensitive anatomy. Thus it may also be desirable to construct a bi-directional suture passing instrument that enables a sharp needle to be visible every time it is passed through tissue, thereby increasing surgical safety when operating in the areas of sensitive anatomy.

Furthermore, current bi-directional suture passer designs do not effectively detachably couple the suture to the needle. Thus, it may be desirable to construct new features for detachably coupling the suture to the needle, thereby improving the efficiency of the instrument.

SUMMARY

Various embodiments of a bi-directional suture passing instrument configured to approximate soft tissue defects are disclosed. In one embodiment the bi-directional suture passing instrument may include a body member, a boom arm extending from a distal end of the body member, and a needle reciprocally translatable within a needle receiving channel of the body member between an advanced position and a retracted position. The boom arm may include a boom arm housing spaced apart from the body member, and a tissue receiving gap may be disposed between the boom arm housing and the body member. The boom arm housing may define a locking interface, and the needle may define an engagement feature. A shuttling element may be detachably coupleable to both the needle and the boom arm housing. In that regard, the shuttling element may include an engagement feature corresponding to the engagement feature of the needle, and a locking mechanism corresponding to the locking interface of the boom arm housing. Rotation of the needle causes the engagement feature of the needle to engage the engagement feature of the shuttling element, to thereby detachably couple the shuttling element to the needle. Rotation of both the needle and the shuttling element causes the locking mechanism of the shuttling element to engage the locking interface of the boom arm housing to thereby detachably couple the shuttling element to the boom arm housing.

In another embodiment the suture passing instrument may include a body member, a boom arm extending from the body member, and a needle reciprocally translatable within a needle receiving channel of the body member between an advanced position and a retracted position. The boom arm may include a boom arm housing spaced apart from the body member such that a tissue receiving gap is defined therebetween. The boom arm housing defines a locking interface, and the needle may include a channel and an engagement feature disposed within the channel between an extended position and a retracted position. When in the extended position, the engagement feature may detachably couple a shuttling element to the needle, and when in the retracted position, the engagement feature decouples the shuttling element from the needle.

In another embodiment the suture passing instrument may include a body member, a boom arm extending from a distal end of the body member, and a needle reciprocally translatable within a channel of the body member between an advanced position and a retracted position. The needle may include a shaft and a head extending from the shaft. A sleeve may be disposed around the shaft of the needle, the sleeve being configured to allow translation of either the sleeve or the needle with respect to the other. Both the needle and sleeve may received by a bore that extends through a shuffling element. Translation of either the needle or the sleeve detachably couples the shuttling element to the needle.

Methods of operating the different embodiments of the bi-directional suture passing instrument are also disclosed. For example, in one embodiment the needle may be rotated such that an engagement feature of the needle engages an engagement feature of the shuttling element to thereby detachably couple the shuffling element to the needle. The needle and shuttling element may then be passed through tissue and into the boom arm housing. By rotating the needle again, a locking mechanism of the shuffling element engages a locking interface of the boom arm housing to thereby detachably couple the shuffling element to the boom arm housing. Further rotation of the needle will disengage the needle from the shuffling element and the needle may be retracted while leaving the shuffling element in the boom arm housing. These steps may be repeated as many times as necessary.

BRIEF DESCRIPTION OF THE DRAWINGS

The foregoing summary, as well as the following detailed description of preferred embodiments of the instrument of the present application, will be better understood when read in conjunction with the appended drawings. For the purposes of illustrating the suture passer instrument of the present application, there is shown in the drawings preferred embodiments. It should be understood, however, that the application is not limited to the precise arrangements and instrumentalities shown. In the drawings:

FIG. 1A is a top plan view of a bi-directional suture passing instrument in accordance with an embodiment of the present invention;

FIG. 1B is a side cross-sectional view of the bi-directional suture passing instrument shown in FIG. 1A, through the line 1B-1B;

FIG. 1C is an enlarged side cross-sectional view taken within window 1C of FIG. 1B showing a portion of a boom arm and a body element of the instrument;

FIG. 2A is a side elevational view of a handle of the instrument shown in FIGS. 1A-1B;

FIG. 2B is a top plan view of the handle shown in FIG. 2A;

FIG. 2C is a front elevational view of the handle shown in FIG. 2A;

FIG. 3A is a fragmented top plan view of an actuator element of the instrument shown in FIGS. 1A-1B;

FIG. 3B is a fragmented side elevational view of the actuator element shown in FIG. 3A;

FIG. 3C is a front elevational view of the actuator element shown in FIG. 3A;

FIG. 3D is a rear elevational view of the actuator element shown in FIG. 3A;

FIG. 4A is a side elevational view of a thumb ring of the instrument shown in FIGS. 1A-1B;

FIG. 4B is top plan view of the thumb ring shown in FIG. 4A;

FIG. 4C is a front elevational view of the thumb ring shown in FIG. 4A;

FIG. 5A is a side perspective view of an actuator stop element of the instrument shown in FIGS. 1A-1B;

FIG. 5B is a front elevational view of the actuator stop element shown in FIG. 5A;

FIG. 5C is a side elevational view of the actuator stop element shown in FIG. 5A;

FIG. 6A is a front side elevational view of a thumb ring lock element of the instrument shown in FIGS. 1A-1B;

FIG. 6B is a right plan view of the thumb ring lock element shown in FIG. 6A;

FIG. 8A is a fragmented top plan view of a body element of the instrument shown in FIGS. 1A-1B;

FIG. 8B is a front cross-sectional view of the body element shown in FIG. 8A, taken along the line 8B-8B;

FIG. 9A is a front elevational view of a tip actuator element of the instrument shown in FIGS. 1A-1B;

FIG. 9B is an enlarged front elevational view of the tip actuator element taken from within oval 9B of FIG. 9A;

FIG. 9C is a left side elevational view of the tip actuator element shown in FIG. 9A;

FIG. 9D is a right side elevational view of the tip actuator element shown in FIG. 9A;

FIG. 10B is a top plan view of the boom arm shown in FIG. 10A;

FIG. 10C is a side cross-sectional view of the boom arm shown in FIG. 10A;

FIG. 11A illustrates a fragmented top plan view of a needle of the instrument shown in FIGS. 1A-1B;

FIG. 11B is a front cross-sectional view of the needle shown in FIG. 11A, taken along line 11B-11B;

FIG. 11C is a side elevational view of the needle, taken from within oval 11C of FIG. 11A;

FIG. 11D is an enlarged top plan view of the needle taken from within oval 11D of FIG. 11A detailing the distal end of the needle;

FIG. 11E is a partial side elevational view of the distal end of the needle shown in FIG. 11D;

FIG. 12A is a top plan view of a shuttling element of the instrument shown in FIGS. 1A-1B;

FIG. 12B is a side elevational view of the shuttling element shown in FIG. 12A;

FIG. 12C is a cross-sectional view of the shuttling element shown in FIG. 12B, taken along line 12C-12C;

FIG. 12D is a front elevational view of the shuttling element shown in FIG. 12A;

FIG. 16A is a partial side elevational view showing another embodiment of the bi-directional suture passing instrument, in which the suture is formed into a loop around the needle, and configured to be selectively coupleable to a boom arm housing, the boom arm housing is shown in cross section for clarity;

FIG. 16B is a cross sectional view of the bi-directional suture passing instrument shown in FIG. 16A through the line 16B-16B;

FIG. 17B is a side cross section view of the boom arm housing illustrated in FIG. 17A, showing the needle in a retracted position;

FIG. 17D is a side cross-sectional view of the boom arm housing illustrated in FIG. 17C, showing the needle fully advanced into the boom arm housing;

FIG. 24A is a partial side cross-sectional view of another embodiment of the bi-directional suture passing instrument, in which a deployable wire stop having a hemispheric top and triangular bottom, is used to detachably couple the shuttling element to the needle;

FIG. 24B is a partial side cross-sectional view of the instrument illustrated in FIG. 24A, showing the ball stop fully deployed by a wedge;

FIG. 24C is a partial side cross-sectional view of the instrument shown in FIG. 24A having a shuttling element that defines a recess that is configured to be engaged by the ball stop;

FIG. 24D is a partial side cross-sectional view of the instrument illustrated in FIG. 24C, showing the ball stop fully deployed by a wedge, and engaging the recess of the shuttling element;

FIG. 29A is a partial side cross-sectional view of another embodiment of the bi-directional suture passing instrument, in which a deployable boot stop is used to detachably couple the shuttling element to the needle;

FIG. 29B is a partial side cross-sectional view of the instrument illustrated in FIG. 29A, showing the boot stop fully deployed by a wedge;

FIG. 30A is a partial side cross-sectional view of the instrument shown in FIG. 29A having a shuttling element that defines a recess that is configured to be engaged by the boot stop;

FIG. 30B is a partial side cross-sectional view of the instrument illustrated in FIG. 30A, showing the boot stop fully deployed by a wedge, and engaging the recess of the shuttling element;

FIG. 32A is a partial side cross-sectional view of another embodiment of the bi-directional suture passing instrument, in which an expandable needle tip is used to detachably couple the shuttling element to the needle;

FIG. 32B is a partial side cross-sectional view of the instrument illustrated in FIG. 32A, showing the expandable needle tip deployed by a wedge, to thereby couple the shuttling element to the needle;

FIG. 34A is a partial side cross-sectional view of another embodiment of the bi-directional suture passing instrument, in which an alternative expandable sleeve is used to detachably couple the shuttling element to the needle;

FIG. 34B is a partial side cross-sectional view of the instrument illustrated in FIG. 34A, showing the expandable sleeve deployed by retracting the sleeve along the needle shaft, to thereby couple the shuttling element to the needle;

FIG. 34C is a partial side cross-sectional view of another embodiment of the bi-directional suture passing instrument, in which an alternative expandable sleeve having radially extending protrusions is used to detachably couple the shuttling element to the needle;

FIG. 34D is a partial side cross-sectional view of the instrument illustrated in FIG. 34C, showing the expandable sleeve deployed by retracting the sleeve along the needle shaft, to thereby couple the shuttling element to the needle;

FIG. 35A is a partial side cross-sectional view of another embodiment of the bi-directional suture passing instrument, in which an expandable split ring is used to detachably couple the shuttling element to the needle;

FIG. 35B is a partial side cross-sectional view of the instrument illustrated in FIG. 35A, showing the expandable split ring deployed by a wedge, to thereby couple the shuttling element to the needle;

FIG. 36A is a partial side cross-sectional view of another embodiment of the bi-directional suture passing instrument, in which an expandable cage is used to detachably couple the shuttling element to the needle;

FIG. 36B is a partial side cross-sectional view of the instrument illustrated in FIG. 36A, showing the expandable cage deployed by compressing the cage with a sleeve, to thereby couple the shuttling element to the needle;

FIG. 37A is a partial side cross-sectional view of another embodiment of the bi-directional suture passing instrument, in which an expandable cage having a radially extending protrusion is used to detachably couple the shuttling element to the needle;

FIG. 37B is a partial side cross-sectional view of the instrument illustrated in FIG. 37A, showing the expandable cage deployed by compressing the cage with a sleeve, to thereby couple the shuttling element to the needle;

FIG. 38A is a partial side cross-sectional view of another embodiment of the bi-directional suture passing instrument, in which a cage having an expandable portion is used to detachably couple the shuttling element to the needle;

FIG. 38B is a partial side cross-sectional view of the instrument illustrated in FIG. 38A, showing the expandable portion of the cage deployed by compressing the cage with a sleeve, to thereby couple the shuttling element to the needle;

FIG. 39A is a partial side cross-sectional view of another embodiment of the bi-directional suture passing instrument, in which an elliptical needle head is used to detachably couple the shuttling element to the needle;

FIG. 39B is a partial side cross-sectional view of the instrument illustrated in FIG. 39A, showing the elliptical needle head deployed by rotating the needle 90 degrees, to thereby couple the shuttling element to the needle;

FIG. 40A is a partial side cross-sectional view of another embodiment of the bi-directional suture passing instrument, in which a spring loaded transverse member is used to retain the shuttling element in the boom arm housing;

FIG. 40B is a partial side cross-sectional view of the instrument illustrated in FIG. 40A, shown the transverse member engaging a proximal edge of the shuttling element to thereby couple and retain the shuttling element within the boom arm housing;

Figure 40A:
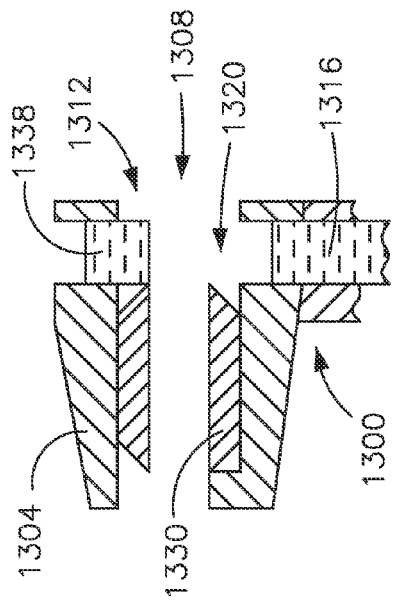
Figure 41A:
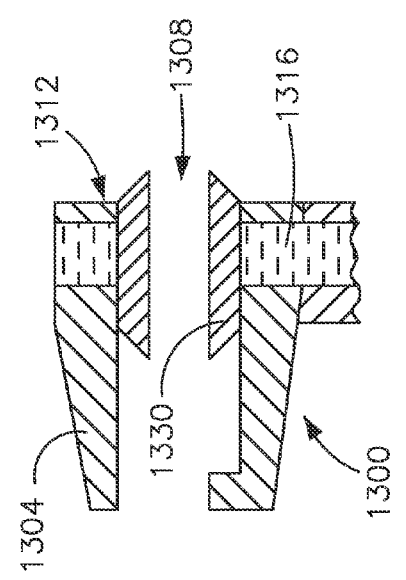
Figure 41B:
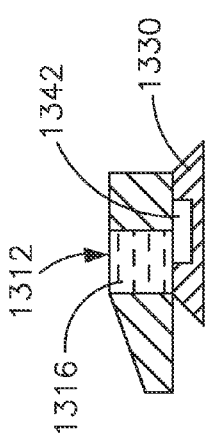
Figure 42A:
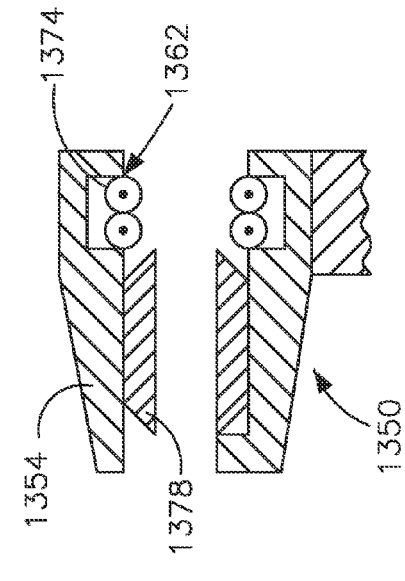
Figure 42B:
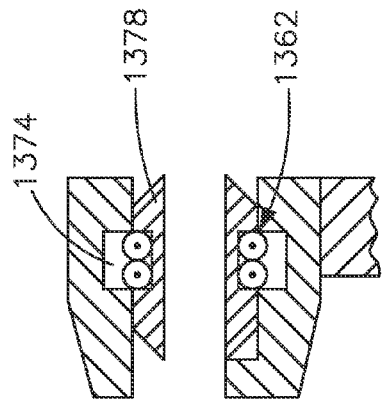
Figure 43A:
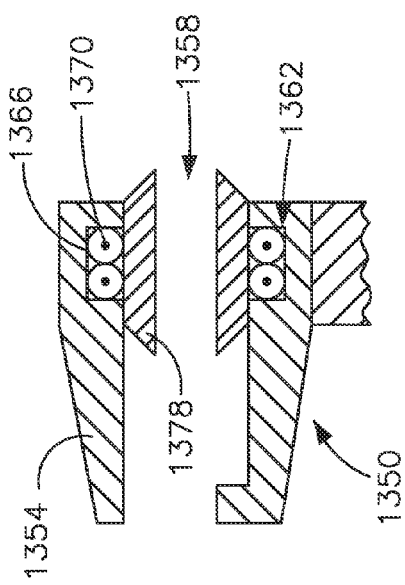
Figure 43B:
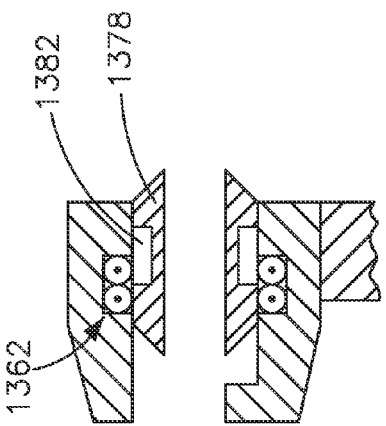
Figure 48A:
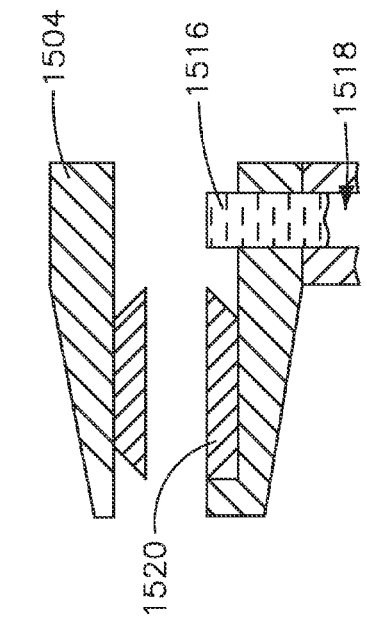
Figure 48B:
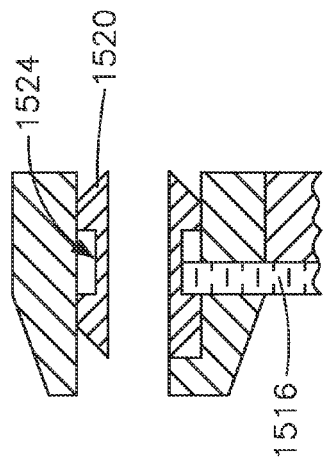
Figure 49A:
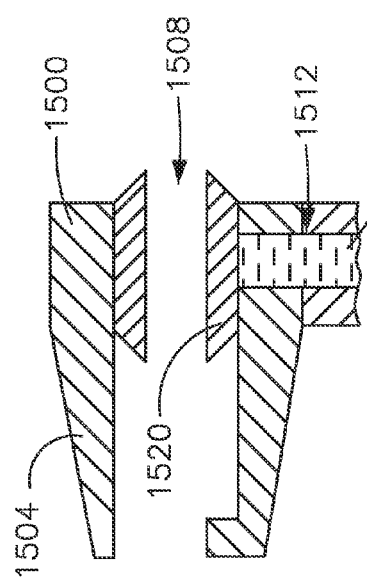
Figure 49B:
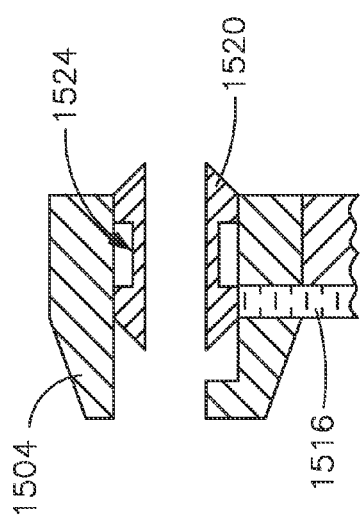
Figure 50A:
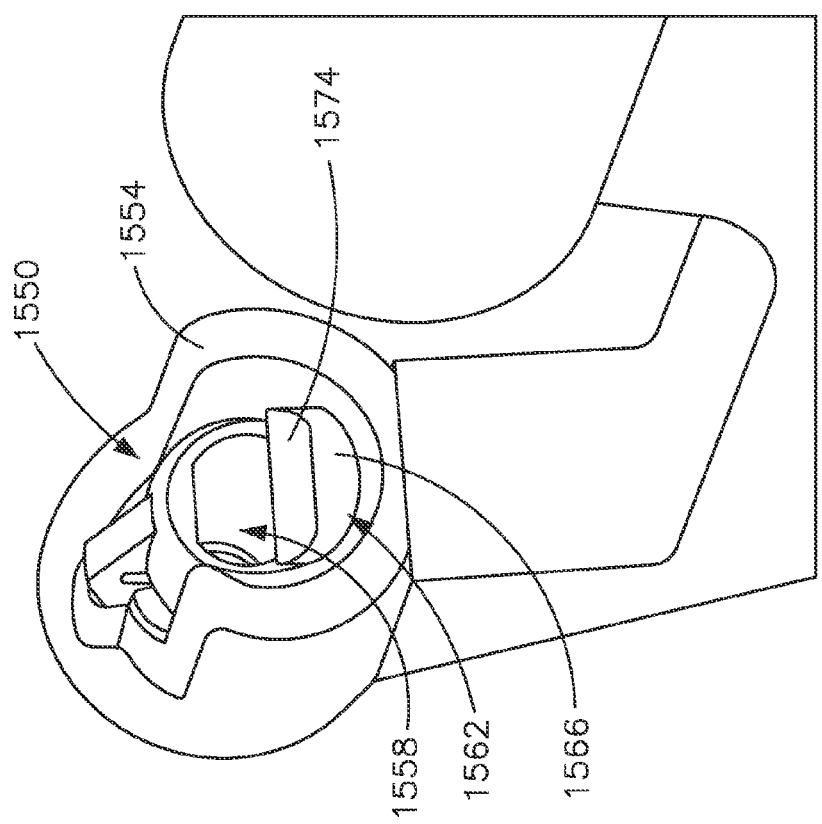
Figure 52F:
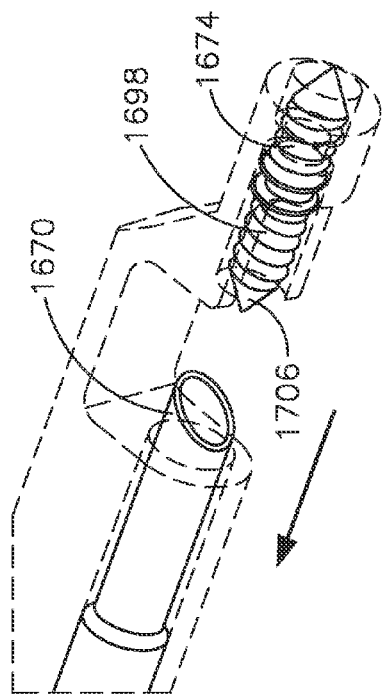
Figure 52G:
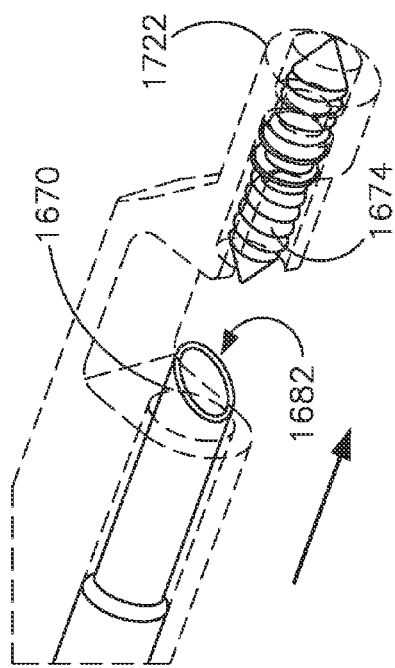
Figure 52H:
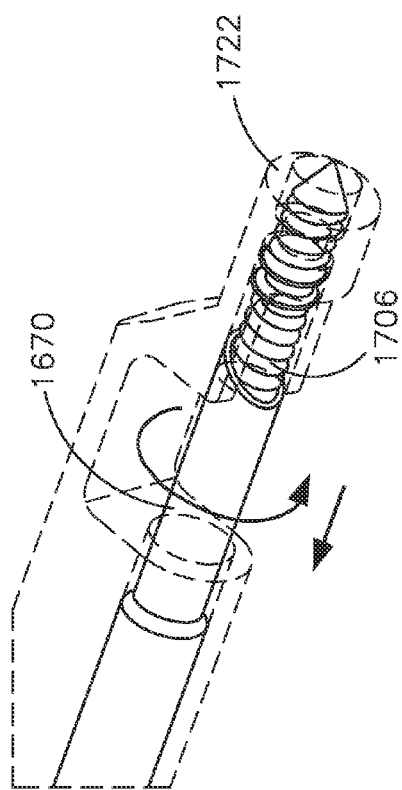
Figure 52I:
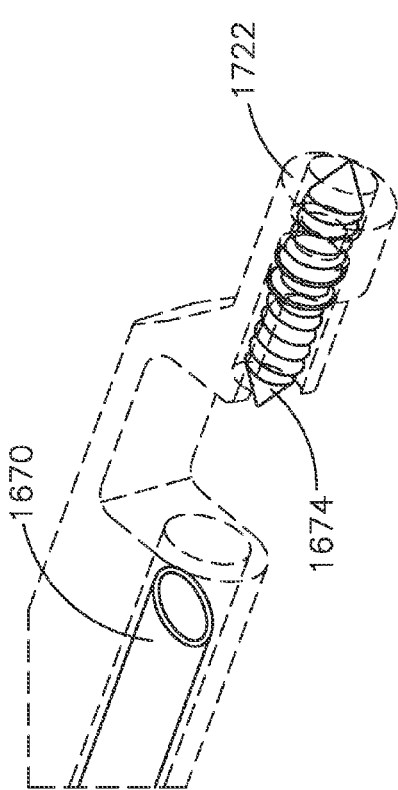
Figure 52K:
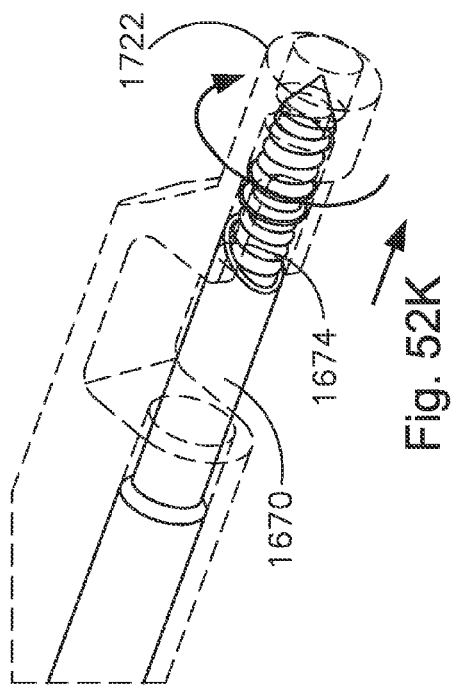
Figure 52J:
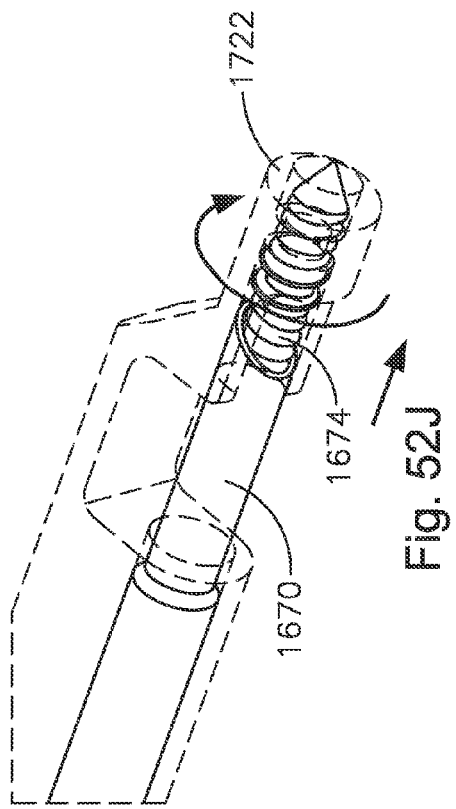
Figure 52L:
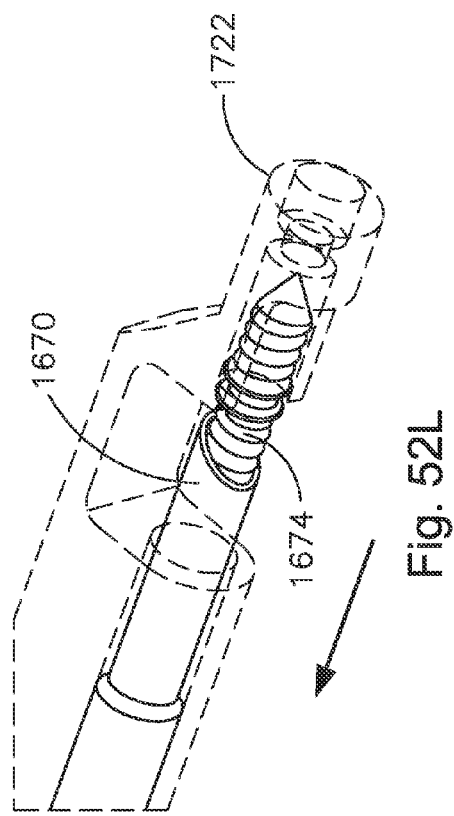
Figure 53A:
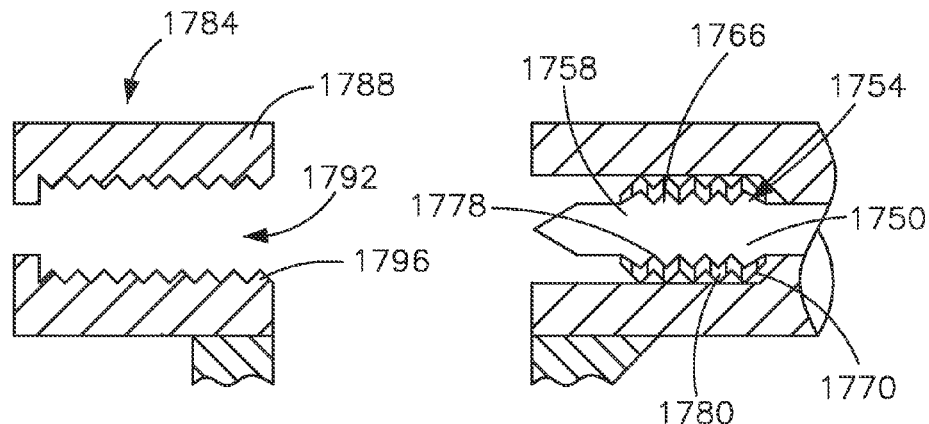
Figure 53B:
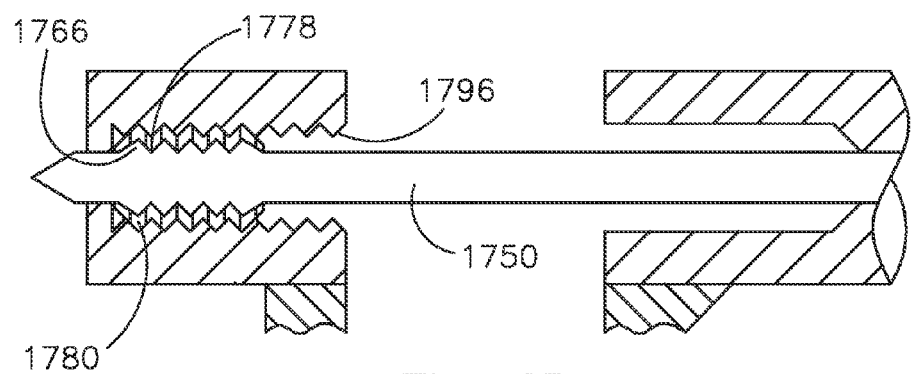
Figure 53C:
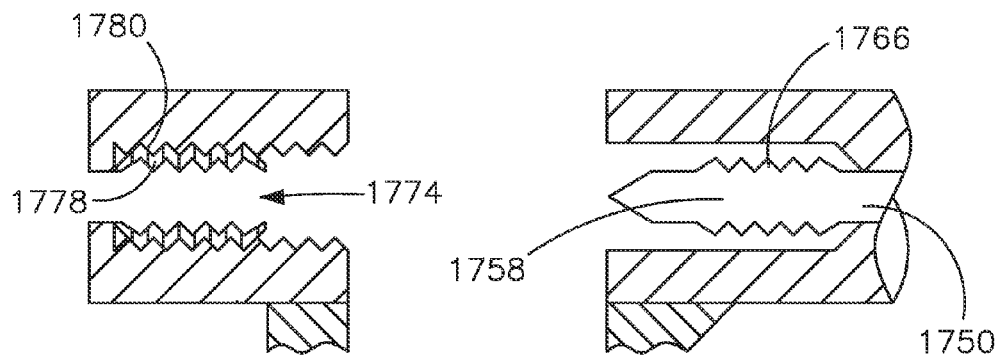
Figure 54A:
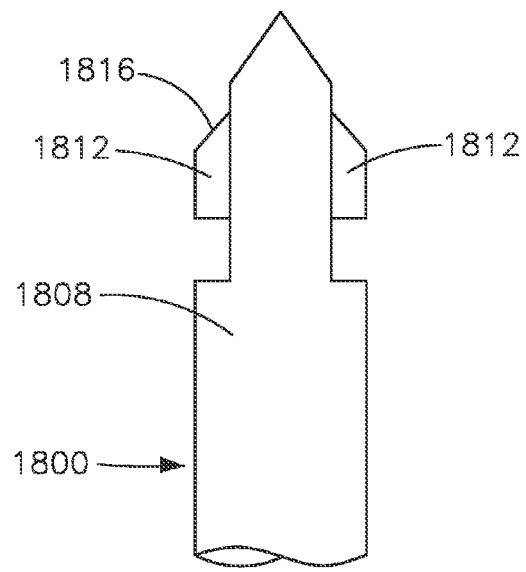
Figure 54B:
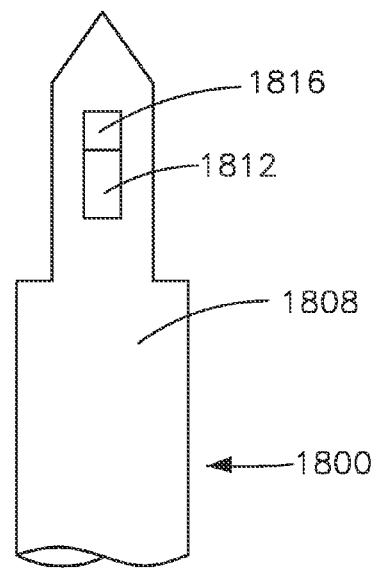
Figure 54C:
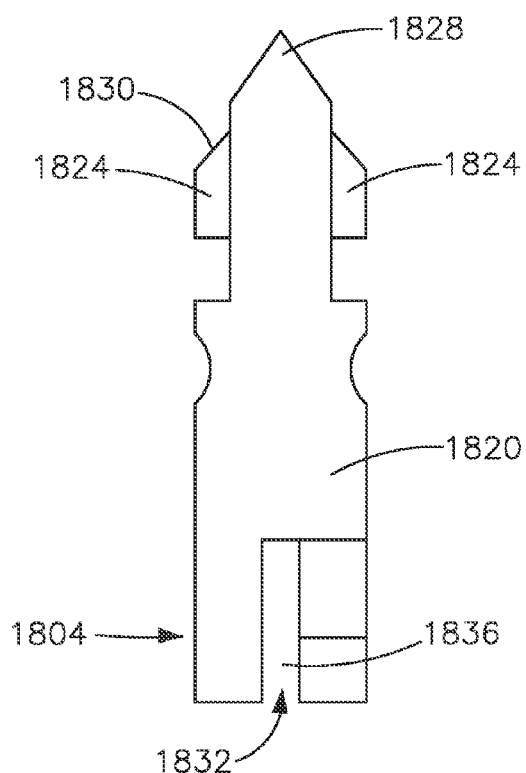
Figure 54D:
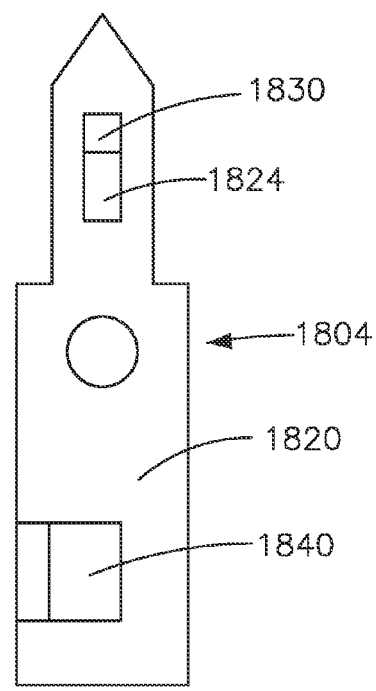
Figure 54E:
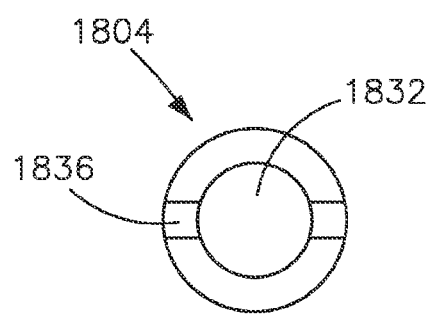
Figure 54F:
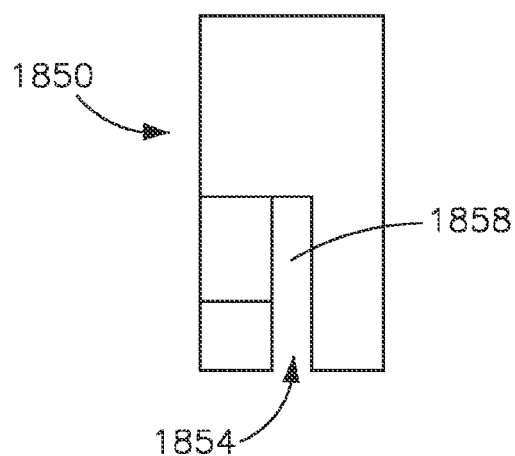
Figure 54G:
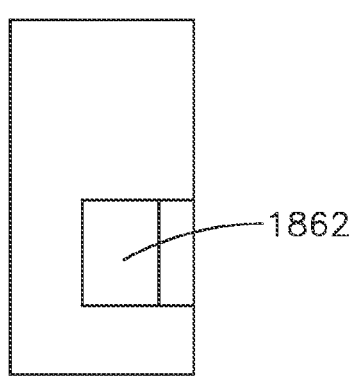
Figure 54H:
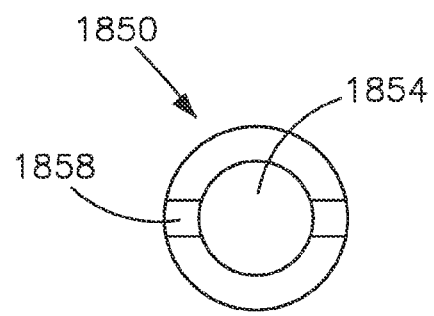
Figure 54I:
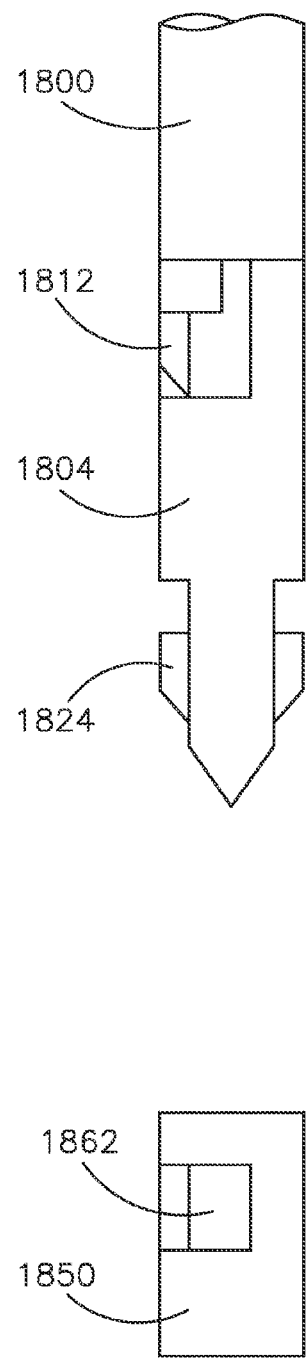
Figure 54J:
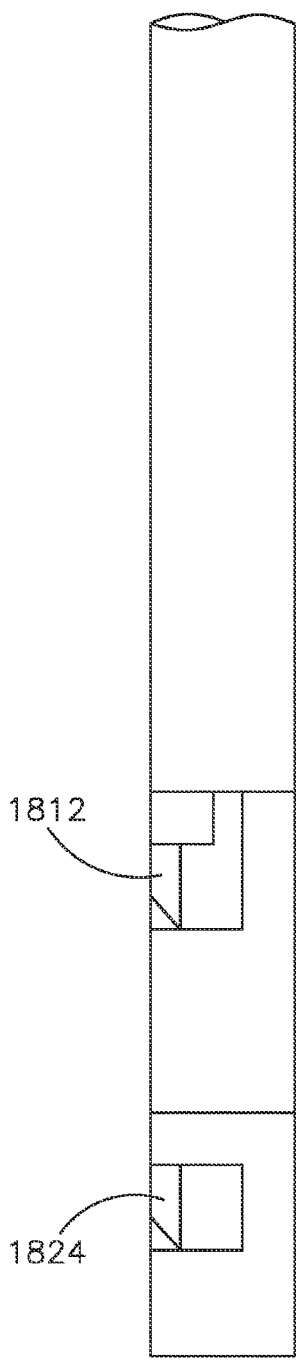
Figure 54K:
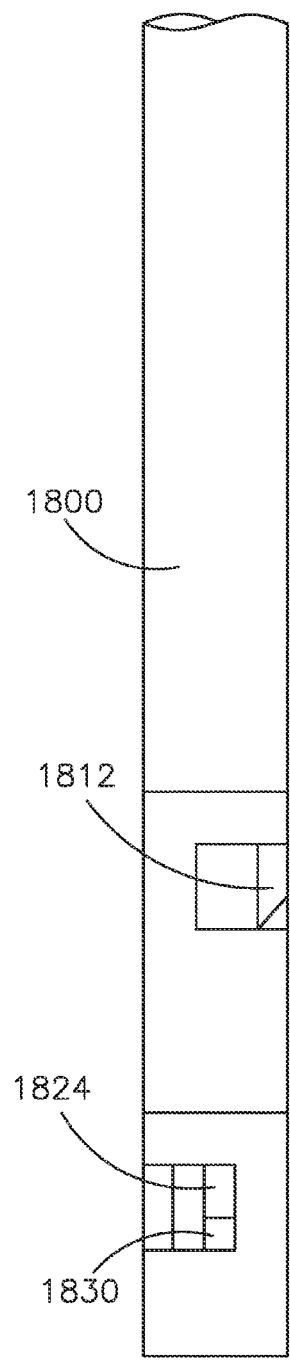
Figure 54L:
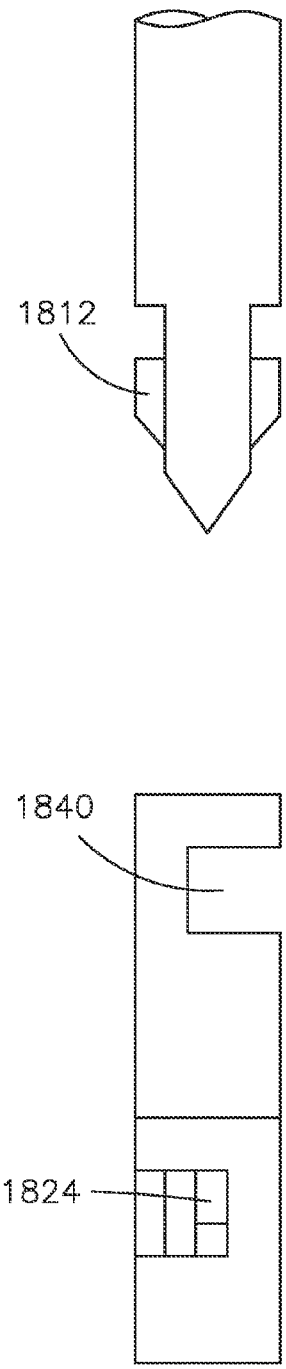
Figure 54M:
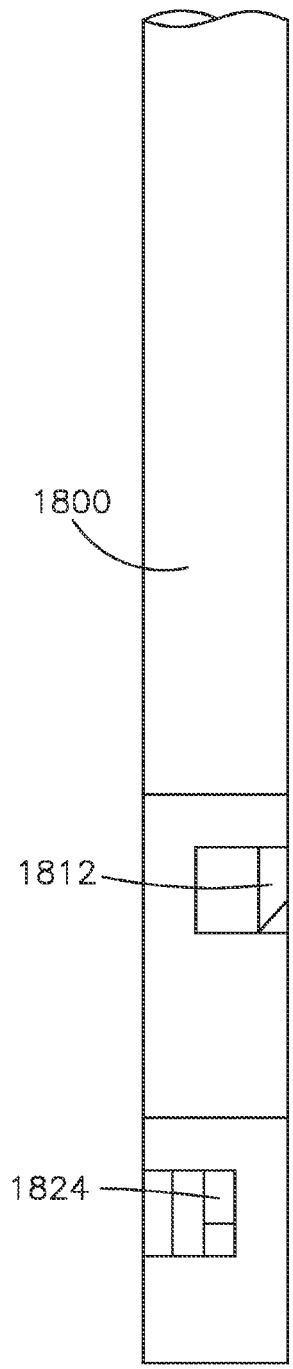
Figure 54N:
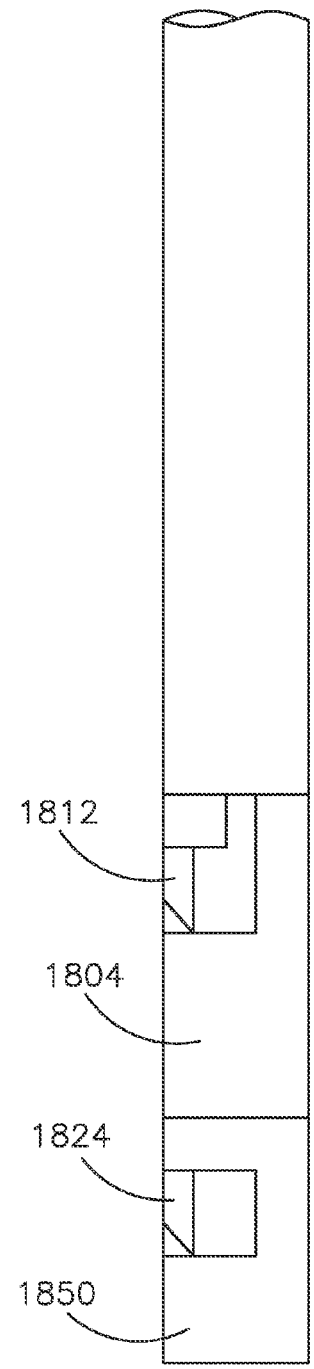
Figure 55:
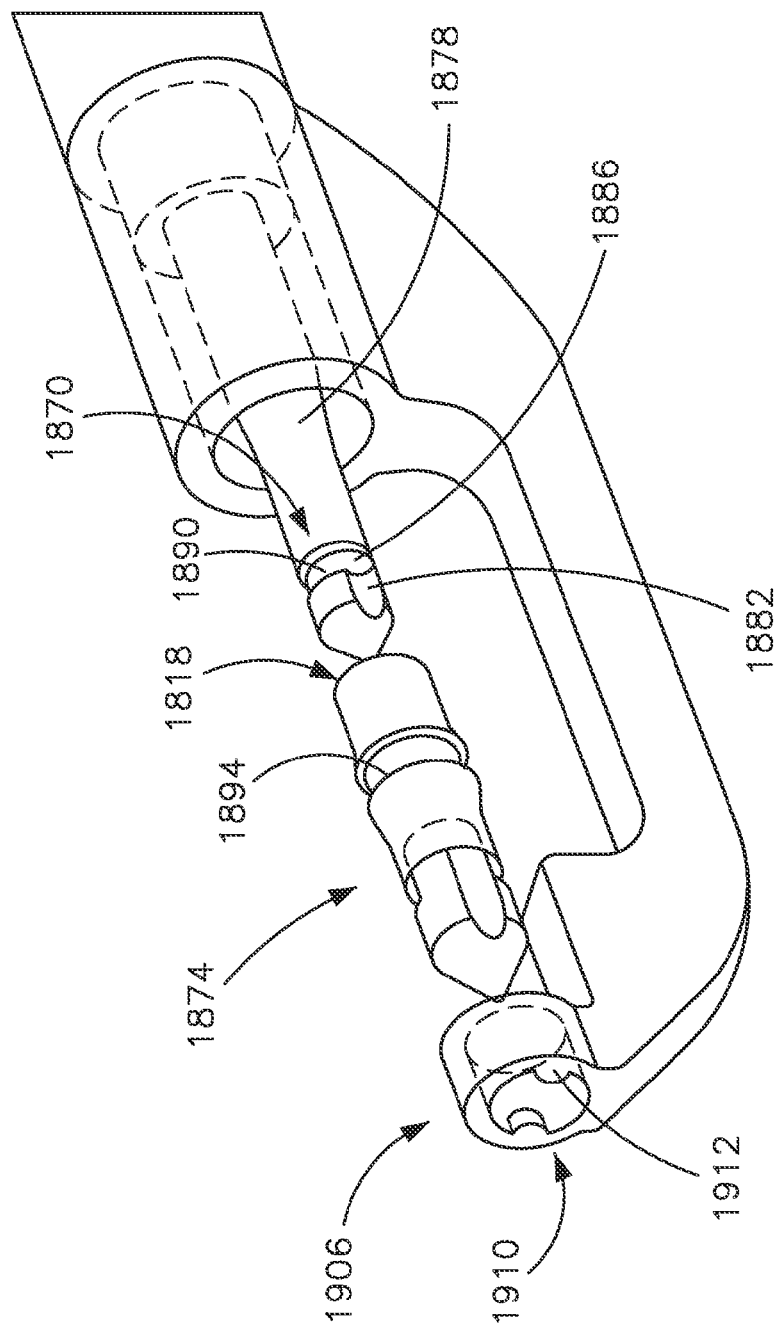
Figure 56A:
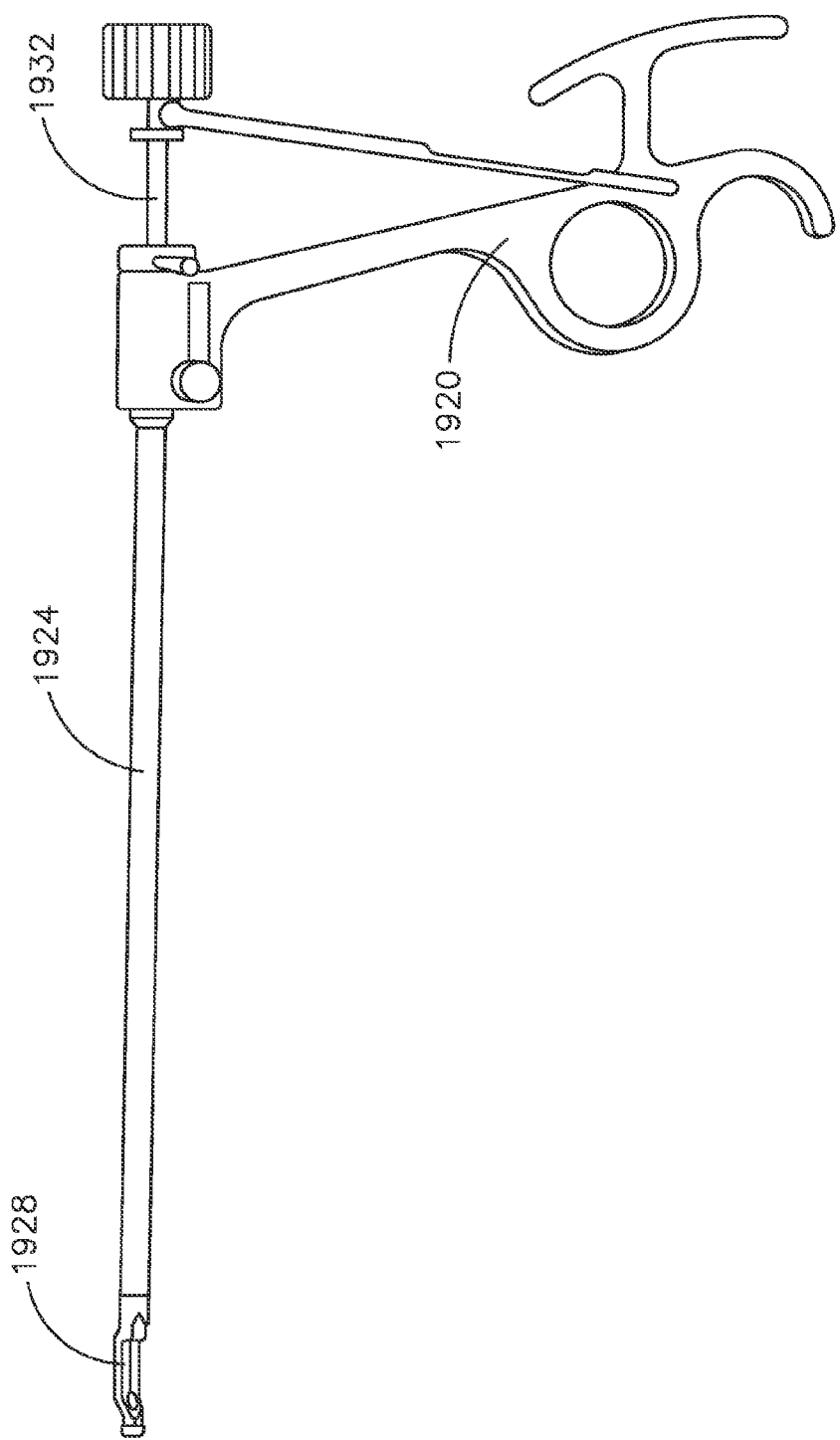
Figure 56B:
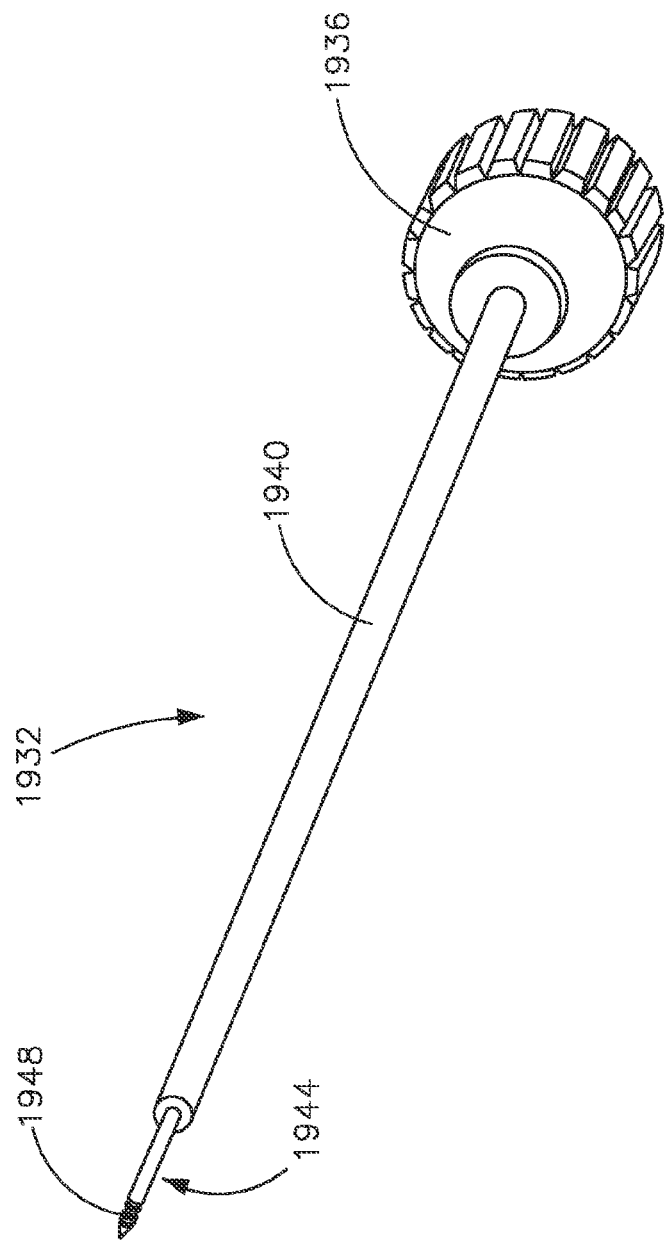
Figure 56C:
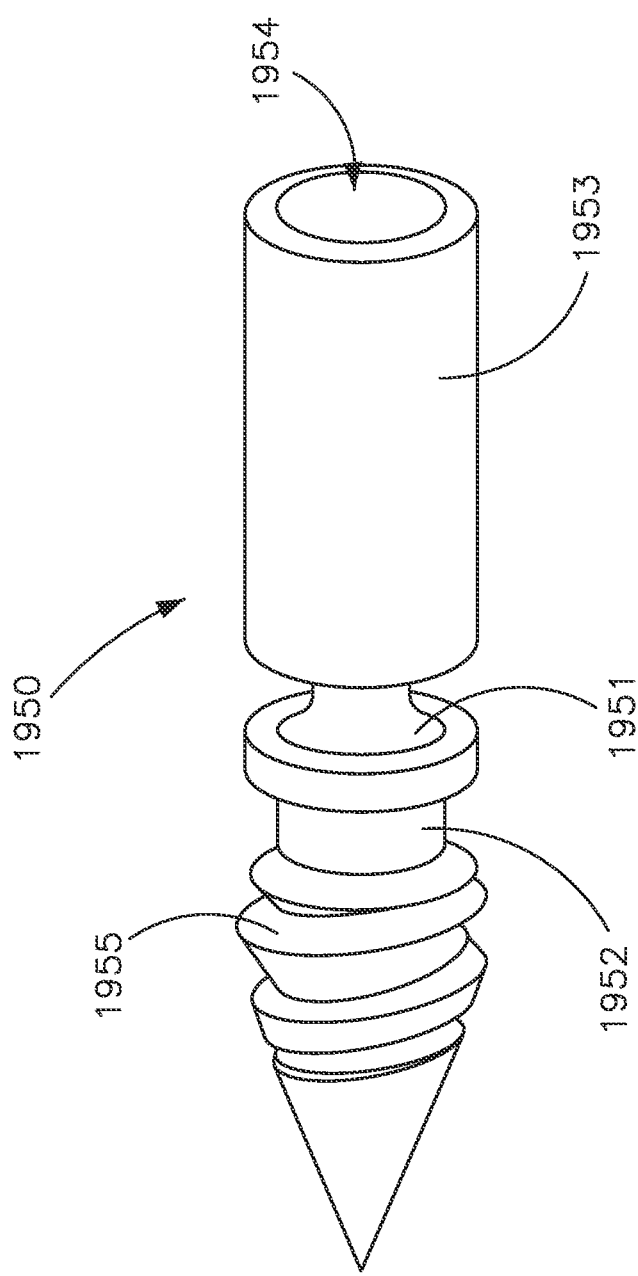
Figure 56D:
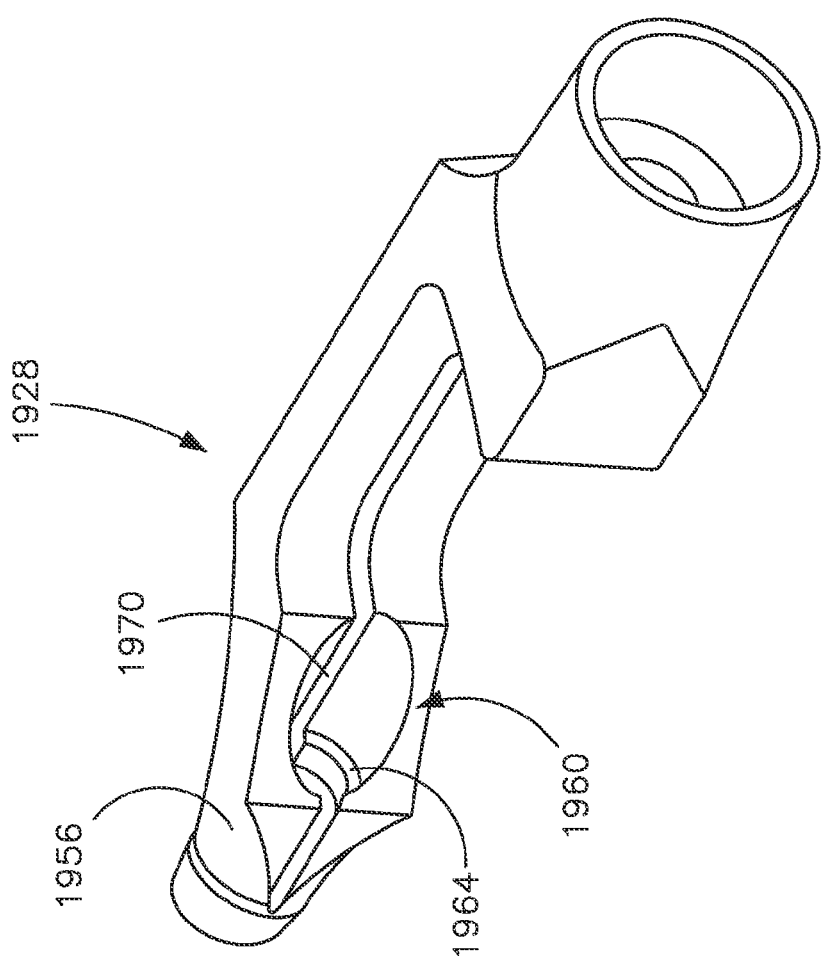
Figure 57C:
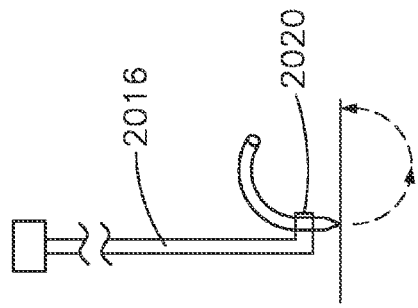
Figure 57E:
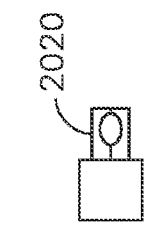
Figure 57B:
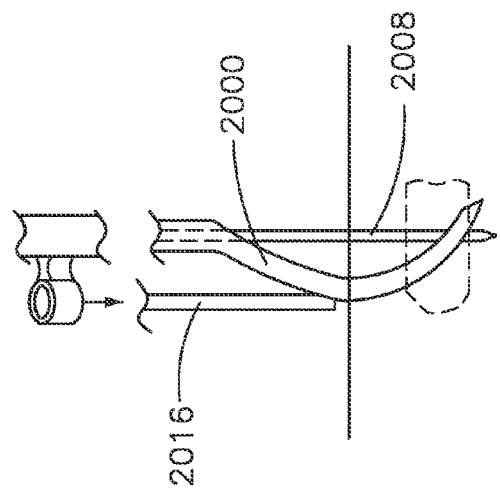
Figure 57D:
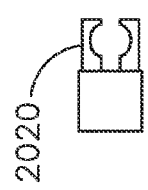
Figure 57A:
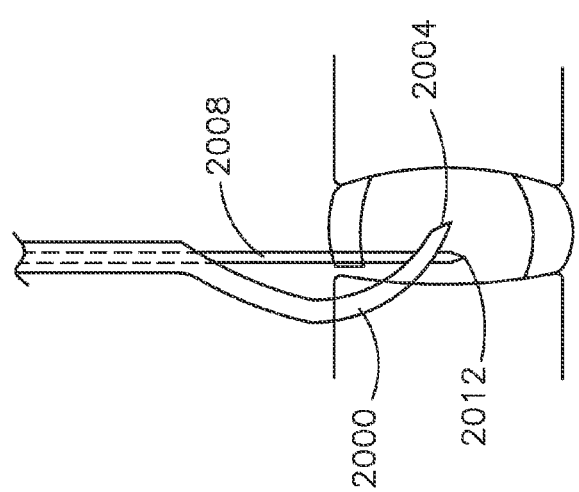
Figure 58A:
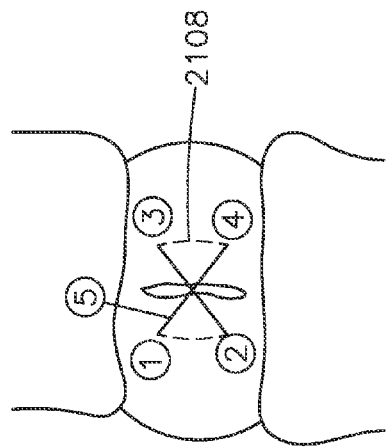
Figure 58D:
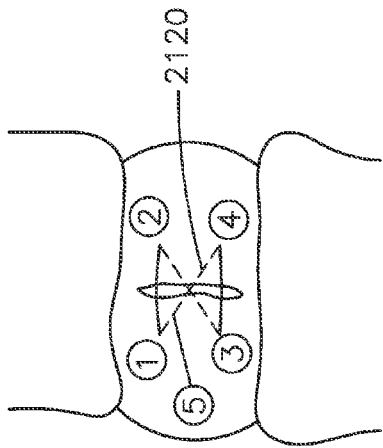
Figure 58B:
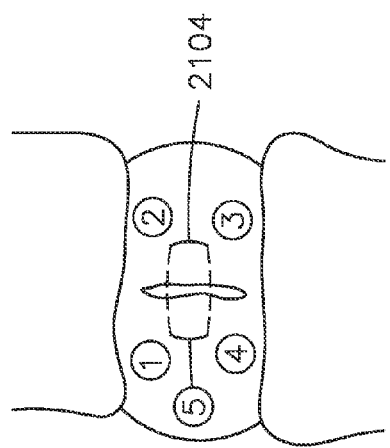
Figure 58E:
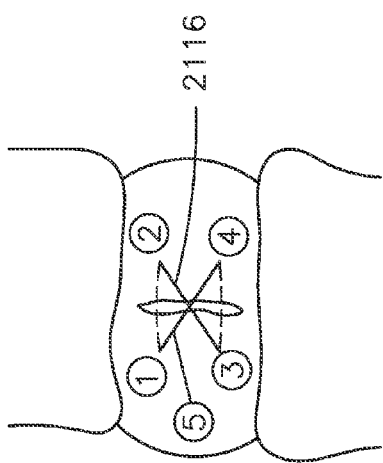
Figure 58C:
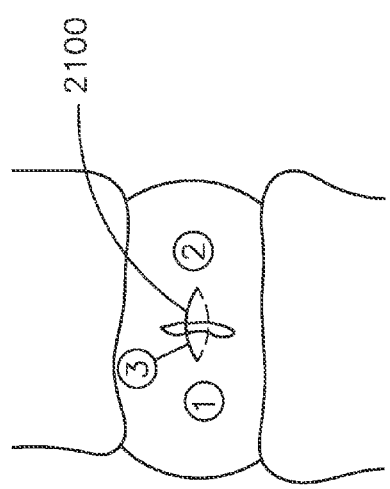
Figure 58F:
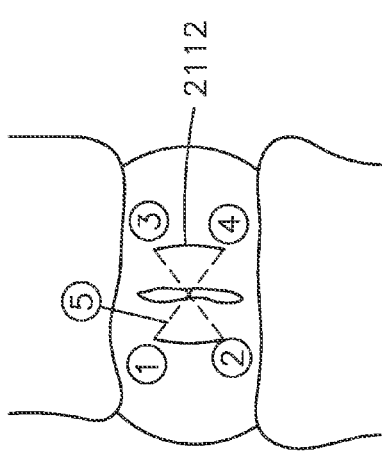

FIG. 41A is a partial side cross-sectional view of the instrument shown in FIG. 40A, with the spring loaded transverse beam configured to engage a recess formed in the shuttling element;

FIG. 41B is a partial side cross-sectional view of the instrument illustrated in FIG. 41A, showing the beam engaging the recess of the shuttling element;

FIG. 42A is a partial side cross-sectional view of another embodiment of the bi-directional suture passing instrument, in which a flexible polymer tube is used to retain the shuttling element in the boom arm housing;

FIG. 42B is a partial side cross-sectional view of the instrument illustrated in FIG. 42A, showing the flexible tube engaging a proximal edge of the shuttling element to thereby couple and retain the shuttling element within the boom arm housing;

FIG. 43A is a partial side cross-sectional view of the instrument illustrated in FIG. 42A, showing the flexible polymeric tube configured to engage a recess formed in the shuttling element;

FIG. 43B is a partial side cross-sectional view of the instrument illustrated in FIG. 43A, showing the tube engaging the recess of the shuttling element;

FIG. 44A is a partial side cross-sectional view of another embodiment of the bi-directional suture passing instrument, in which a C-clip is used to retain the shuttling element in the boom arm housing;

FIG. 44B is a partial side cross-sectional view of the instrument illustrated in FIG. 44A, showing the C-clip engaging a proximal edge of the shuttling element to thereby couple and retain the shuttling element within the boom arm housing;

FIG. 44C is a front plan view of the C-clip shown in FIG. 44A, in an unclipped position;

FIG. 44D is a front plan view of the C-clip shown in FIG. 44A, in a clipped position;

FIG. 45A is a partial side cross-sectional view of the instrument shown in FIG. 44A, with the C-clip configured to engage a recess formed in the shuttling element;

FIG. 45B is a partial side cross-sectional view of the instrument illustrated in FIG. 45A, showing the C-clip engaging the recess of the shuttling element;

FIG. 46A is a partial side cross-sectional view of another embodiment of the bi-directional suture passing instrument, in which a leaf spring finger is used to retain the shuttling element in the boom arm housing;

FIG. 46B is a partial side cross-sectional view of the instrument illustrated in FIG. 46A, showing the leaf spring finger engaging a proximal edge of the shuttling element to thereby couple and retain the shuttling element within the boom arm housing;

FIG. 47A is a partial side cross-sectional view of the instrument shown in FIG. 46A, with the leaf spring finger configured to engage a recess formed in the shuttling element;

FIG. 47B is a partial side cross-sectional view of the instrument illustrated in FIG. 47A, showing the finger engaging the recess of the shuttling element;

FIG. 48A is a partial side cross-sectional view of another embodiment of the bi-directional suture passing instrument, in which a wire buttress is used to retain the shuttling element in the boom arm housing;

FIG. 48B is a partial side cross-sectional view of the instrument illustrated in FIG. 48A, showing the wire buttress engaging a proximal edge of the shuttling element to thereby couple and retain the shuttling element within the boom arm housing;

FIG. 49A is a partial side cross-sectional view of the instrument shown in FIG. 48A, with the wire buttress configured to engage a recess formed in the shuttling element;

FIG. 49B is a partial side cross-sectional view of the instrument illustrated in FIG. 49A, showing the wire buttress engaging the recess of the shuttling element;

FIG. 50A is a partial perspective view of another embodiment of the bi-directional suture passing instrument, in which a spring loaded gate is used to retain the shuttling element in the boom arm housing;

FIG. 50B is a partial side cross-sectional view of the instrument illustrated in FIG. 50A, with the spring loaded gate configured to engage the proximal end of a shuttling element;

FIG. 51A is a partial top elevational view of another embodiment of the bi-directional suture passing instrument, in which a series of grooves and traps are used to detachably couple the needle to the shuttling element, and to detachably couple the shuttling element to the boom arm housing;

FIG. 51B is a partial top elevational view of the instrument illustrated in FIG. 51A, showing the needle and shuttling element engaging the boom arm housing;

FIG. 51C is a perspective view of the shuttling element utilized with the instrument illustrated in FIG. 51A;

FIG. 51D is a front view of the shuttling element shown in FIG. 51C;

FIG. 51E is a side view of the shuttling element shown in FIG. 51C;

FIG. 52A is a partial side perspective view of another embodiment of the bi-directional suture passing instrument, in which threaded features are used to detachably couple the needle to the shuttling element, and to detachably couple the shuttling element to the boom arm housing;

FIG. 52B is a partial bottom cross-sectional view of the instrument illustrated in FIG. 52A, showing the needle in a fully advanced position;

FIG. 52C is a partial perspective view of the instrument illustrated in FIG. 52A, showing the needle and shuttling element in a fully retracted position;

FIG. 52D is a partial perspective view of the instrument illustrated in FIG. 52C, showing the needle advanced into the boom arm housing;

FIG. 52E is a partial perspective view of the instrument illustrated in FIG. 52D, showing the needle and the shuttling element being rotated to thereby selectively couple the shuttling element to the boom arm housing;

FIG. 52F is a partial perspective view of the instrument illustrated in FIG. 52E, showing the needle being further rotated to decouple the needle from the shuttling element;

FIG. 52G is a partial perspective view of the instrument illustrated in FIG. 52F, showing the needle being retracted while the shuttling element remains coupled to the boom arm housing;

FIG. 52H is a partial perspective view of the instrument illustrated in FIG. 52G, showing the needle in a fully retracted position;

FIG. 52I is a partial perspective view of the instrument illustrated in FIG. 52H, showing the needle being advanced into the boom arm housing;

FIG. 52J is a partial perspective view of the instrument illustrated in FIG. 52I, showing the needle being rotated to thereby couple the needle to the shuttling element;

FIG. 52K is a partial perspective view of the instrument illustrated in FIG. 52J, showing the needle and the shuttling element being rotated to thereby decouple the shuttling element from the boom arm housing;

FIG. 52L is a partial perspective view of the instrument illustrated in FIG. 52K, showing the needle and the shuttling element being retracted from the boom arm housing;

FIG. 53A is a partial cross-sectional view of another embodiment of the bi-directional suture passing instrument, in which the needle has external threads and the shuttling element has internal threads to detachably couple the needle to the shuttling element;

FIG. 53B is a partial cross-sectional view of the instrument illustrated in FIG. 53A, showing the needle and shuttling element in a fully advanced position;

FIG. 53C is a partial cross-sectional view of the instrument illustrated in FIG. 53B, showing the needle in a fully retracted position, and the shuttling element coupled to the boom arm housing;

FIG. 54A is a top side elevational view of a needle having wings;

FIG. 54B is a left side elevational view of the needle shown in FIG. 54A;

FIG. 54C is a top side elevational view of a shuttling element that is configured to be detachably coupled to the needle shown in FIG. 54A;

FIG. 54D is a left side elevational view of the shuttling element shown in FIG. 54C;

FIG. 54E is a back side plan view of the shuttling element shown in FIG. 54D;

FIG. 54F is a top side elevational view of a boom arm housing that is configured to receive the shuttling element shown in FIG. 54C;

FIG. 54G is a left side elevational view of the boom arm housing shown in FIG. 54F;

FIG. 54H is a back side plan view of the boom arm housing shown in FIG. 54G;

FIG. 54I is a partial top elevational view of the instrument illustrated in FIGS. 54A-54H, showing the needle and shuttling element in a fully retracted position;

FIG. 54J is a partial top elevational view of the instrument illustrated in FIG. 54I, showing the needle and shuttling element advanced into the boom arm housing;

FIG. 54K is a partial top elevational view of the instrument illustrated in FIG. 54J, showing the needle and the shuttling element being rotated to thereby selectively couple the shuttling element to the boom arm housing;

FIG. 54L is a partial top elevational view of the instrument illustrated in FIG. 54K, showing the needle being retracted while the shuttling element remains coupled to the boom arm housing;

FIG. 54M is a partial top elevational view of the instrument illustrated in FIG. 54L, showing the needle advanced into the shuttling element;

FIG. 54N is a partial top elevational view of the instrument illustrated in FIG. 54M, showing the needle and shuttling element being rotated to decouple the shuttling element from the boom arm housing;

FIG. 55 is a perspective view of another embodiment of the bi-directional suture passing instrument that is similar to the instrument shown in FIGS. 54A-54N, except that the structures defining the engagement features on the needle and the shuttling element are reversed;

FIG. 56A is a side perspective view of another embodiment of the bi-directional suture passing instrument, showing additional features that may be used;

FIG. 56B is a front perspective view of a driver that may be used with the instrument shown in FIG. 56A;

FIG. 56C is a side perspective view of a shuttling element that may be used with the instrument shown in FIG. 56A;

FIG. 56D is a rear perspective view of a boom arm that may be used with the instrument shown in FIG. 56A;

FIG. 57A is a side elevational view of another embodiment of the bi-directional suture passing instrument, configured to create a pathway in a bony structure through which the suture can be passed;

FIG. 57B is a side elevational view of the instrument shown in FIG. 57A, having an impact rod;

FIG. 57C is a side elevational view of the instrument shown in FIG. 57A, having an impact rod configured to grab the needle;

FIG. 57D is a front plan view of a grip associated with the impact rod shown in FIG. 57C;

FIG. 57E is a front plan view of the grip shown in FIG. 57D in a closed position;

FIG. 58A is a side elevational view of a simple stitch;

FIG. 58B is a side elevational view of a horizontal box mattress stitch;

FIG. 58C is a side elevational view of a horizontal mattress stitch;

FIG. 58D is a side elevational view of a reverse horizontal mattress stitch;

FIG. 58E is a side elevational view of a vertical mattress stitch;

FIG. 58F is a side elevational view of a reverse vertical mattress stitch; and

Figure 58I:
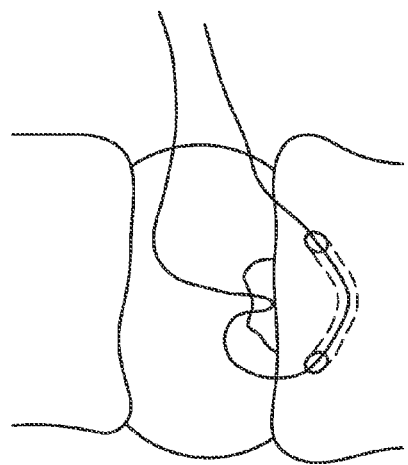
Figure 58H:
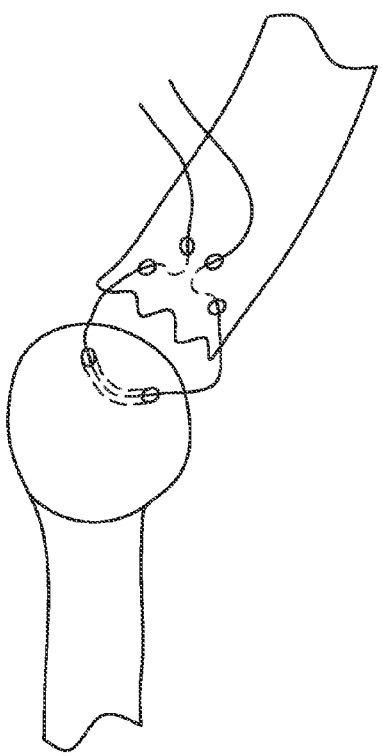
Figure 58G:
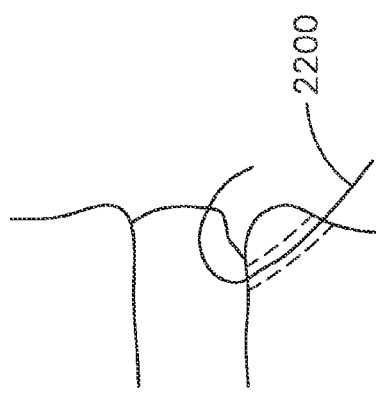

FIGS. 58G-58I are side elevational views of a suturing method for soft tissue repair near a bony element.

DETAILED DESCRIPTION OF ILLUSTRATIVE EMBODIMENTS

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the patient's body, or the geometric center of the suture passer instrument and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

Referring to FIGS. 1A-1C a bi-directional suture passing instrument 10 extends in a longitudinal direction L, and includes a proximal end P and a distal end D. As shown, the instrument 10 includes a handle 14, an elongated body 18 coupled to the handle 14, and a boom arm 22 coupled to the distal end of the elongated body 18. The boom arm 22 includes an arm 190 that is coupled to the distal end of the elongated body 18 and carries a boom arm housing 198, so as to define a tissue-receiving gap 202 between the elongated body 18 and the boom arm housing 198. The instrument 10 further includes, an actuator element 26, a needle 34 coupled to the distal end of the actuator element 26, and a grip 30 that is coupled to the proximal end of the actuator element 26. The actuator element 26 and the needle 34 are reciprocally translatable between a retracted (rearward) position and an extended or advanced (forward) position, within both the interior of the handle 14 and the interior of the elongated body 18. The instrument 10 further includes a needle like shuttling element 40 that is configured to carry a strand of suture to be inserted through a tissue defect, and the boom arm housing

198. As will be described in more detail below, when the shuttling element 40 is coupled to the needle 34, the shuttling element 40 may pass through a tissue defect. Once the shuttling element 40 has passed through the tissue defect, the shuttling element 40 may be detachably coupled to the boom arm housing 198.

Figure 2D:
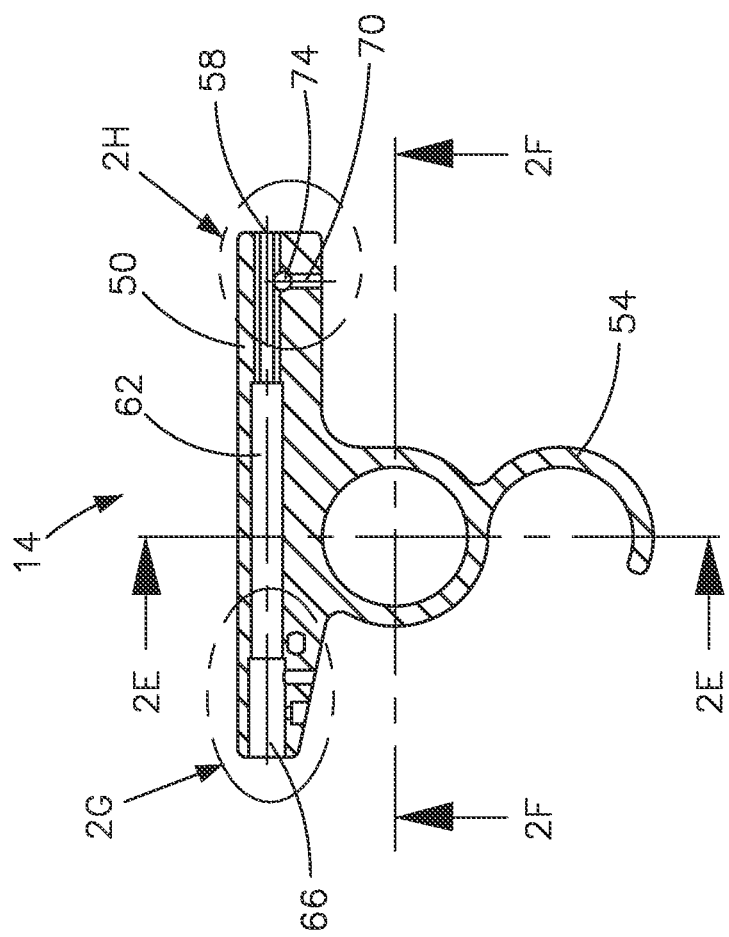
FIG. 2D is a side cross-sectional view of the handle, taken along line 2D-2D of FIG. 2C.
Figure 2E:
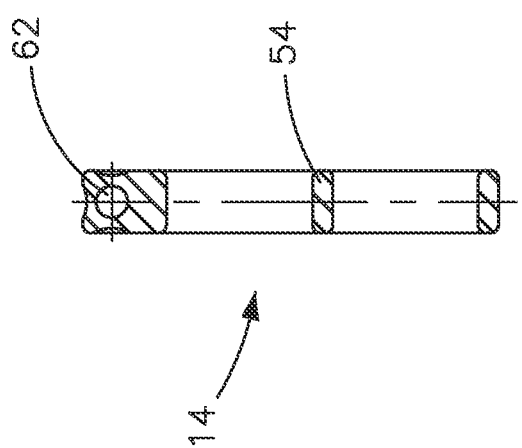
FIG. 2E is a front cross-sectional view of the handle, taken along line 2E-2E of FIG. 2D.
Figure 2G:
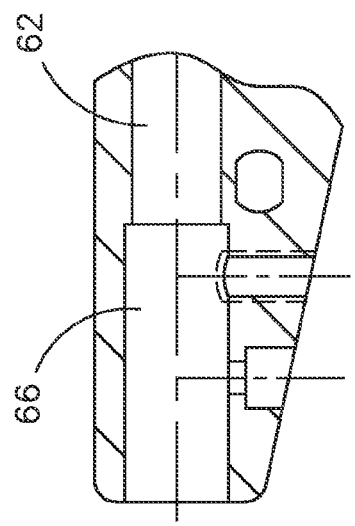
FIG. 2G is a side cross-sectional view of the handle taken from within oval 2G of FIG. 2D.

As shown in FIGS. 1A-1B, and 2A-2H, the handle 14 includes a body 50 having a grip 54 extending down from a bottom surface of the body 50. The body 50 is generally elongated and rectangular in shape. As shown in FIG. 2D, a first sized bore 58 extends distally, along the longitudinal direction L, through the body 50 from the proximal end of the body 50, and into a second sized bore 62. Second bore 62 continues to extend distally into a third sized bore 66, that extends through the distal end of the body 50. Each bore 58, 62, and 66 is sized to accommodate certain parts of the instrument 10. For example, actuator element 26 is translatable within bore 58, needle 34 is translatable within bore 62, and body member 18 is secured within bore 66.

Figure 2H:
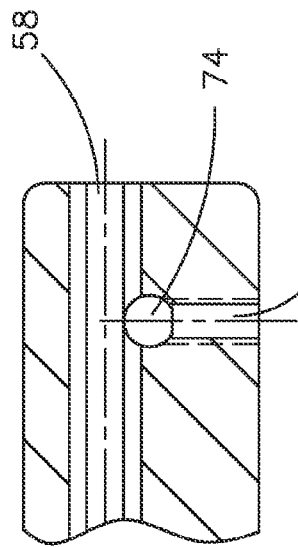
FIG. 2H is a side cross-sectional view of the handle taken from within oval 2H of FIG. 2D.
Figure 2F:
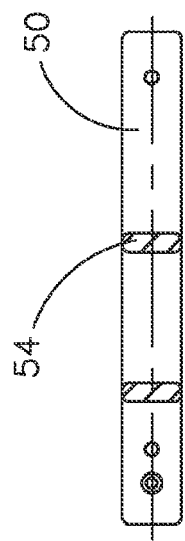
FIG. 2F is a bottom cross-sectional view of the handle, taken along line 2F-2F of FIG. 2D.

In accordance with the illustrated embodiment, the first bore 58 is generally cylindrical and is capable of receiving the actuator element 26, as shown in FIG. 1B. In particular, the actuator element 26 is reciprocally translatable within the first bore 58. Referring to FIGS. 2D and 2H, a fourth bore 70 extends transverse to the longitudinal direction L, through the bottom surface of the body 50 and into the first bore 58. As shown, the fourth bore 70 contains a mating feature, such as ball plunger 74 that is adapted to engage either directly or indirectly the actuator element 26.

As shown in FIGS. 3A-3D, the actuator element 26 includes a cylindrical body 76 having a first coupling element 78 at its distal end, and a second coupling element 82 at its proximal end. The body 76 of the actuator element 26 defines a mating feature, such as detent 86 that is configured to be engaged by a protrusion extending from a lock. The first coupling element 78 is configured to attach the actuator element 26 to the needle 34, and the second coupling element 82 is configured to attach the actuator element 26 to the thumb ring 30. Therefore, as the actuator element 26 is translated by the user, the needle 34 will be translated.

As shown in FIGS. 4A-4C, the grip 30 may be a thumb ring that includes a body 98 having a bore 102 extending proximally into the body 98. The bore 102 is adapted to receive the second coupling element 82 of the actuator element 26. The body 98 defines a ring 106 that is capable of receiving a user's thumb, so that the user may easily apply a force to the thumb ring 30, to thereby cause the actuator element 26, and thus the needle 34 to translate forward or backward.

To limit the travel of the actuator element 26 and the needle 34, the suture passer 10 includes an actuator stop 110. As shown in FIGS. 1B, and 5A-5C, the actuator stop 110 is a generally cylindrical body 114 disposed in the second bore 62 of the handle 14. As shown in FIGS. 5A-5C, the body 114 of the actuator stop 110 includes an irregular shaped bore 118 for receiving and attaching to the needle 34. Irregular shaped means any shape, excluding a perfect cylinder.

The body 114 of the actuator stop 110 also defines two mating features, such as detents 122 formed in its outer surface for receiving a corresponding mating feature such as a ball plunger that may be disposed in the handle 14. As shown, the detents 122 are radially separated 90 degrees from each other with respect to a longitudinal axis of the actuator stop 110. The detents 122 are configured to receive a ball plunger 126 disposed in the handle 14 to limit or control the rotation of the needle 34, for embodiments of the instrument 10 that require rotation of the needle 34. Thus, the rotation of the needle 34 is limited to 90 degrees. It should be understood, that the actuator stop 110 is not limited to such a design, and that other designs are envisioned. For example, the actuator stop 110 may be embodied by a narrowing of the second bore 62 of the handle 14. In such a case, the narrowing portion will be configured to contact the distal end of the actuator element 26 near the coupling of the actuator 26 to the needle 34 upon a given translational value of the actuator 26 with respect to the handle 14.

Figure 7B:
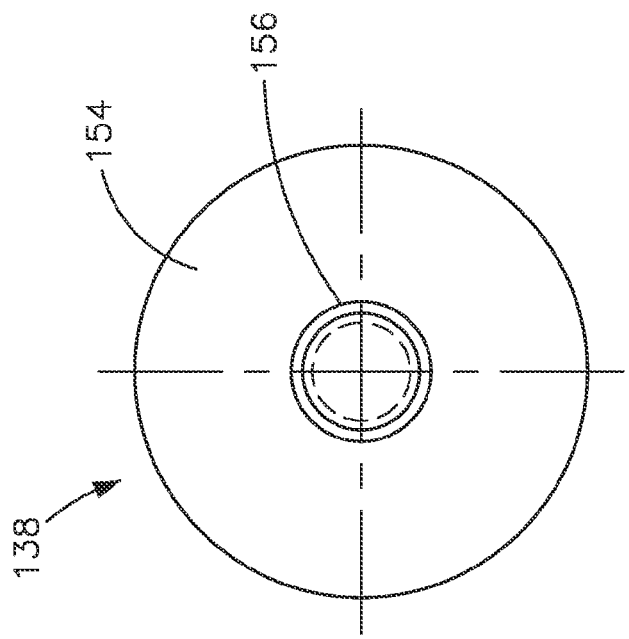
FIG. 7B is a side elevational view of a thumb ring lock cap element shown in FIG. 7A.
Figure 7A:
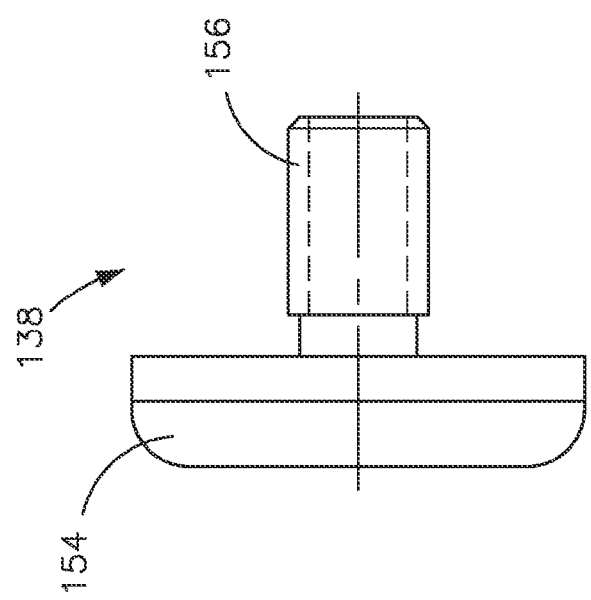
FIG. 7A is a top plan view of a thumb ring lock cap element of the instrument shown in FIGS. 1A-1B.
Figure 8C:
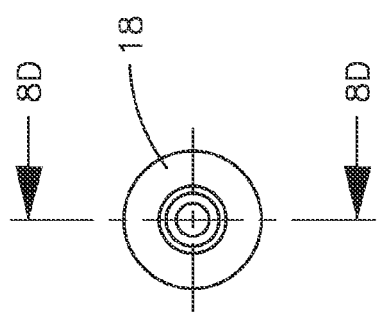
FIG. 8C is a front elevational view of the body element shown in FIG. 8A.
Figure 8D:
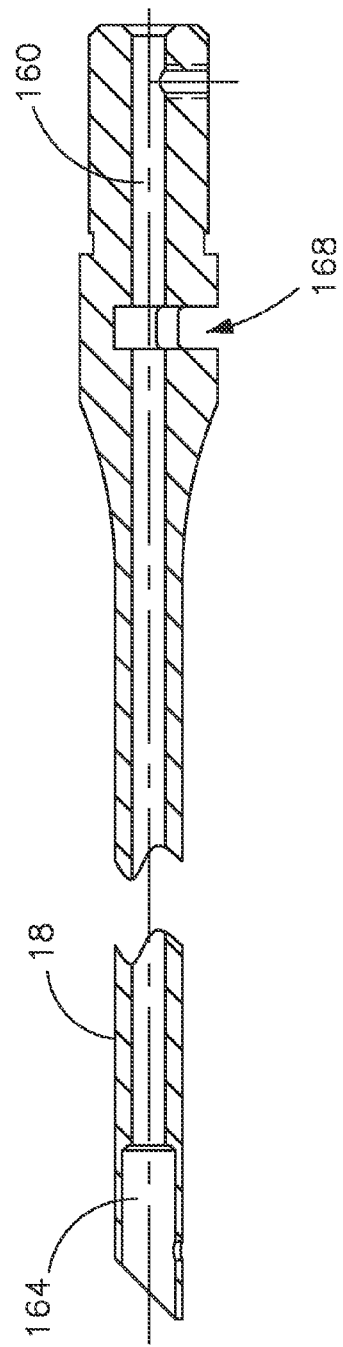
FIG. 8D is a side cross-sectional view of the body element shown in FIG. 8C, taken along the line 8D-8D.
Figure 10A:
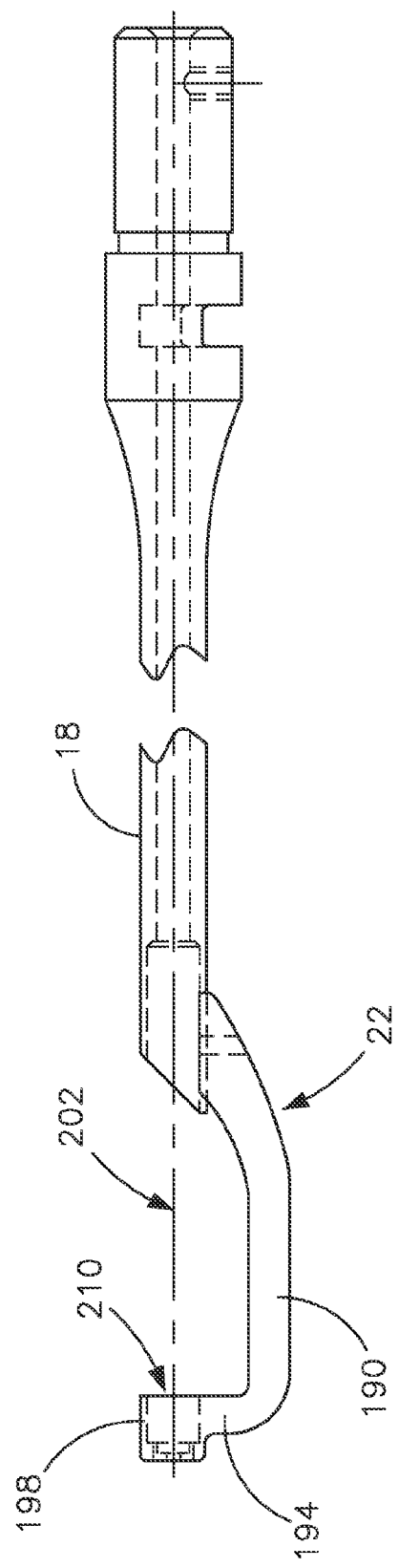
FIG. 10A is a fragmented side elevational view of the instrument shown in FIG. 1A detailing the boom arm at its distal end.
Figure 10E:
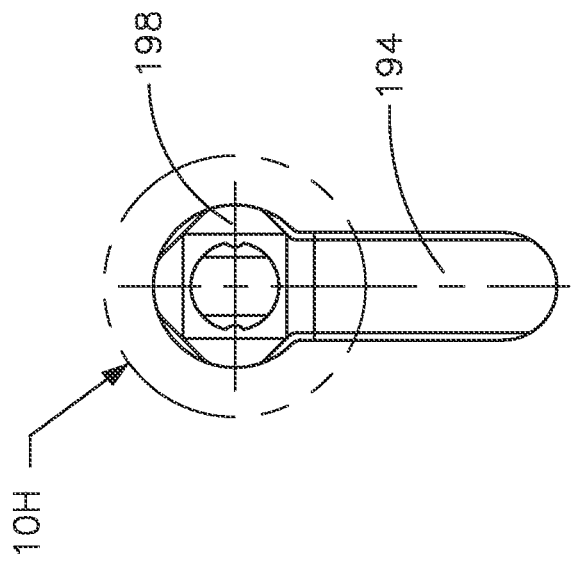
FIG. 10E is a front elevational view of the boom arm shown in FIG. 10A.
Figure 10D:
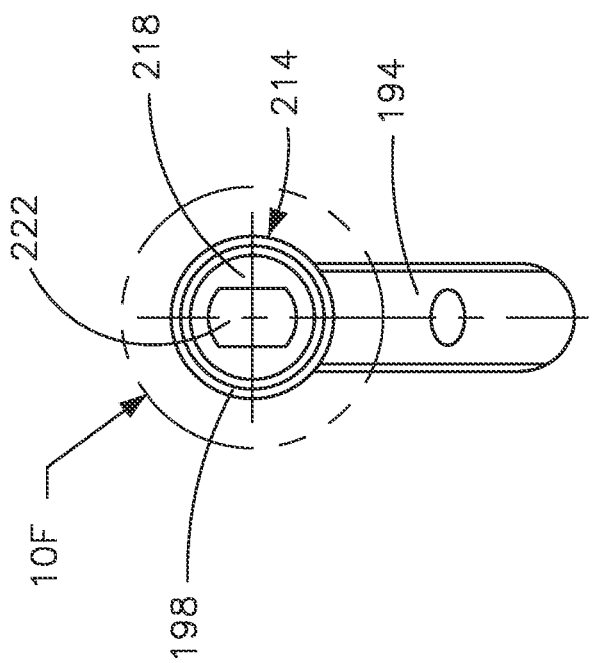
FIG. 10D is a rear elevational view of the boom arm shown in FIG. 10A.
Figure 10H:
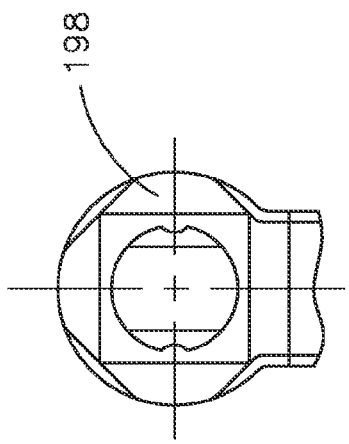
FIG. 10H is an enlarged front view taken from within oval 10H of FIG. 10E.
Figure 10G:
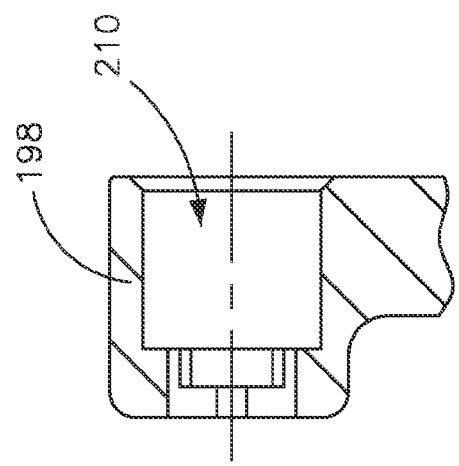
FIG. 10G is a side cross-sectional view taken from within oval 10G of FIG. 10C.
Figure 10F:
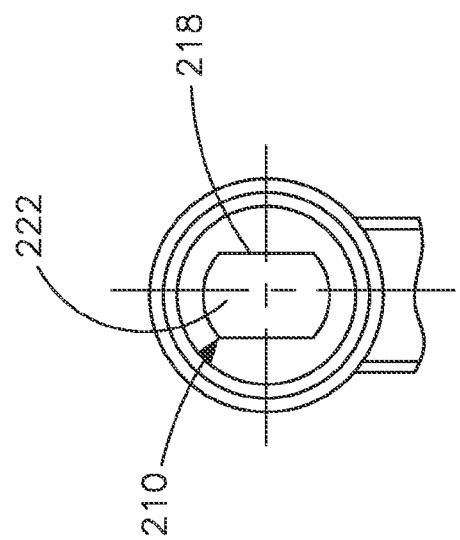
FIG. 10F is an enlarged rear view taken from within oval 10F of FIG. 10D.
Figure 12E:
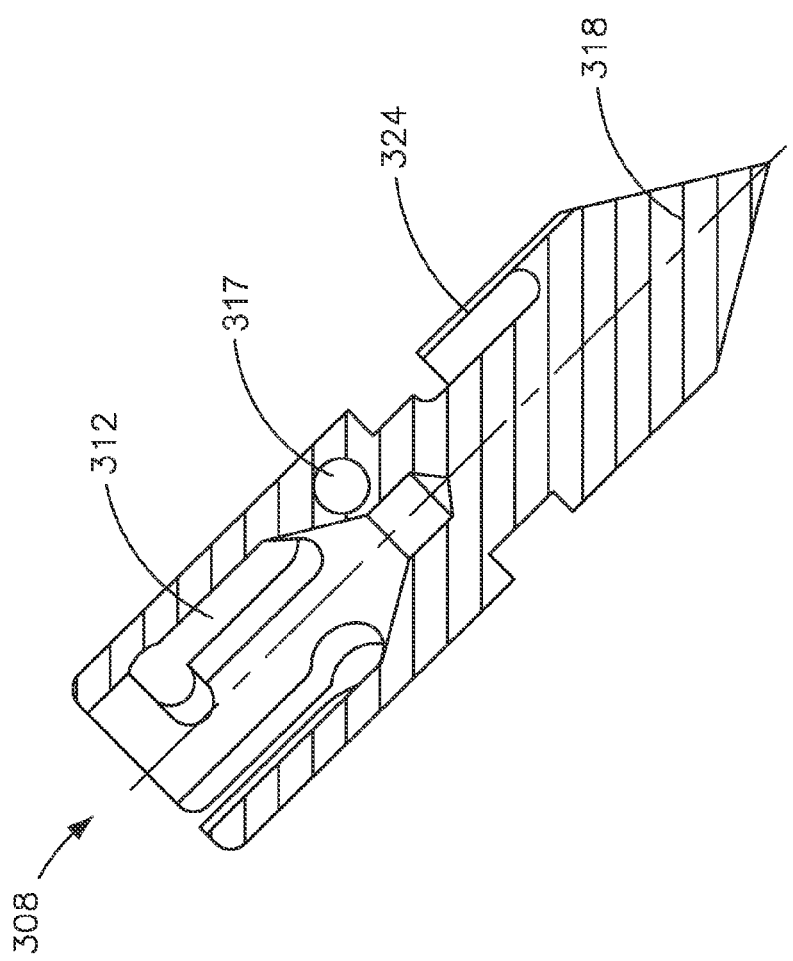
FIG. 12E is a side cross-sectional view of the shuttling element shown FIG. 12C, taken along line 12E-12E.

The suture passer 10 may include a lock 130 that is operable to fix the longitudinal position of the actuator 26, and thus the needle 34, such that the actuator 26 and the needle 34 are no longer able to translate when locked. The lock 130 includes a locking element 134, as shown in FIGS. 6A and 6B, and a locking cap 138, as shown in FIGS. 7A and 7B that interacts with the locking element 134 so as to fix the position of the locking element 134. Referring to FIGS. 6A and 6B the locking element 134 includes a head 142 and a body 146 extending from the head 142. The body 146 defines two large detents 148, three small detents 150, and a bore 152 extending into an end of the body 146. The body also defines a protrusion 153 that extends between the two large detents 148. When the locking element 134 is positioned such that the actuator is received into one of the large detents 148, the ball plunger 74 contained within the fourth bore 70 of the handle will engage one of the outer smaller detents 150, and the actuator 26 will be capable of translating forward and backward. However, when the ball plunger 74 contained within the fourth bore 70 of the handle engages the center smaller detent 150, the locking element 134 is positioned such that protrusion 153 engages the detent 86 of the actuator 26, and the actuator 26 will not be capable of movement, thereby locking the actuator 26 and needle 34 in place.

The locking cap 138 is configured to engage the bore 152 of the locking element 134. As shown in FIGS. 7A and 7B, the locking cap 138 includes a head 154 and a body 156 extending from the head 154. The body 156 is cylindrical and is configured to engage the bore 152 of the locking element 134. When the body 156 of the locking cap 138 is engaging the bore 152 of the locking element 134, the position of the locking element will be fixed.

As shown in FIGS. 1A, and 8A-8D, the body member 18 is longitudinally elongated, and defines a channel 160 that longitudinally extends through the entire length of the body member 18. As shown in FIG. 1B, the needle 34 is translatable within the channel 160 of the body member 18. The channel 160 includes a first channel portion and a second channel portion 164 that is disposed distal of the first channel portion and has a larger diameter than the first channel portion. The channel 160 can be sized to accommodate the needle 34 so that the needle 34 can reciprocate between an extended or advanced (forward) position and a retracted (rearward) position. The second channel portion 164 preferably has a larger diameter than the first channel portion. The larger second channel portion 164 is thus capable of receiving the shuttling element 40 when the needle 34 is in a retracted position, to thereby act as a sheath for the needle and shuttling element.

As shown in FIGS. 1A, 8A-8B, and 9A-9D, the body member 18 further defines an actuator slot 168 extending through the outer surface in a direction generally transverse to the channel 160. The actuator slot 168 extends into the first channel section of the channel 160 at the proximal end of the body member 18. The suture passing instrument 10 includes a tip actuator 180 that is configured to actuate the needle 34 to thereby couple or decouple the shuttling element 40 to the needle 34. As shown in FIGS. 1A, and 9A-9D, the tip actuator 180 extends through the actuator slot 168, and is attached to the needle 34. In particular, the tip actuator 180 includes a keyed bore 188 that receives the needle 34 at a location whereby the needle 34 includes a similarly keyed cross section, such that the tip actuator 180 is rotatably coupled to the primary needle 34. The tip actuator 180 extends out from the body member 18, and can be engaged by a user so as to rotate the needle 34 through a 90 degree angle range about the longitudinal axis L of the instrument 10 between a locked position and an unlocked position. When in the locked position, the shuttling element 40 is coupled to the boom arm housing 198. When in the unlocked position, the shuttling element 40 is disengaged from the boom arm housing 198. The tip actuator 180 also includes indicia 189 indicating the position of the needle tip. The indicia may state "tip unlocked" as shown in FIG. 9C or "tip locked" as shown in FIG. 9D. It should be understood, however, that in other embodiments of the instrument 10, the shuttling element 40 can be detachably coupled to the boom arm housing 198 through translation or actuation of an engagement feature or other like structure, as opposed to rotation of the tip actuator 180. Therefore, it will be appreciated that the tip actuator 180 may also be configured to enable translation of an engagement feature or other like structure.

As shown in FIGS. 1A-1B, and 10A-10H, the boom arm 22 extends from the elongated body 18. In particular, the boom arm 22 includes an arm 190 that is coupled to a distal end of the elongated body member 18 and extends distally to a boom arm housing 198. The boom arm housing 198 extends generally perpendicularly out from the distal end of the boom arm 22, and is configured to receive the shuttling element 40. It can thus be said that the boom arm 22 includes a boom arm housing 198 supported at the distal end of the boom arm 22. A tissue-receiving gap 202 is disposed between the boom arm housing 198 and the distal end of the elongated body 18. The tissue receiving gap 202 is configured to receive a piece of tissue having a tissue defect, such as a laceration, that is to be repaired by the suturing instrument 10.

The boom arm housing 198 defines a cylindrical or alternatively shaped channel or bore 210 that is aligned with the channel 160 formed in the body member 18. The boom arm housing 198 includes a locking interface 214 configured to selectively detachably couple the shuttling element 40 within the boom arm housing 198 when the shuttling element 40 is to be retained within the boom arm housing 198. As shown, the locking interface 214 may be a flange 218 extending from an internal surface of the housing 198 that defines a slot shaped opening 222 into the housing 198.

As shown in FIGS. 11A-11E, the primary needle 34 includes an elongated shaft 230, and a needle element 234 extending from a distal end of the shaft 230. As shown in FIGS. 11A-B, the shaft 230 is generally cylindrical, and includes a keyed portion 238 that corresponds in shape to the keyed bore 188 of the tip actuator 180. The keyed portion 238 of the shaft 230 is aligned with the actuator slot 168. Accordingly, the keyed portion 238 is disposed at the location the actuator stop 110 and the tip actuator 180 are connected to the primary needle 34, and thus extends through the keyed bore 188 of the tip actuator 180. As a result, as the tip actuator 180 is rotated by a user, the needle 34 will also be rotated in the manner described above. The needle 34 further includes a coupling element 242 that extends rearward from the shaft 230, and is configured to attach the actuator element 26 to the primary needle 34. The coupling element 242 may be a hex or head portion that allows rotation of the needle 34 with respect to the actuator element 26. Thus, the needle 34 may be rotated, while the actuator element remains stationary.

As shown in FIGS. 11D and 11E, the needle element 234 includes a cylindrical body 246 having a needle tip 250 and an engagement feature 252 defined by two fins 254 that extend radially outward from the cylindrical body 246. Each fin 254 includes an angled front surface 258 and an angled rear surface 262. The angled surfaces 258 and 262 allow the fins 254 and thus the needle element 234 to more easily engage and snap into and out of the shuttling element 40.

As shown in FIGS. 12A-12E the shuttling element 40 includes a needle engaging portion 300, and a tissue engaging portion 304 extending forward of the needle engaging portion 300. The needle engaging portion 300 is configured to couple to the needle element 234 of the needle 34. In accordance with the illustrated embodiment, the needle engaging portion 300 defines a bore 308 that is configured to receive the needle element 234 of the needle 34. Grooves 312 are formed in the needle engaging portion 300 and extend into the bore 308. Grooves 312 form an engagement feature 314 that correspond to the engagement feature 252 of the needle 34. Thus, grooves 312 are configured to receive the fins 254 of the needle 34 to thereby detachably couple the needle 34 to the shuttling element 40. Forward of the grooves 312 is a bore 317 for securely holding an end of the suture. The bi-directional suture instrument 10 may come preassembled with the suture secured to the shuttling element 40 or the instrument 10 may be provided with a plurality of shuttling elements 40, each with a strand of suture secured thereto.

The tissue engaging portion 304 is oblong and is shaped to be received by the slot shaped opening 222 of the boom arm housing 198. As shown, the tissue engaging portion 304 includes a needle-like tip 318 and a locking mechanism 320. The locking mechanism 320 is a protrusion 324 that defines a recess 328 in the tissue engaging portion 304. The locking mechanism 320 is configured to lockingly engage the locking interface 214 formed in the boom arm housing 198. Thus, the shuttling element 40 may carry a suture through tissue, be locked and retained in the boom arm housing 198, and at a later time be reattached to the needle, to carry the suture back through the tissue.

Figure 13:
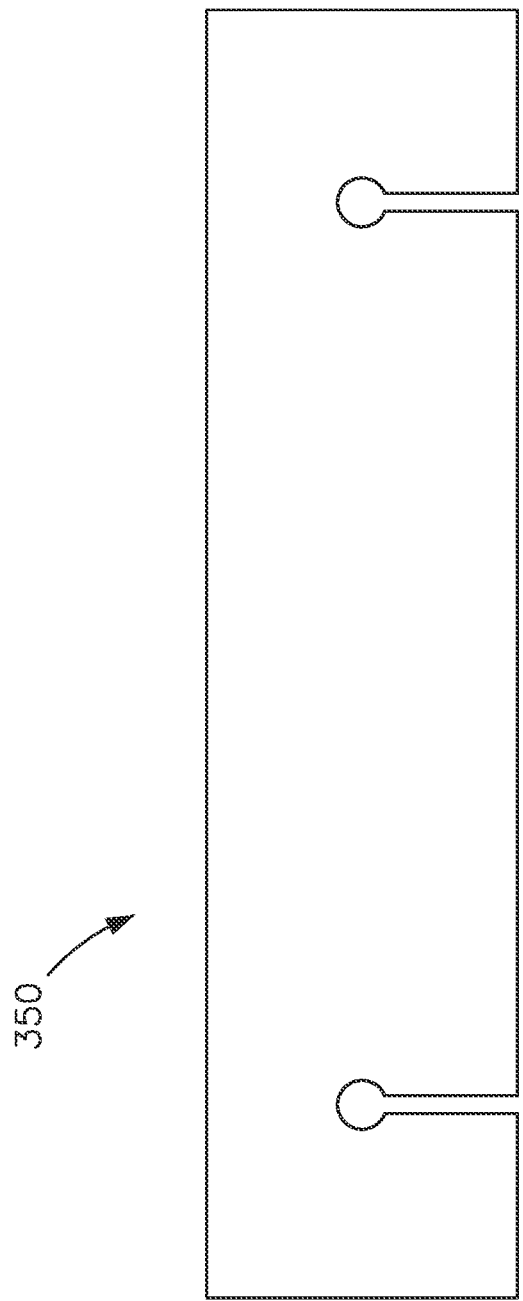
FIG. 13 is a top plan view of a suture tensioner element of the instrument shown in FIGS. 1A-1B.

To maintain tension in the suture strand, the suture instrument 10 may include a suture tensioner 350 coupled to the handle 14. As shown in FIGS. 1A, and 13, the suture tensioner 350 may be configured to hold and secure a loose end of suture material and maintain tension in the suture strand, thereby allowing the suture strand to be drawn through the suture tensioner element 350 under tension. The suture tensioner 350 is configured to hold and secure suture material on either side of the handle 14 and may be disposed through the handle 14 or may be embodied by two suture tensioner elements 350, one disposed on either side of the handle 14. The tensioner 350 includes two slots, one on either side of the handle 14, and the strand of suture is passed through one of the two slots to hold the strand in tension.

Figure 14A:
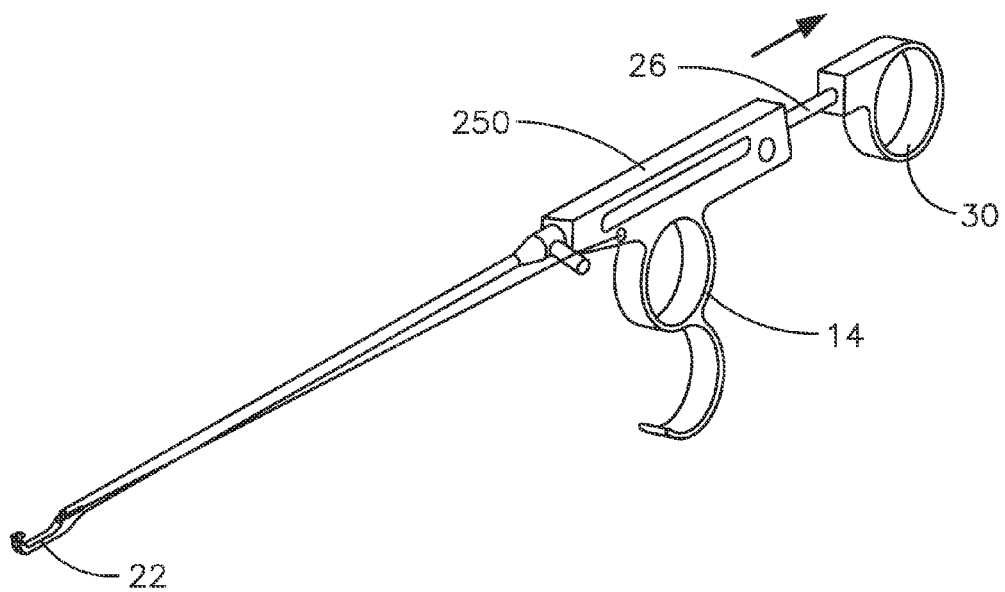
FIG. 14A is a side perspective view of the bidirectional suture passing instrument illustrated in FIGS. 1A-1B, showing the needle in a retracted position and the shuttling element coupled to the needle.
Figure 14B:
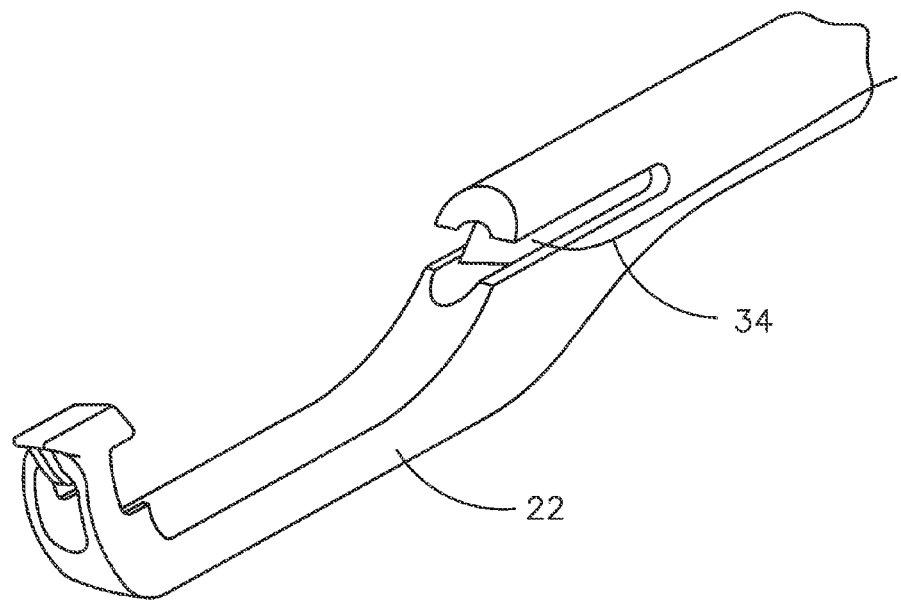
FIG. 14B is an enlarged side perspective view of a distal end of the instrument shown in FIG. 14A.
Figure 14C:
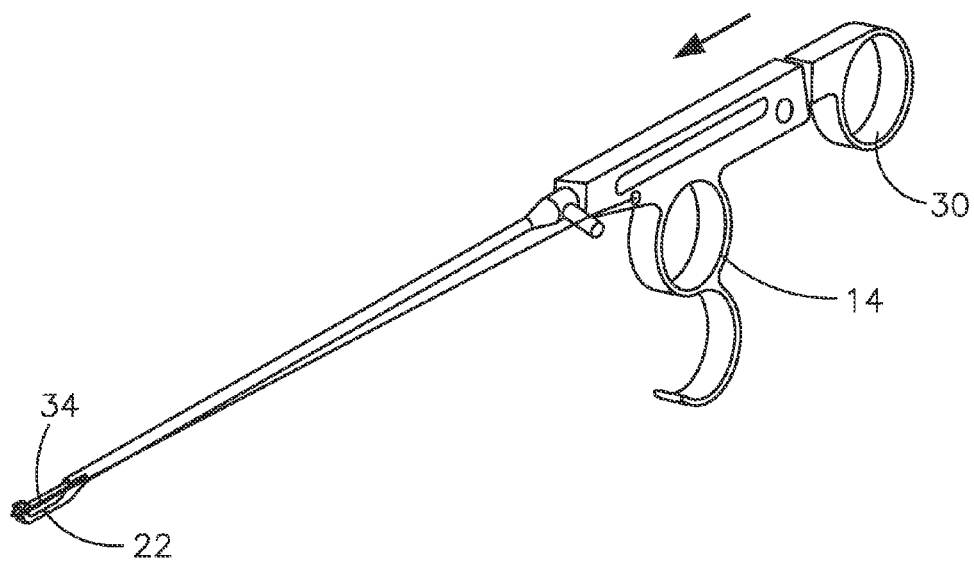
FIG. 14C is a side perspective view of the instrument shown in FIG. 14A, showing the needle in an advanced position and the shuttling element coupled to the needle.
Figure 14D:
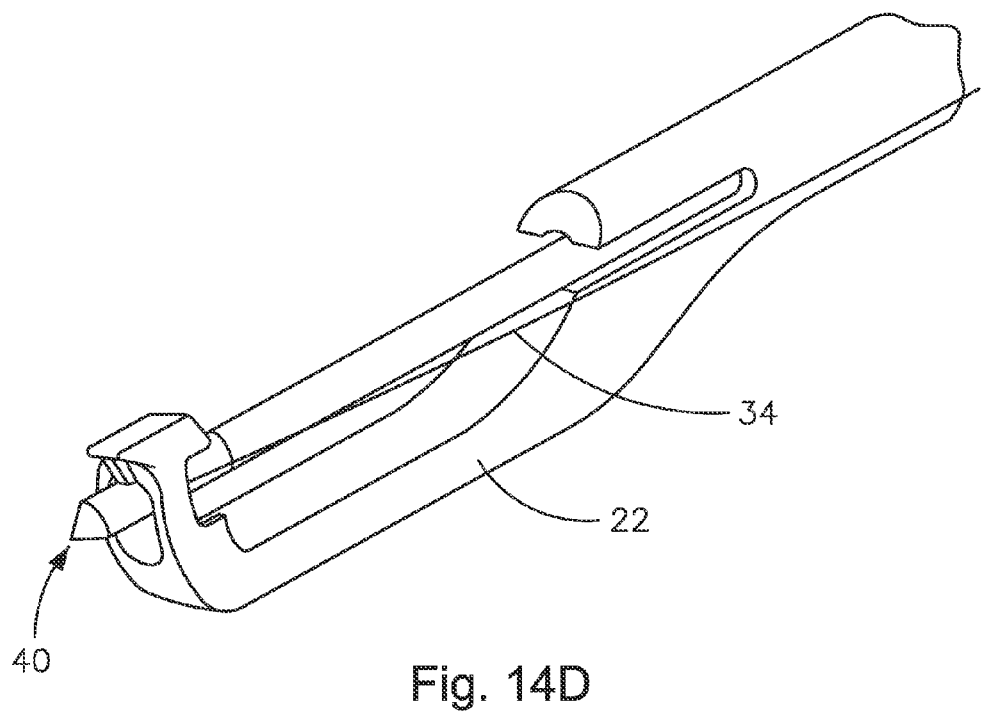
FIG. 14D is an enlarged side perspective view of the distal end of the instrument shown in FIG. 14C.
Figure 14E:
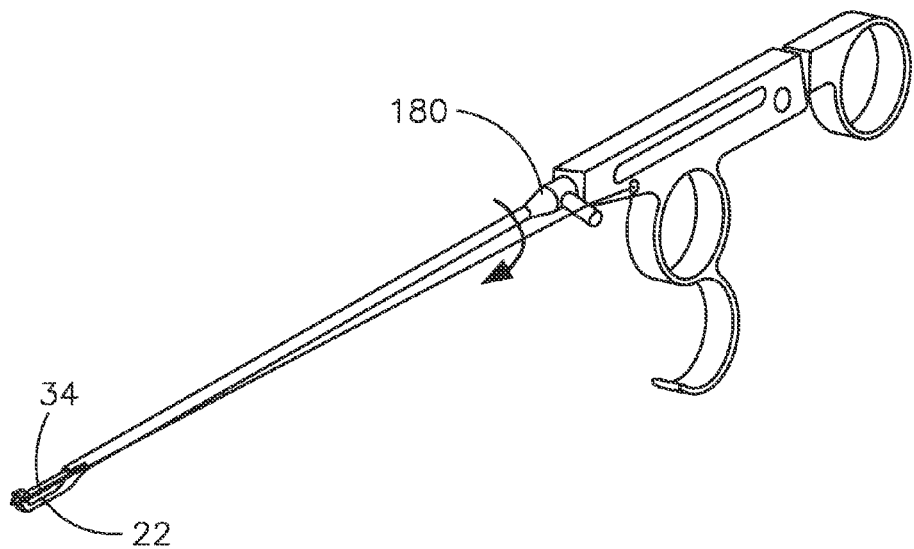
FIG. 14E is a side perspective view of the instrument shown in FIG. 14A, showing the needle in an advanced position and the shuttling element coupled to the boom arm.
Figure 14F:
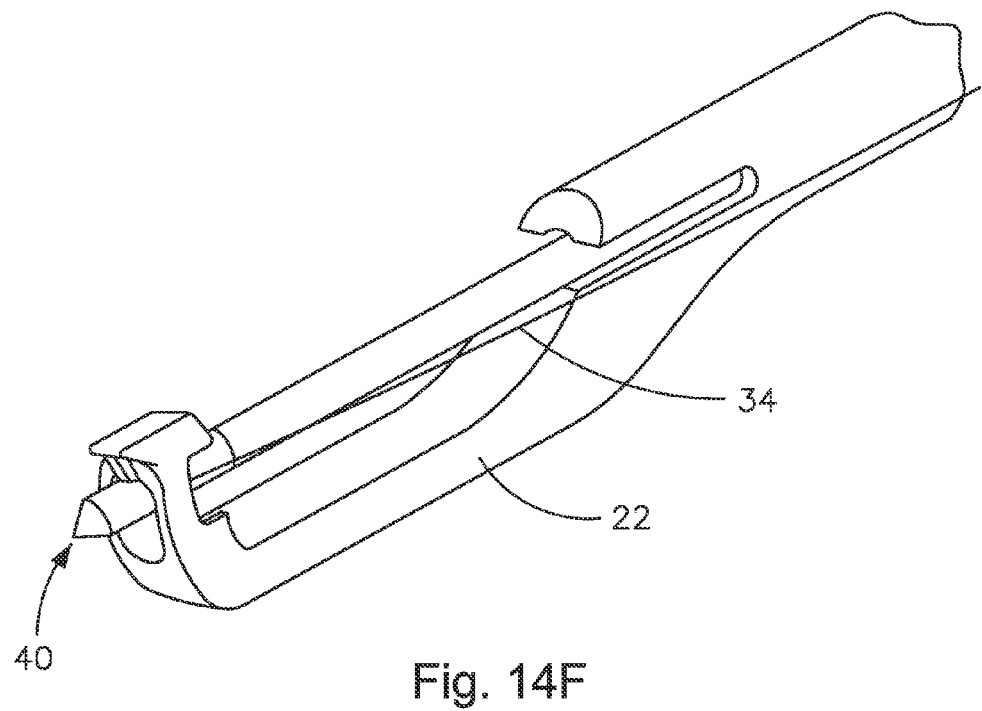
FIG. 14F is an enlarged side perspective view of the distal end of the instrument shown in FIG. 14E.

In operation, an operator engages the shuttling element 40, with an attached strand of suture, onto the needle 34 by snapping the fins 254 of the needle into the grooves 312 of the shuttling element 40, and, optionally, places the suture through the suture tensioner 350, as shown in FIG. 14A. An operator then grasps the handle 14 with an index and middle finger and disposes a thumb through the thumb ring 30, with the actuator 26 in a position retracted proximally from the handle 14. Tissue including a tissue defect, such as a fissure through the annulus fibrosis of an intervertebral disc, is received within the tissue receiving gap 202 disposed between the boom arm housing 198 and body member 18. With the thumb ring lock 130 in an open or unlocked configuration via the actuation of the thumb ring lock cap 138, the thumb ring 30 is translated distally with respect to the handle 14, thereby advancing the actuator 26 and the needle 34 distally with respect to the handle 14 and causing the distal end of the needle 34 and the shuttling element 40 attached thereto, as well as the suture attached to the shuttling element 40, to pass through the tissue adjacent to the defect and force contact to be made between the shuttling element 40 and the distal end of the boom arm 22, as shown in FIG. 14C. The tip actuator 180 is then actuated, rotating the needle 34 90 degrees, thereby causing the locking mechanism 320 of the shuttling element 40 to engage the locking interface 214 of the boom housing 198, as shown in FIG. 14E.

Figure 14G:
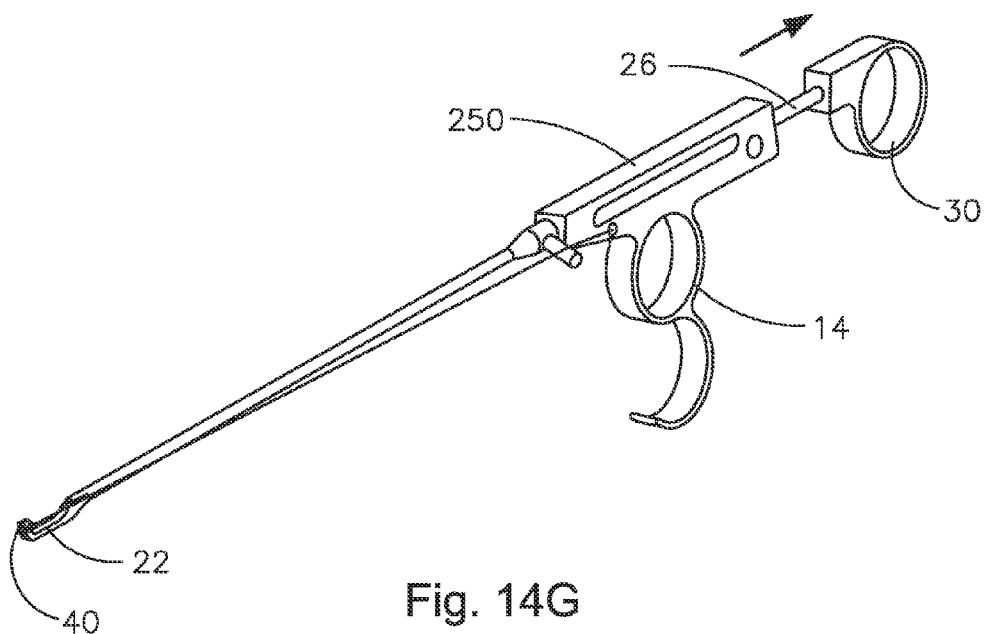
FIG. 14G is a side perspective view of the instrument shown in FIG. 14A, showing the needle in a retracted position and the shuttling element coupled to the boom arm.
Figure 14H:
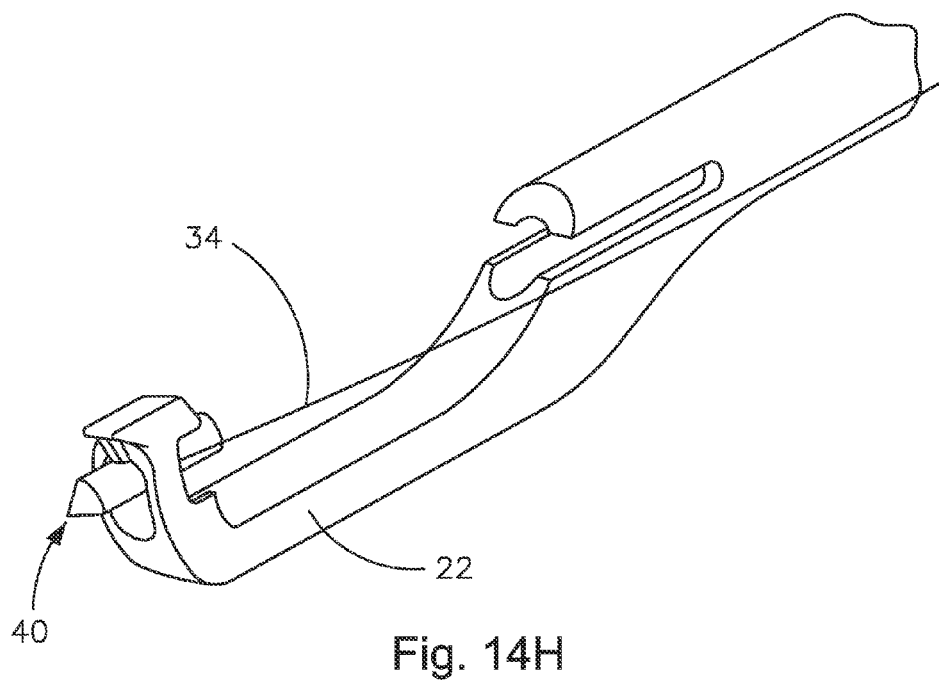
FIG. 14H is an enlarged side perspective view of the distal end of the instrument shown in FIG. 14G.
Figure 14I:
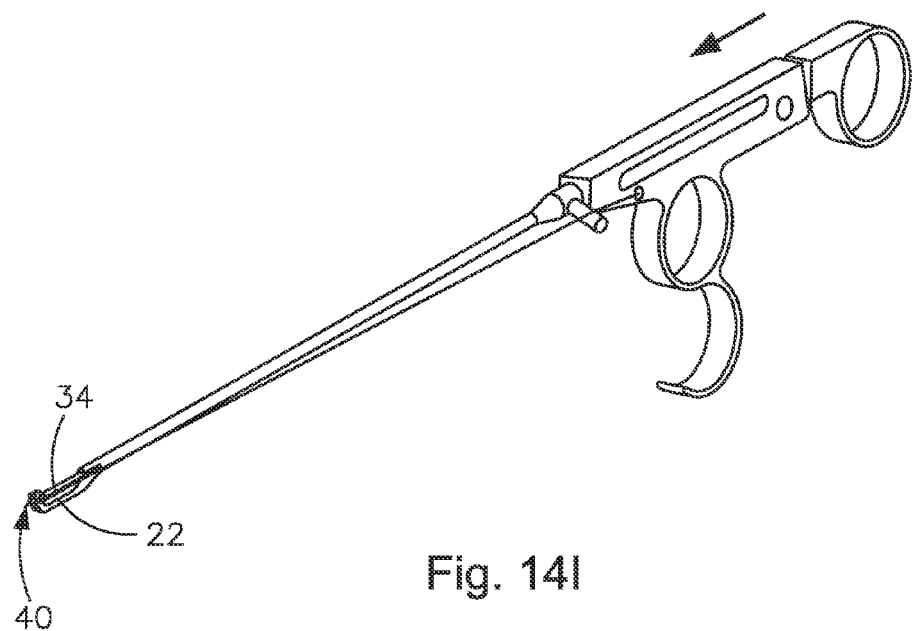
FIG. 14I is a side perspective view of the instrument shown in FIG. 14A, showing the needle in an advanced position and the shuttling element coupled to the boom arm.
Figure 14J:
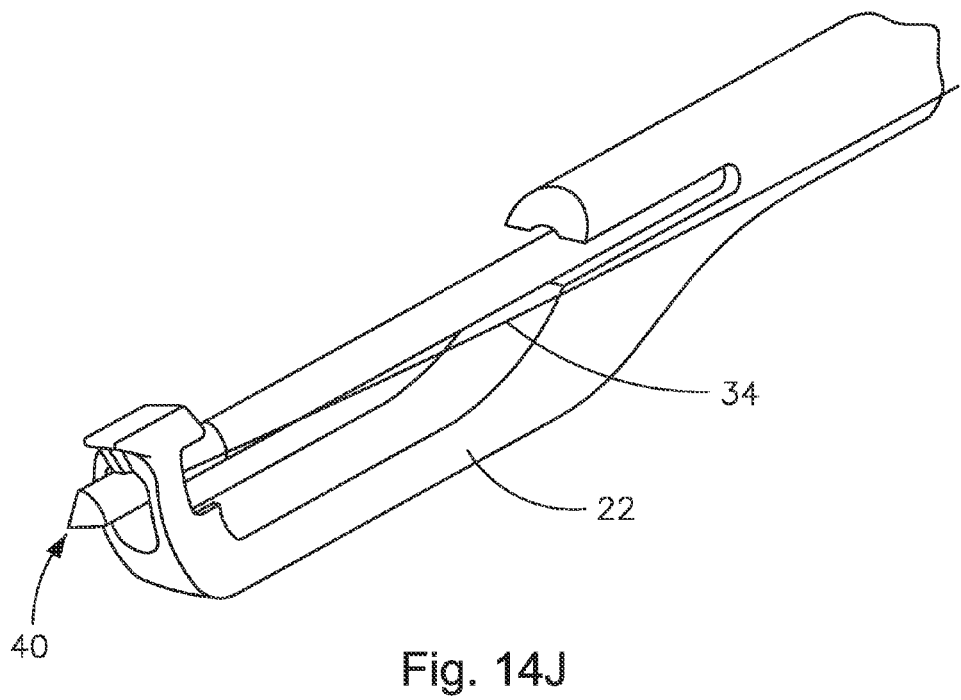
FIG. 14J is an enlarged side perspective view of the distal end of the instrument shown in FIG. 14I.
Figure 14K:
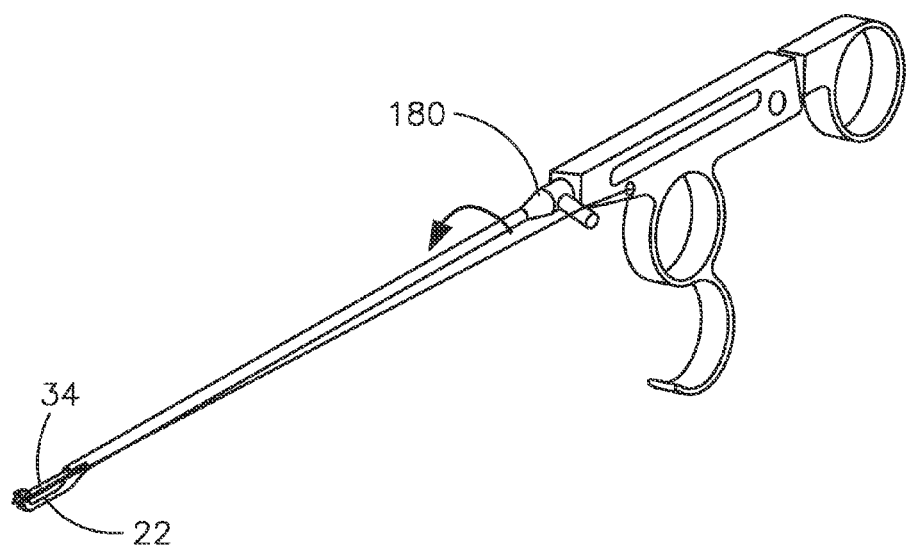
FIG. 14K is a side perspective view of the instrument shown in FIG. 14A, showing the needle in an advanced position and the shuttling element uncoupled from the boom arm.
Figure 14L:
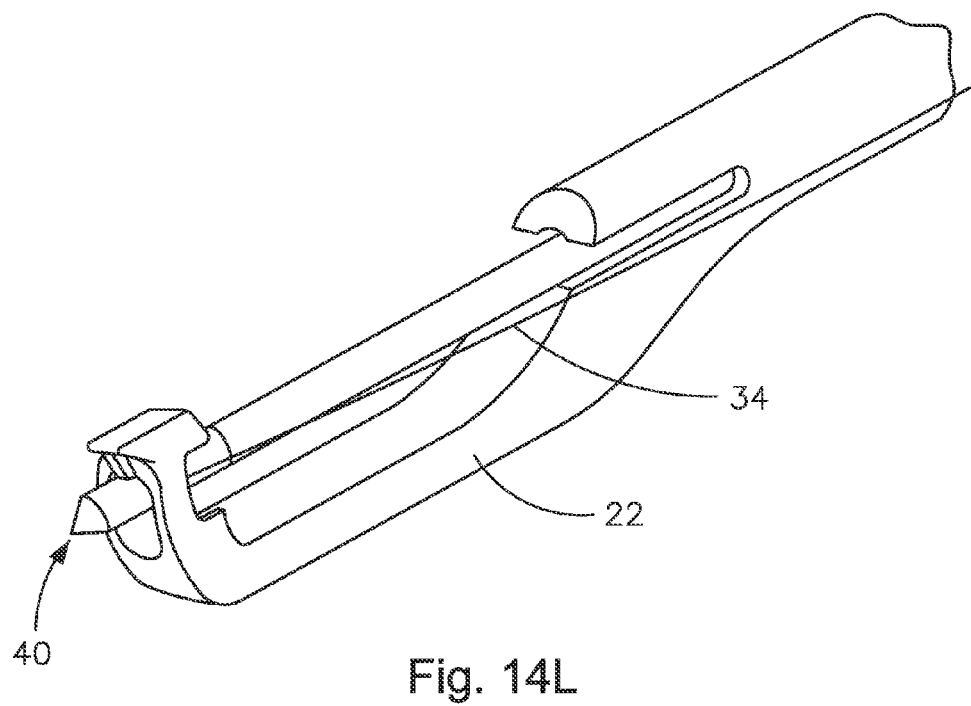
FIG. 14L is an enlarged side perspective view of the distal end of the instrument shown in FIG. 14K.
Figure 14M:
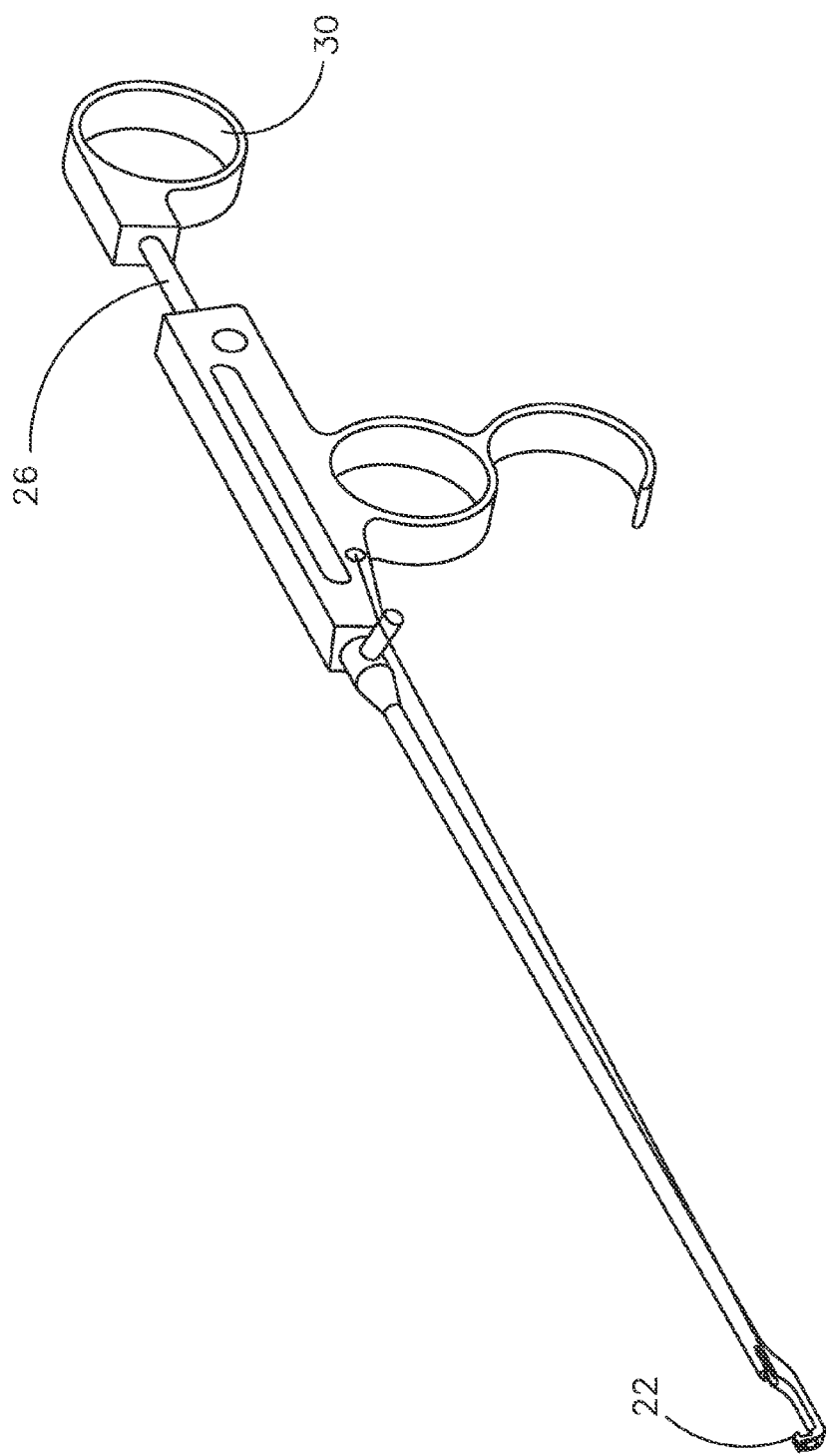
FIG. 14M is a side perspective view of the instrument shown in FIG. 14A, showing the needle in a retracted position and the shuttling element coupled to the needle.

When the needle 34 is retracted, the shuffling element 40 will be released from the needle 34 and remain selectively coupled to the boom arm housing 198, thereby maintaining the shuttling element 40 and connected suture strand on the underside of the tissue adjacent the defect. The needle 34 is then retracted into the protective sheath embodied by the body member 18, as shown in FIG. 14G. The boom arm 22 is then manipulated, e.g., rotated, with the needle 34 safely shielded, to another area on the underside of the tissue adjacent the defect, e.g., on an opposite underside of the defect, and, once optimally relocated, the needle 34 is translated distally again with respect to the handle 14 using the thumb ring 30 and maintaining the thumb ring lock 130 and thumb ring lock cap 134 in an unlocked position, thereby forcing the needle 34 to pass through from the top side to the underside of the tissue at a second site adjacent to the defect and cause the distal end of the needle 34 to re-engage or snap back into the shuttling element 40, as shown in FIG. 14K. The tip actuator 180 is then re-actuated or rotated 90 degrees in a rotational direction that is opposite to the first actuation of the tip actuator 198, thereby unlocking the shuttling element 40 from the boom housing 198. The thumb ring 30 is then retracted proximally with respect to the handle 14, causing the corresponding retraction of the actuator 26 and the needle 34, and thereby causing the distal end of the needle 34 and the shuttling element 40 with suture to disengage from the boom arm 22 and pass from the underside of the tissue adjacent the defect out through the topside of the tissue adjacent the defect, as shown in FIG. 14M. The steps can be repeated one or more times as desired, depending on the size of the defect and the characteristics of the tissue.

Figure 15:
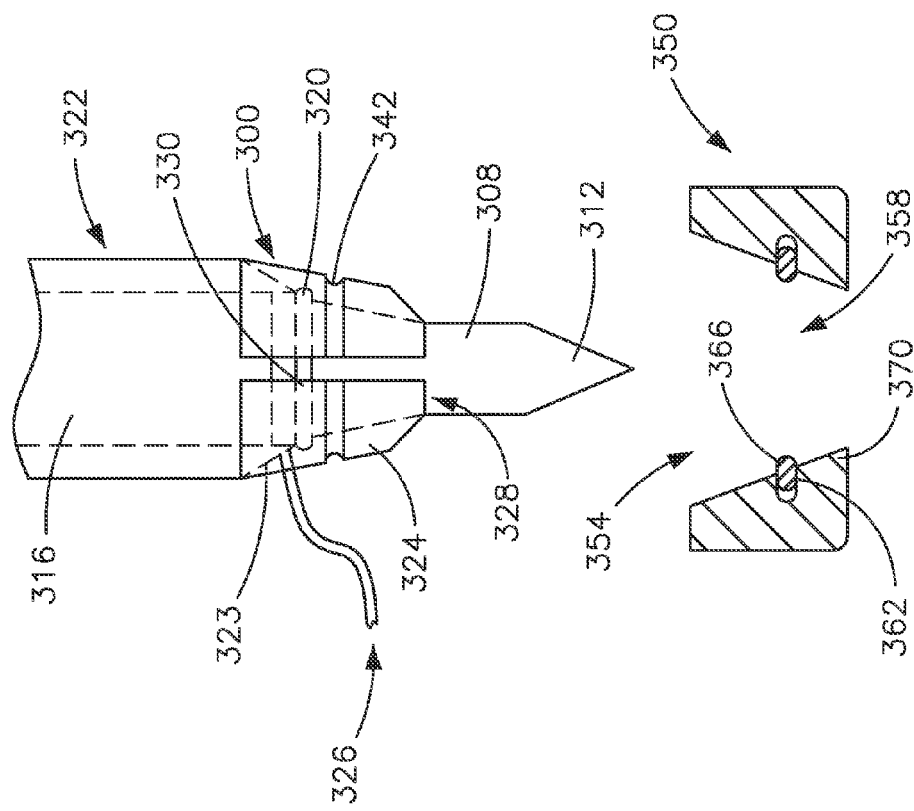
FIG. 15 is a partial side elevational view showing another embodiment of the bi-directional suture instrument having a ring like shuttling element that is selectively coupleable to a boom arm housing, the boom arm housing is shown in cross section for clarity.
Figure 17A:
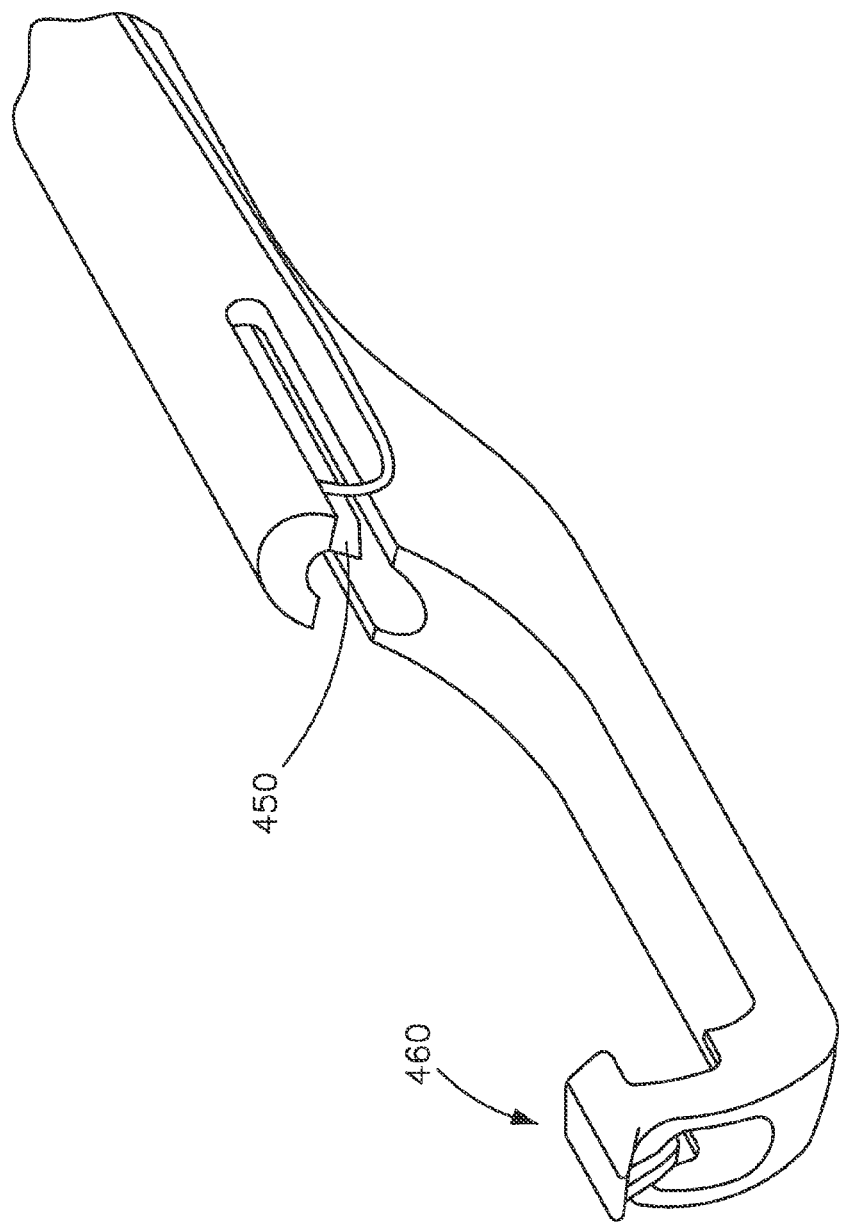
FIG. 17A is an enlarged side perspective view of another embodiment of a bi-directional suture passing instrument including a needle having a cut configured to capture and carry a strand of suture to a boom arm housing.
Figure 17C:
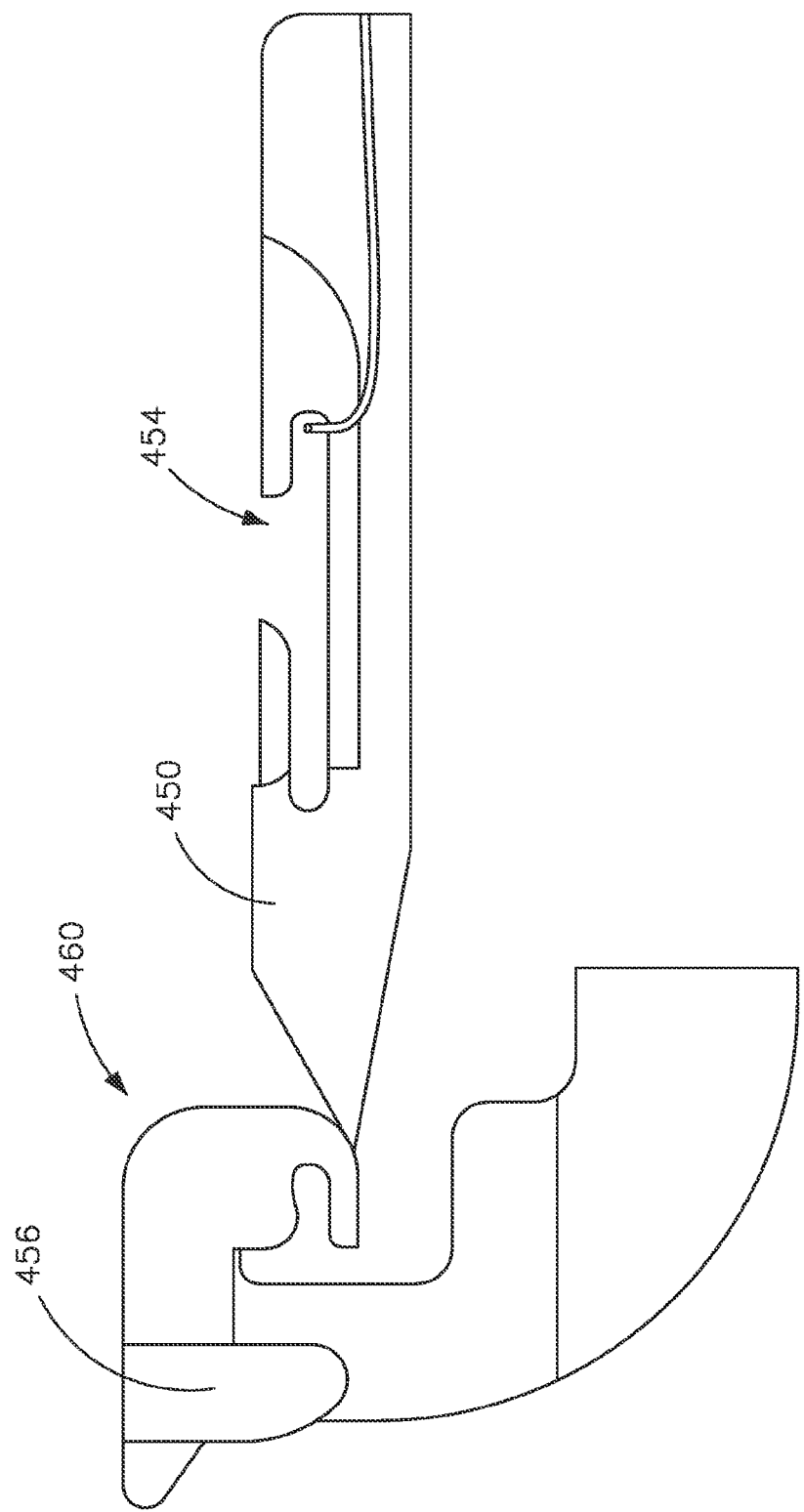
FIG. 17C is a side cross-sectional view of the boom arm housing illustrated in FIG. 17B, showing the needle advancing toward the boom arm housing.
Figure 17E:
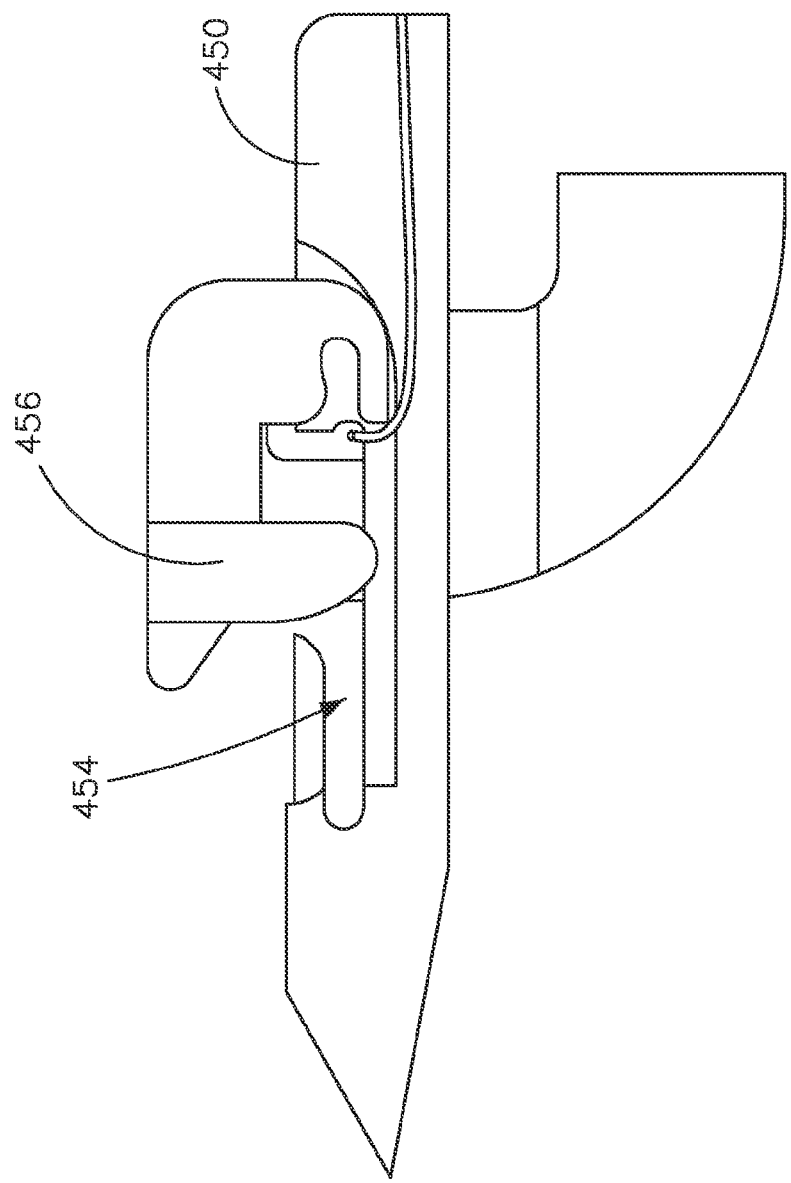
FIG. 17E is a side cross-sectional view of the boom arm housing illustrated in FIG. 17D, showing the needle rotated so that the locking interface of the boom arm housing can capture the suture strand.

In another embodiment, and in reference to FIG. 15, a ring like shuttling element may be used. As shown in FIG. 15, the bi-directional suture passing instrument 10 may include a ring-like shuttling element 300 that is configured to snap fit over a needle 308. As shown, the needle 308 includes a needle element 312 that extends from a shaft 316. The needle 308 also includes an engagement feature such as a rib 320 that is formed around a distal end of the shaft 316. The needle element 312 and a portion of the shaft 316 may be reciprocally translatable at least partially through the shuttling element 300. Disposed around the shaft 316 is a releasing tube 322 having an angled engagement surface 323 at its distal end. Tube 322 is configured to slide along shaft 316 to allow the angled surface 323 of the tube 322 to contact the shuttling element 300, to thereby facilitate disengagement of the shuttling element 300 from the needle 308.

The shuttling element 300 includes a ring like body 324 having a bore 328 that extends through the body 324. Attached to the body 324 is a suture strand 326. The body 324 includes a trough 330 formed in an internal surface of the bore 328, that defines an engagement feature that corresponds to the engagement feature of the needle 308. Preferably the body 324 has spring-like properties to enable diametrical expansion. Diametrical expansion of the body 324 will allow the engagement features to easily engage and disengage each other. The body 324 also includes a locking mechanism, such as trough 342 formed in an outer surface of the body 324. The trough 342 allows the shuttling element to be selectively coupled to the boom arm housing of a boom arm, such as boom arm housing 350 shown in FIG. 15.

As shown, the boom arm housing 350 includes an opening 354 that provides access to a chamber 358. The chamber 358 is tapered and is configured to receive the shuttling element 300 and the needle 308. The chamber 358 includes a locking interface 362 that corresponds to the locking mechanism 338 formed on the shuttling element 300. As shown, the locking interface 362 includes a spring loaded retaining washer 366 that is housed within a retaining groove formed in an inner surface of the chamber 358. The spring loaded washer 366 is configured to engage the trough 342 formed in the body 324 of the shuttling element 300. To aid in the disengagement of the shuttling element 300 from the boom arm housing 350, the chamber 358 includes a conical relief 370 at its distal end to allow the shuttling element 300 to spring outwardly to reengage the needle 308.

In operation, the needle 308, the shuttling element 300, the outer releasing tube 322, and the suture 326 are passed through tissue from a first side to a second side by actuating the actuator of the instrument. The shuttling element 300 is then received into the boom arm housing 350 on the second side of the tissue, and the shuttling element 300 is locked into the boom arm housing 350 via a snap fit between the retaining washer 366 and the locking trough 342 on the shuttling element 300, thereby positioning the suture on the second side of the tissue. The snap fit between the shuttling element 300 and the needle 308 is preferably released by holding the shuttling element 300 in place with the outer releasing tube 322 while the needle 308 is slightly retracted. Once the snap fit between the shuttling element 300 and the needle 308 is released, the needle 308 and the outer releasing tube 322 are further retracted into a retracted position inside the bore of the body member of the suture passer instrument 10, and the outer releasing tube 322 is further retracted to its original position relative to the needle 308. The boom arm can then be moved to another area on the second side of the tissue. Once relocated, the needle 308 and the outer releasing tube 322 are actuated and passed through the tissue from a first side to a second side, where the needle 308 reengages the shuttling element 300 via the snap fit. The needle 308, the shuttling element 300, the outer releasing tube 322, and the suture 326 are then fully retracted, thereby releasing the shuttling element from its snap fit engagement within the boom arm housing 350, and thereby bringing the suture from the second tissue side back to the first tissue side.

In another embodiment, and in reference to FIGS. 16A and 16B, a wire like suture loop may be utilized instead of a shuttling element. As shown in FIG. 16A, the bi-directional suture passing instrument 10 may include a wire-like suture loop 400 having shape memory characteristics, instead of a shuttling element that can be captured in the boom arm housing of a boom arm, such as boom arm housing 404. As shown, the suture loop 400 may be disposed around a needle 408. When the suture loop 400 is around the needle 408, tension is applied to the loop 400 so that it can be maintained on the needle 408. The suture loop 400 is preferably spring loaded such that it can be captured and retained within a retaining groove or notch 412 formed in the boom arm housing 404. The spring loading is a result of a wire connected to the distal end of the suture having a shape memory, such as can be provided by the inclusion of Nitinol. In this regard, the suture loop and the needle may be considered engagement features.

In another embodiment, and in reference to FIGS. 17A-17E, the bi-directional suture passing instrument 10 may include a needle 450 having a cut 454 configured to capture and carry a strand of suture. The needle 450 with suture is passed through tissue from a first side to a second side by advancing the thumb ring or actuating a simple triggering mechanism. The needle 450 is deflected by a finger 456 that extends from a boom arm housing 460 and the suture is then received and captured into the boom arm 460 on the second side of the tissue. The needle 450 is then retracted into the protective sheath while the suture remains on the second side of the tissue. To recapture the suture, the needle 450 is advanced into the boom arm housing 460 and then rotated. When the needle 450 is retracted, the suture will be recaptured by the cut 454.

Figure 18A:
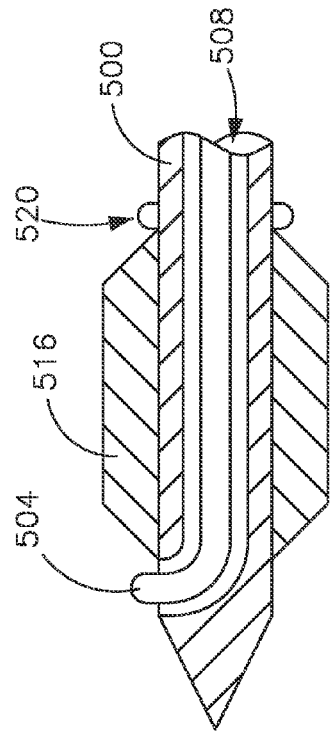
FIG. 18A is a partial side cross-sectional view of another embodiment of the bi-directional suture passing instrument having a deployable wire stop for detachably coupling the shuttling element to the needle.
Figure 18B:
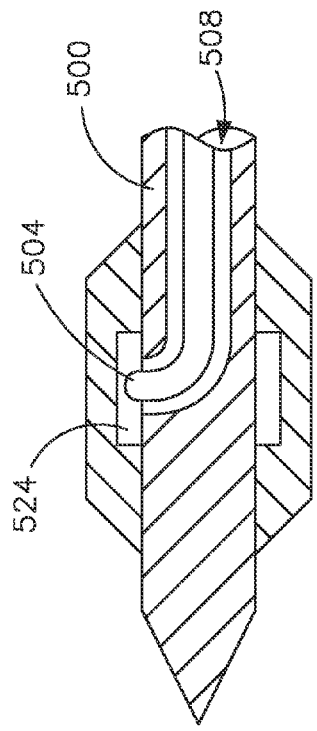
FIG. 18B is a partial side cross-sectional view of the instrument illustrated in FIG. 18B, showing the wire stop in a fully deployed state.
Figure 19A:
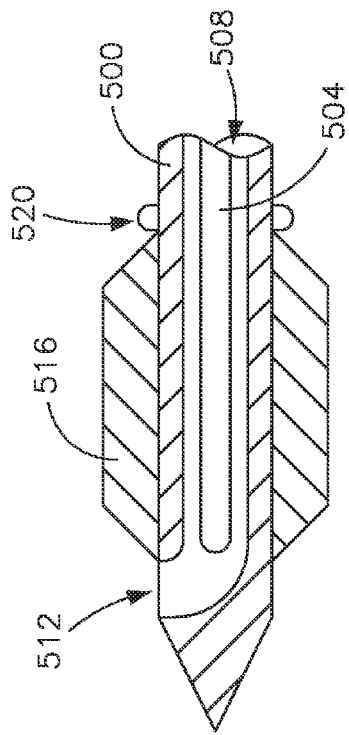
FIG. 19A is a partial side cross-sectional view of the instrument shown in FIG. 18A having a shuttling element that defines a recess that is configured to be engaged by the wire stop.
Figure 19B:
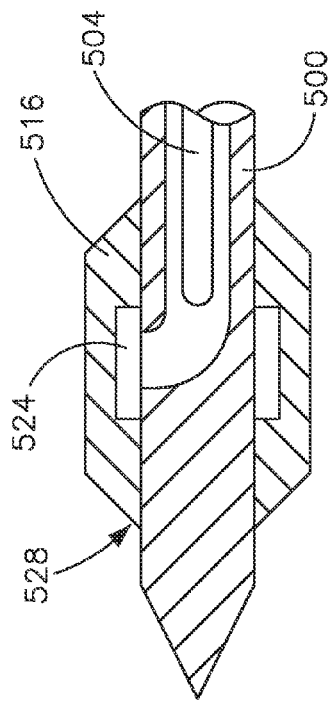
FIG. 19B is a partial side cross-sectional view of the instrument shown in FIG. 19A, with the wire stop fully deployed and engaging the recess of the shuttling element.

In another embodiment and in reference to FIGS. 18A and 18B, the bi-directional suture passing instrument 10 may include a needle 500 and a deployable wire stop 504 translatable within a channel 508 of the needle 500. As shown, the channel 508 extends through the center of the needle 500 and terminates at an opening 512 proximate to a distal end of the needle 500. The deployable wire stop 504 is translatable within the channel 508 between an extended position as shown in FIG. 18B and a retracted position as shown in FIG. 18A. When the wire stop 504 is in an extended position, the wire stop 504 exits the opening 512 to provide a buttress against a front end of a tube-like shuttling element 516 that is disposed around the needle 500, thereby trapping the shuttling element 516 between the wire stop 504 and a buttress 520 formed on an upper surface of the needle 500. The buttress 520 may be a ring that extends completely around the needle 500, or even a single bead. Alternatively, the wire stop 504 can extend into a recess 524 formed in an internal surface of a bore 528 of the shuttling element 516 as shown in FIGS. 19A and 19B. In this regard, the wire stop 504, buttress 520, and shuttling element 516 may each define engagement features to allow the shuttling element 516 to be selectively coupled to the needle 500. It should be understood that the front and back sides of the shuttling element may be considered engagement features.

As shown in FIGS. 20A-20D, the shuttling element 516, needle 500, and wire stop 504 are reciprocally translatable to and from a boom arm housing such as boom arm housing 540. Boom arm housing 540 includes a bore 544, and a locking interface 548 proximate to an opening of the boom arm housing 540. Locking interface 548 includes an elastomeric member 552 extending from an internal surface of the bore 544 of the housing 540. The elastomeric member 552 may take the form of an elastomer or could be a shape other than an o-ring shape, such as but not limited to, square, triangular, cylindrical, conical, elliptical, etc. Alternatively, a toroidal spring may be used instead of an elastomeric member.

Figure 20A:
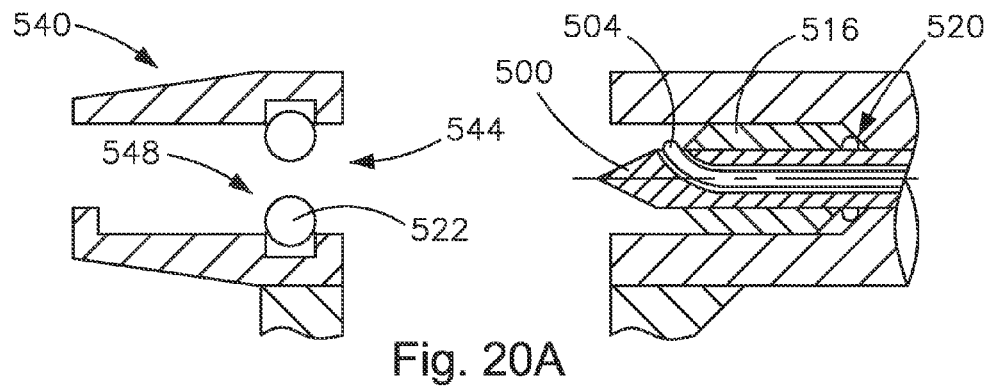
FIG. 20A is a partial side cross-sectional view of a bi-directional suture passing instrument having a wire stop as illustrated in FIG. 18A, showing the needle in a retracted position.
Figure 20B:
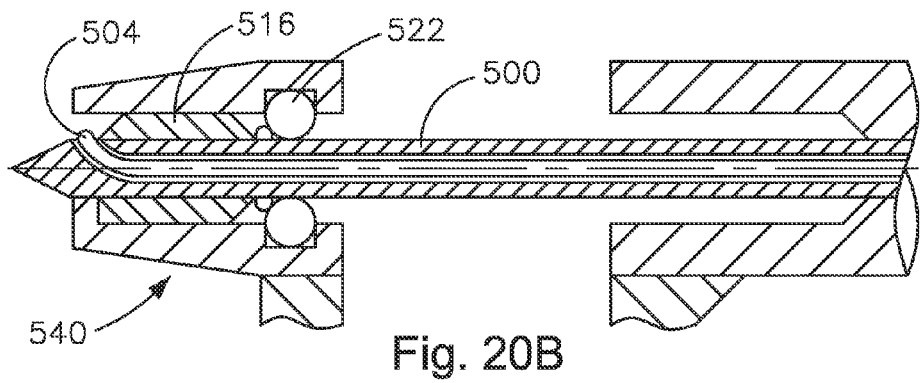
FIG. 20B is a partial side cross-sectional view of the instrument illustrated in FIG. 20A, showing the needle in a fully advanced position, in which the shuttling element is housed within the boom arm housing.
Figure 20C:
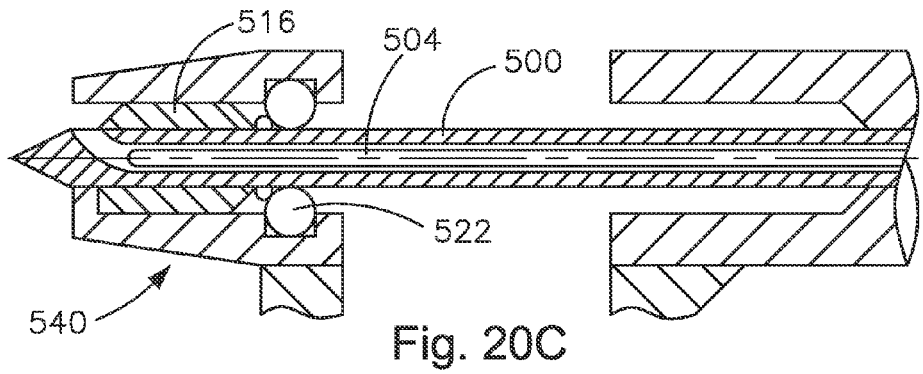
FIG. 20C is a partial side cross-sectional view of the instrument illustrated in FIG. 20B, showing the wire stop of the needle fully retracted.

In operation, the needle 500 translates into the bore 528 of the shuttling element 516 until the proximal end of the shuttling element 516 engages (i.e. abuts) the buttress 520 formed on the needle 500. The wire stop 504 is then translated to an extended position, to thereby engage or form a buttress with a distal end of the shuttling element 516. The needle 500 along with the shuttling element 516 that is trapped between the wire stop 504 and the buttress 520, may then be translated through the tissue and into the boom arm housing 540. As the shuttling element 516 contacts the elastomeric member 552, the member 552 biases to allow the shuttling element 516 to enter the boom arm housing 540. Once the shuttling element is fully in the housing 540, the elastomeric member 552 returns to its original form, as shown in FIG. 20B.

Figure 20D:
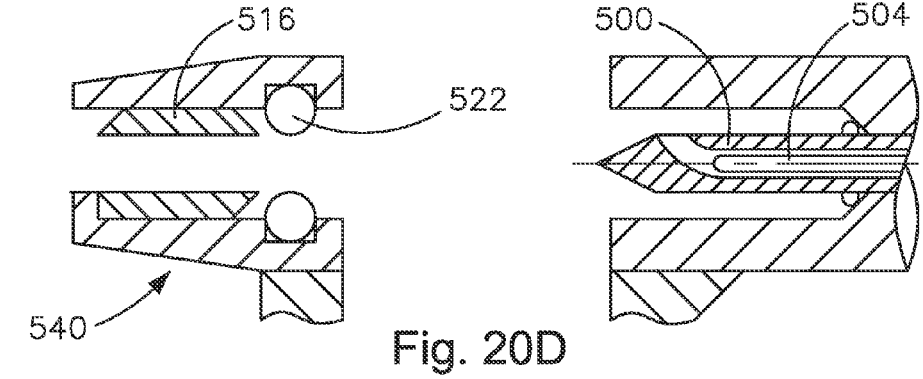
FIG. 20D is a partial side cross-sectional view of the instrument illustrated in FIG. 20C, showing the needle in a fully retracted position, and the shuttling element is coupled to the boom arm housing.

To retain the shuttling element 516 within the boom arm housing 540, the wire stop 504 is retracted back into the channel 508, and the needle 500 along with the wire stop 504 are retracted. As the needle 500 is retracted, the elastomeric member 552 prevents the shuttling element 516 from retracting with the needle, as shown in FIG. 20D, to thereby leave the shuttling element 516 in the boom arm housing 540. The steps can be repeated one or more times as desired, depending on the size of the defect and the characteristics of the tissue. It should be understood that the deployable wire stop 504 may contain two or more wires that exit the needle 500, where each wire is radially separated by an angle between 0 and 360 degrees (not shown). Furthermore, the deployable wire stop 504 or stops may be round, square, rectangular, triangular, or any other shape known in the art.

In another embodiment, and in reference to FIGS. 21A-21F, a wedge can be utilized instead of a deployable wire stop to detachably couple the shuttling element to the distal portion of the needle. As shown, the bi-directional suture passing instrument 10 may include a needle 600, a wedge 604 that is translatable within a channel 608 formed in the needle 600, and a disengagement tube 612 that is translatable about an outer surface of the needle 600. The proximal ends of the needle 600, the wedge 604, and the disengagement tube 612 are together reciprocally translatable within the interior of the body member of the instrument 10.

As shown, the channel 608 is formed in a top surface of the needle 600 and extends along a substantial length of the needle 600. The wedge 604 that is disposed in the channel 608 is translatable within the channel 608 and includes an angled front surface 624 that is configured to release a shuttling element 620 that is detachably coupled to the needle 600.

As shown, the shuttling element 620 includes a body 632, a bore 636 that extends through the body 632, and one or more axial fingers 640 cut into the body 632. The bore 636 is configured to receive the needle 600. The axial finger 640 is deflectable and includes a protrusion 644 that extends into the bore 636 of the shuttling element body 632.

Figure 21A:
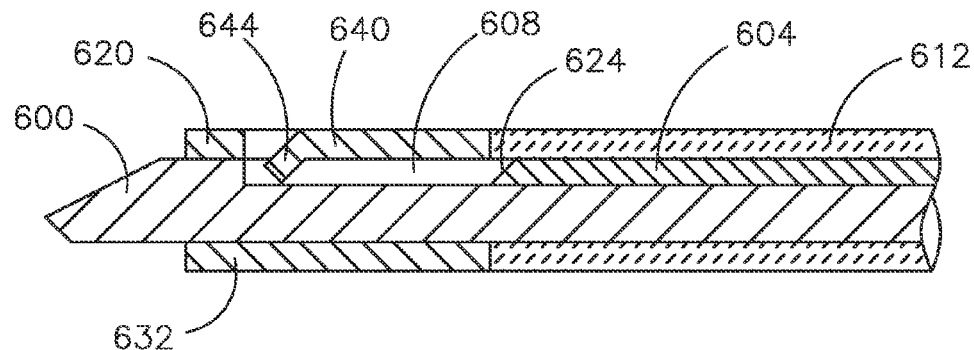
FIG. 21A is a partial side cross-sectional view of a another embodiment of the bi-directional suture passing instrument, in which the needle includes a disengagement tube, and a wedge that engages a deflectable finger defined by the shuttling element to decouple the shuttling element from the needle.
Figure 21B:
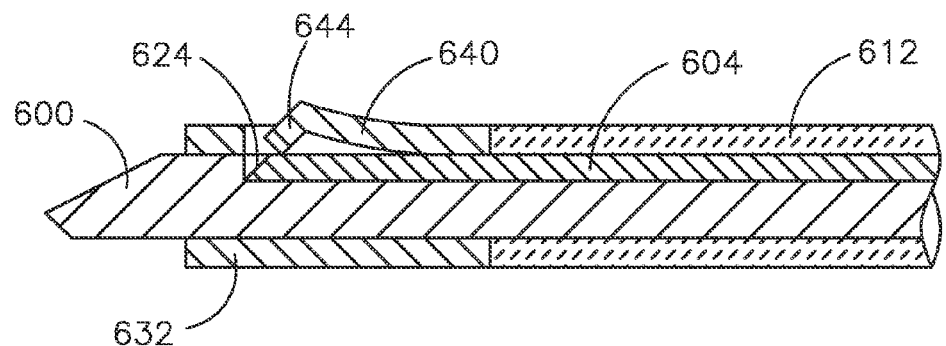
FIG. 21B is a partial side cross-sectional view of the instrument illustrated in FIG. 21A, showing the wedge in a fully advanced position.
Figure 21C:
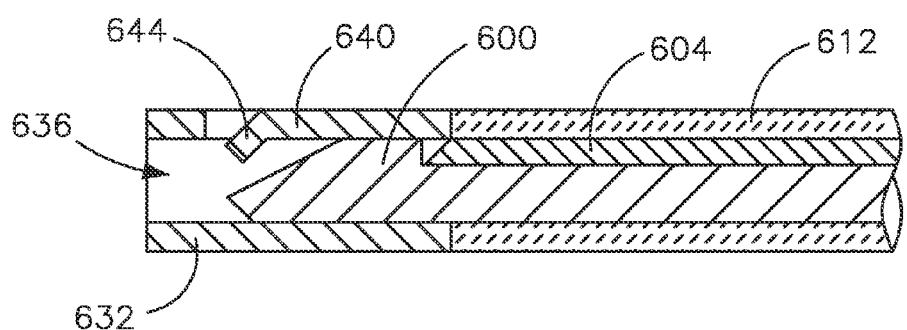
FIG. 21C is a partial side cross-sectional view of the instrument illustrated in FIG. 21B, showing the disengagement tube in a fully advanced position.
Figure 21D:
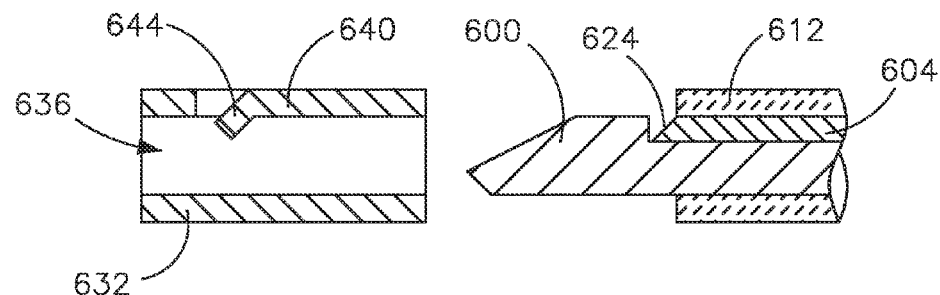
FIG. 21D is a partial side cross-sectional view of the instrument illustrated in FIG. 21C, showing the needle in a fully retracted position, and decoupled from the shuttling element.
Figure 21E:
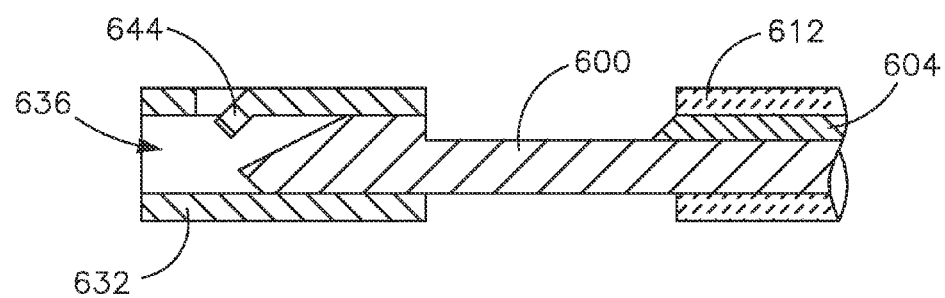
FIG. 21E is a partial side cross-sectional view of the instrument illustrated in FIG. 21D, showing the needle advancing toward the shuttling element.
Figure 21F:
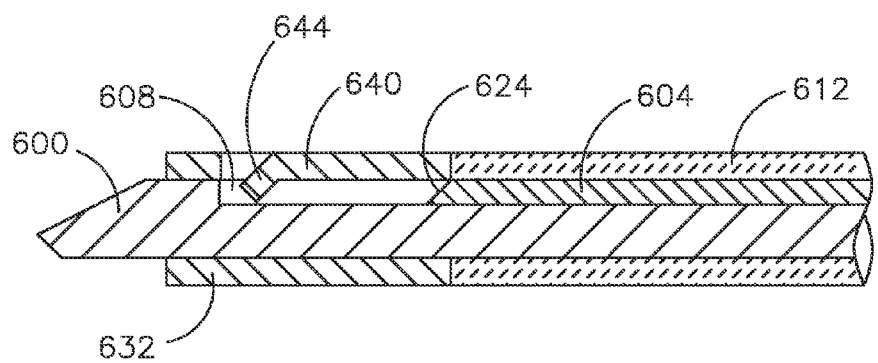
FIG. 21F is a partial side cross-sectional view of the instrument illustrated in FIG. 21E, showing the shuttling element recoupled to the needle.

In operation, the needle 600 translates into the bore 636 of the shuttling element 620 until the protrusion 644 of the finger 640 extends into the channel 608 of the needle 600, to detachably couple the shuttling element 620 to the needle 600. In this regard, the finger 640 and channel 608 can said to be engagement features that allow the shuttling element 620 to be selectively coupled to the needle 600. The disengagement tube 612 engages the shuttling element 620 so as to push the shuttling element 620 as the needle 600 is translated through the tissue and into the boom arm. To release the shuttling element 620, the wedge 604 is translated forward, via actuation of a tip actuator, within the channel 608 until the angled surface 624 of the wedge 604 contacts and forces up the finger 640 of the shuttling element 620, as shown in FIG. 21B. Simultaneously, the tip actuator advances the disengagement tube 612 to thereby push the shuttling element 620 off of the needle 600, as shown in FIG. 21C. Advancement of the wedge 604 and the disengagement tube 612 lift the finger 640 of the shuttling element 620, thereby releasing the shuttling element 620 from the needle 600 and enabling the shuttling element 620 to be releasably coupled to the distal portion of the boom arm. The needle 600, wedge 604, and disengagement tube 612 are then simultaneously retracted into the protective sheath embodied by the instrument body, while the shuttling element 620 remains behind in the distal portion of the boom arm. To recouple the shuttling element 620 to the needle 600, the needle 600 may be advanced into the bore 636 of the shuttling element 620 until the protrusion 644 of the finger 640 once again extends into the channel 608 of the needle 600, as shown in FIGS. 21E and 21F. When the protrusion 644 of the finger 640 is extending into the needle channel 608, the shuttling element 620 may be retracted with the needle 600 from the distal portion of the boom arm.

Figure 22A:
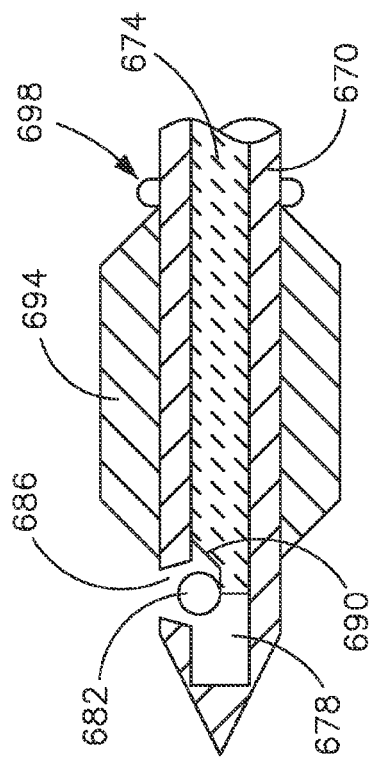
FIG. 22A is a partial side cross-sectional view of another embodiment of the bi-directional suture passing instrument, in which a deployable ball stop is used to detachably couple the shuttling element to the needle.
Figure 22B:
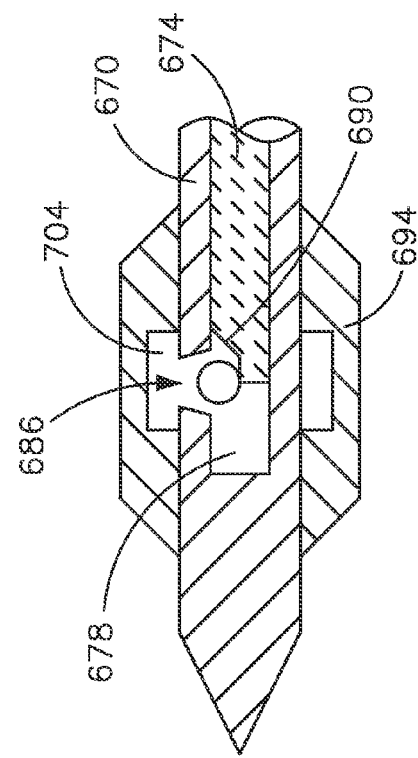
FIG. 22B is a partial side cross-sectional view of the instrument illustrated in FIG. 22A, showing the ball stop fully deployed by a wedge.
Figure 23A:
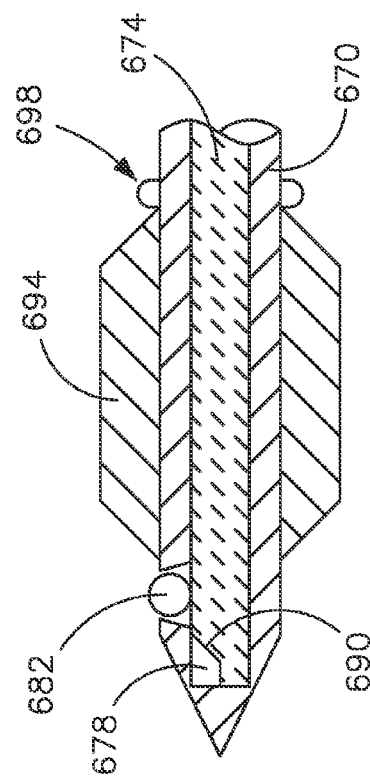
FIG. 23A is a partial side cross-sectional view of the instrument shown in FIG. 22A having a shuttling element that defines a recess that is configured to be engaged by the ball stop.
Figure 23B:
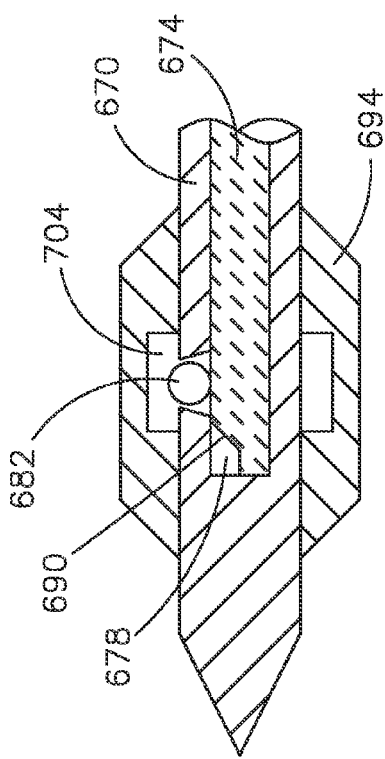
FIG. 23B is a partial side cross-sectional view of the instrument illustrated in FIG. 23A, showing the ball stop fully deployed by a wedge, and engaging the recess of the shuttling element.

In another embodiment, and in reference to FIGS. 22A and 22B, a deployable ball stop can be utilized instead of a deployable wire stop to detachably couple the shuttling element to the distal portion of the needle. As shown in FIG. 22A, the bi-directional suture instrument 10 may include a needle 670, a wedge 674 translatable within a channel 678 of the needle 670, and a deployable ball stop 682 disposed within the channel 678 forward of the wedge 674. As shown, the channel 678 extends through the center of the needle 670 and terminates proximate to a distal end of the needle 670. Proximate to the end of the channel 678 is an opening 686 that enables at least a portion of the ball stop 682 to selectively extend out of the channel 678 and protrude out from the needle 670. The wedge 674 includes a ramp 690 at its distal end, and is translatable within the channel 678 between an extended position as shown in FIG. 22B and a retracted position as shown in FIG. 22A. When the wedge 674 is in an extended position, the ball stop 682 rides up the ramp 690 of the wedge 674 and through the opening 686 so that a portion of the ball stop 682 extends from the opening 686. The protruding ball stop 682 acts as a buttress against a front end of a tube-like shuttling element 694 that is disposed around the needle 670, thereby trapping the shuttling element 694 between the ball stop 682 and a buttress 698 formed on an upper surface of the needle 670. Alternatively, the ball stop 682 can extend into a recess 704 formed in a bore 708 of the shuttling element 694 as shown in FIGS. 23A and 23B. In this regard, the ball stop 682, buttress 698, and shuttling element 694 may each define engagement features to allow the shuttling element 694 to be selectively coupled to the needle 670.

It should be understood that the ball stop 682 may include other configurations. For example, as shown in FIGS. 24A-24D, a ball stop 710 having a hemispheric top 714, and a triangular bottom 718 may be utilized. As shown, a wedge 722 having a ramp 726 at its distal end will contact the triangular bottom 718 of the ball stop 710, as the wedge is advanced forward to thereby cause the hemispheric top 714 to protrude from the opening of the needle, to thereby trap the shuttling element between the ball stop hemispheric top 714 and a buttress 728 extending from a surface of the needle. It should be appreciated by those skilled in the art that other shapes, such as rectangles, squares, triangles, polygons, etc. (not shown) could be utilized as buttressing elements in place of a hemisphere in the manner described above.

Figure 25A:
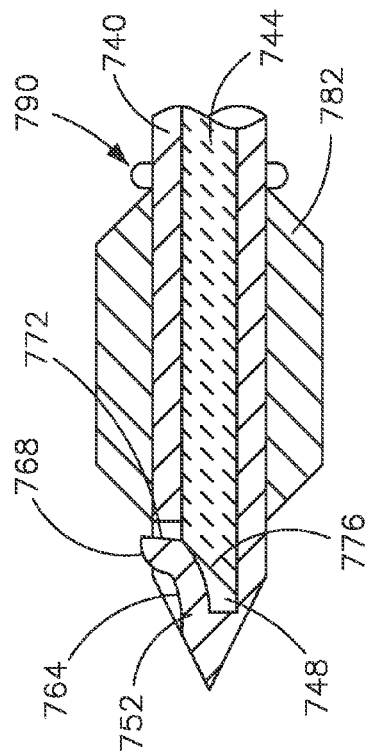
FIG. 25A is a partial side cross-sectional view of another embodiment of the bi-directional suture passing instrument, in which a deployable finger stop is used to detachably couple the shuttling element to the needle.
Figure 25B:
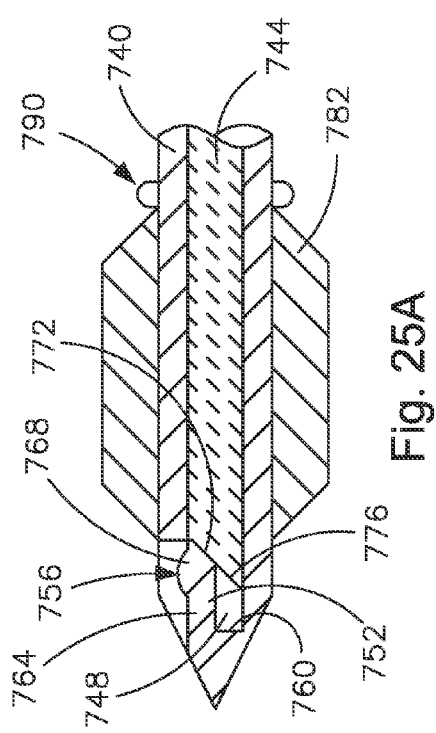
FIG. 25B is a partial side cross-sectional view of the instrument illustrated in FIG. 25A, showing the finger stop fully deployed by a wedge.
Figure 26A:
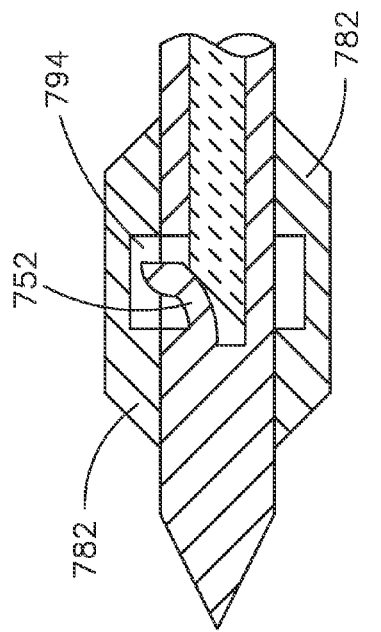
FIG. 26A is a partial side cross-sectional view of the instrument shown in FIG. 25A having a shuttling element that defines a recess that is configured to be engaged by the finger stop.
Figure 26B:
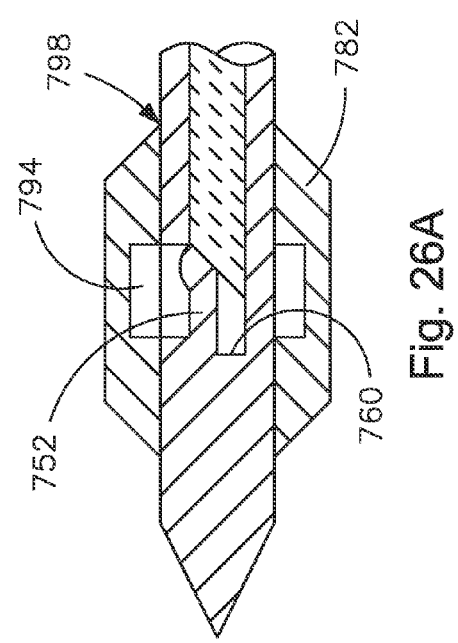
FIG. 26B is a partial side cross-sectional view of the instrument illustrated in FIG. 26A, showing the finger stop fully deployed by a wedge, and engaging the recess of the shuttling element.

In another embodiment, and in reference to FIGS. 25A and 25B, a deployable finger can be utilized instead of a deployable wire stop to detachably couple the shuttling element to the distal portion of the needle. As shown in FIG. 25A, the bi-directional suture instrument 10 may include a needle 740, a wedge 744 translatable within a channel 748 of the needle 740, and a deployable finger stop 752 disposed within the channel 748 forward of the wedge 744. As shown, the channel 748 extends through the center of the needle 740 and terminates proximate to a distal end of the needle 740. Proximate to the distal end of the channel 748 is an opening 756 that enables at least a portion of the finger stop 752 to selectively extend out of the channel 748 and protrude out from the needle 740. The finger stop 752 extends from a distal wall 760 of the channel 748 and includes an arm 764, and a head 768 extending from the arm 764. As shown, the head 768 includes an angled front surface 772. The wedge 744 includes a ramp 776 at its distal end, and is translatable within the channel 748 between an extended position as shown in FIG. 25B and a retracted position as shown in FIG. 25A. When the wedge 744 is in an extend position, the angled surface 772 of the finger stop 752 contacts and rides up the ramp 776 of the wedge 744 and through the opening 756 so that a portion of the head 768 of the finger stop 752 protrudes from the opening 756. The protruding finger stop 752 acts as a buttress against a front end of a tube-like shuttling element 782 that is disposed around the needle 740, thereby trapping the shuttling element 782 between the finger stop 752 and a buttress 790 formed on an upper surface of the needle 740. Alternatively, the finger stop 752 can extend into a recess 794 formed in a bore 798 of the shuttling element 782 as shown in FIGS. 26A and 26B. In this regard, the finger stop 752, buttress 790, and shuttling element 782 may each define engagement features to allow the shuttling element 782 to be selectively coupled to the needle 740.

Figure 27A:
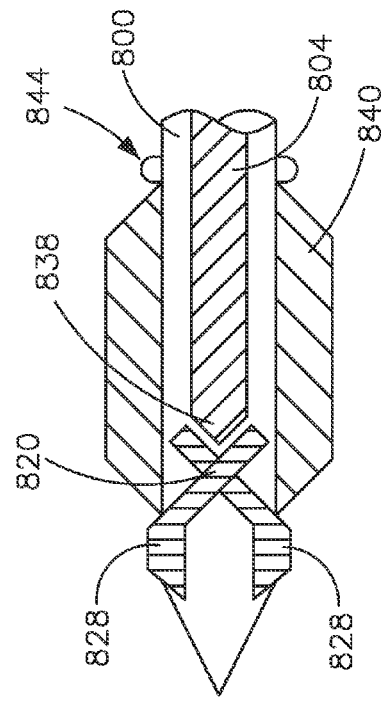
FIG. 27A is a partial side cross-sectional view of another embodiment of the bi-directional suture passing instrument, in which a deployable scissor stop is used to detachably couple the shuttling element to the needle.
Figure 27B:
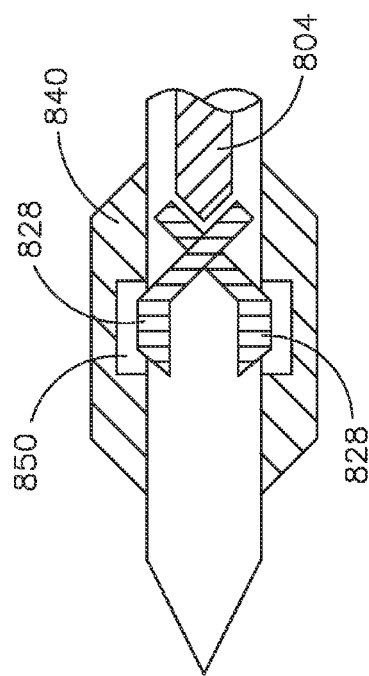
FIG. 27B is a partial side cross-sectional view of the instrument illustrated in FIG. 27A, showing the scissor stop fully deployed by a wedge.
Figure 28A:
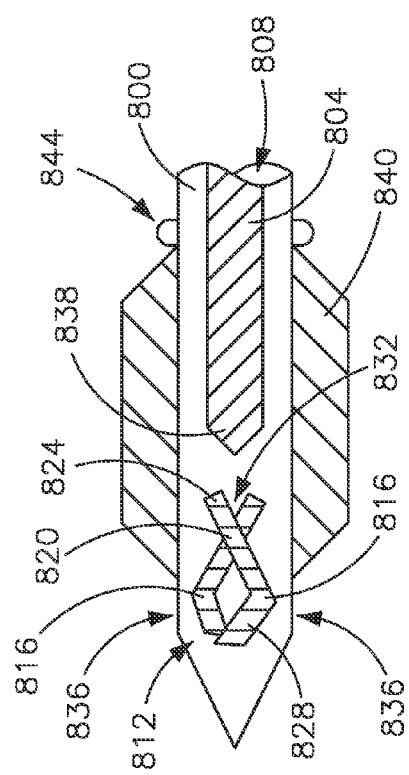
FIG. 28A is a partial side cross-sectional view of the instrument shown in FIG. 27A having a shuttling element that defines a recess that is configured to be engaged by the scissor stop.
Figure 28B:
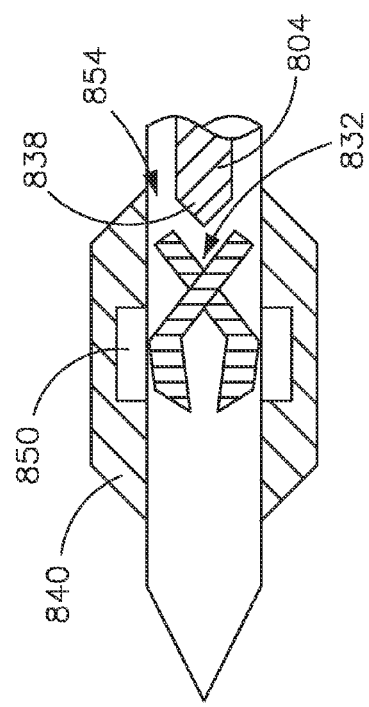
FIG. 28B is a partial side cross-sectional view of the instrument illustrated in FIG. 28A, showing the scissor stop fully deployed by a wedge, and engaging the recess of the shuttling element.

In another embodiment, and in reference to FIGS. 27A and 27B, a pair of deployable scissor fingers can be utilized instead of a deployable wire stop to detachably couple the shuttling element to the distal portion of the needle. As shown in FIG. 27A, the bi-directional suture instrument 10 may include a needle 800, a wedge 804 translatable within a channel 808 of the needle 800, and a deployable scissor stop 812 disposed within the channel 808 forward of the wedge 804. The scissor stop 812 includes two fingers 816 that are rotatable about a pivot 820. Each finger 816 includes an arm 824 and a head 828 extending from an end of the arm 824. The arms 824 of fingers 816 cross at the pivot 820 to thereby create a wedge contact cavity 832 behind the pivot 820. As shown, the channel 808 extends through the center of the needle 800 and terminates proximate to a distal end of the needle 800. Proximate to the end of the channel 808 are openings 836 that enable at least a portion of each finger 816 to selectively extend out of the channel 808 and protrude out from the needle 800, through activation by the wedge 804. The wedge 804 includes a triangular shaped end 838, and is translatable within the channel 808 between an extended position as shown in FIG. 27B and a retracted position as shown in FIG. 27A. When the wedge 804 is in an extend position, the shaped end 838 of the wedge 804 contacts the cavity 832 defined by the finger arms 824, and causes the arms 824 to pivot about pivot 820 until a portion of the heads 828 of the fingers 816 protrudes from each opening 836. The protruding heads 828 act as a buttress against a front end of a tube-like shuttling element 840 that is disposed around the needle 800, thereby trapping the shuttling element 840 between the scissor stop 812 and a buttress 844 formed on a surface of the needle 800. Alternatively, the scissor stop 812 can extend into a recess 850 formed in a bore 854 of the shuttling element 840 as shown in FIGS. 28A and 28B. In this regard, the scissor stop 812, buttress 844, and shuttling element 840 may each define engagement features to allow the shuttling element 840 to be selectively coupled to the needle 800.

In another embodiment, and in reference to FIGS. 29A and 29B, a deployable rotating boot can be utilized instead of a deployable wire stop to detachably couple the shuttling element to the distal portion of the needle. As shown in FIG. 29A, the bi-directional suture instrument 10 may include a needle 860, a wedge 864 translatable within a channel 868 of the needle 860, and a deployable boot stop 872 disposed within the channel 868 forward of the wedge 864. The boot stop 872 is pivotable about a pivot 876 and includes a head portion 880 that extends from a leg 882. As shown, the leg defines a cavity 883. As shown, the channel 868 extends through the center of the needle 860 and terminates proximate to a distal end of the needle 860. Proximate to the end of the channel 868 is an opening 884 that enables at least a portion of the head 880 of the boot stop 872 to selectively extend out of the channel 868 and protrude out from the needle 860, through activation by the wedge 864. The wedge 864 includes a triangular shaped end 886, and is translatable within the channel 868 between an extended position as shown in FIG. 29B and a retracted position as shown in FIG. 29A. When the wedge 864 is in an extend position, the shaped end 886 of the wedge 864 contacts the cavity 883 defined by the boot leg 882, and causes the boot stop 872 to pivot about pivot 876 until a portion of the head 880 of the boot stop 872 protrudes from the opening 884. The protruding head 880 act as a buttress against a front end of a tube-like shuttling element 890 that is disposed around the needle 860, thereby trapping the shuttling element 890 between the boot stop 872 and a buttress 894 formed on a surface of the needle 860. Alternatively, the boot stop 872 can extend into a recess 898 formed in a bore 900 of the shuttling element 890 as shown in FIGS. 30A and 30B. In this regard, the boot stop 872, buttress 894, and shuttling element 890 may each define engagement features to allow the shuttling element 890 to be selectively coupled to the needle 860.

Figure 31C:
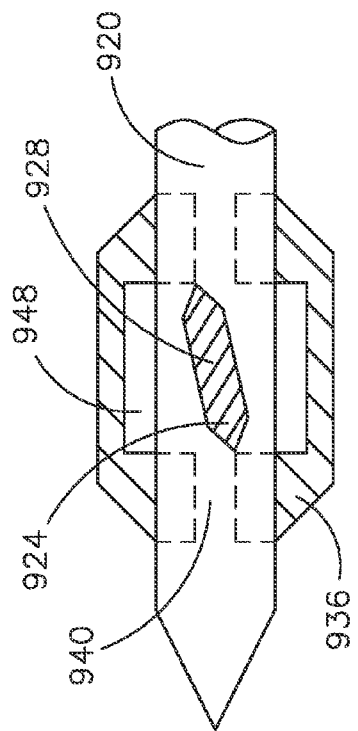
FIG. 31C is a partial side cross-sectional view of the instrument illustrated in FIG. 31B, showing the rotating wing deployed, to thereby couple the shuttling element to the needle.
Figure 31A:
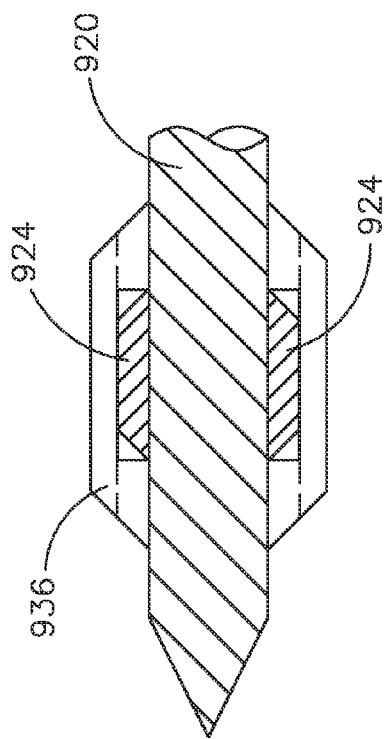
FIG. 31A is a partial side cross-sectional view of another embodiment of the bi-directional suture passing instrument, in which a rotating wing is used to detachably couple the shuttling element to the needle.
Figure 31B:
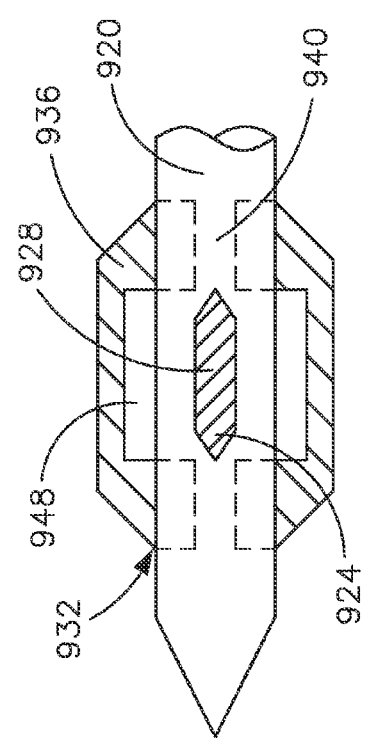
FIG. 31B is a partial side cross-sectional view of the instrument illustrated in FIG. 31A, showing the rotating wing aligned with slots defined by the shuttling element.

In another embodiment, and in reference to FIGS. 31A-31C, a deployable rotating wing can be utilized instead of a deployable wire stop to detachably couple the shuttling element to the distal portion of the needle. As shown in FIG. 31A, the bi-directional suture instrument 10 may include a needle 920 having two wings 924 rotatably coupled to an external surface of the needle 920. The rotating wings 924 are coupled to the needle 920 with a pin 928. One or more wires are attached to the rotating wings 924 which couples the wings 924 to an actuation mechanism. As shown, the needle 920 engages a bore 932 of a shuttling element 936. The shuttling element 936 includes axial slots 940 that extend through the shuttling element 936 and are aligned with the wings 924 of the needle 920. Thus, when the wings 924 are in an aligned position, as shown in FIGS. 31A-31B, they can pass through the slots 940 and into the bore 932 of the shuttling element. As shown, a groove or recess 948 is formed in an internal surface of the bore 932. The recess 940 is substantially in the middle of the bore 932 and is configured to be engaged by the wings 924 once they are rotated.

In operation, when the wire is advanced the wings 924 will rotate about the pin 928 and the ends of the wings 924 extend into the recess 948 of the shuttling element 936, thereby coupling the shuttling element 936 to the needle 920, as shown in FIG. 31C. In this regard, the wings 924, and the shuttling element 936 may each define engagement features to allow the shuttling element 936 to be selectively coupled to the needle 920.

In another embodiment, and in reference to FIGS. 32A and 32B, an expandable needle head can be utilized instead of a deployable wire stop to detachably couple the shuttling element to the distal portion of the needle. As shown in FIG. 32A, the bi-directional suture instrument 10 may include a needle 950 having an expandable head 954 coupled to a shaft 956, and a sleeve-like wedge 958 disposed around the shaft 956 of the needle 950. The expandable head 954 of the needle 950 has two or more slots 962 cut into the proximal end of the needle head 954 that allow the needle head 954 to expand when biased. Either the shaft 956 of the needle 950 or the sleeve-like wedge 958 can be coupled to an actuation mechanism, to allow either the needle 950 or the sleeve-like wedge 958 to translate relative to the other.

In operation, the needle 950 may be advanced through a bore 966 of a shuttling element 970 when the head 954 is in an non-expanded state as shown in FIG. 32A. Once the head 954 is through the bore 966, the sleeve-like wedge 958 may be translated along the shaft 956 and into the slots 962 of the expandable needle head 954, thereby expanding the needle head 954, and providing a buttress against the distal end of the shuttling element 970 with the proximal end of the expandable needle head 954, as shown in FIG. 32B. Alternatively, the needle head 954 can extend into a recess formed in a bore of the shuttling element 970. In this regard, the needle head 954, and shuttling element 970 may each define engagement features to allow the shuttling element 970 to be selectively coupled to the needle 950.

Figure 33A:
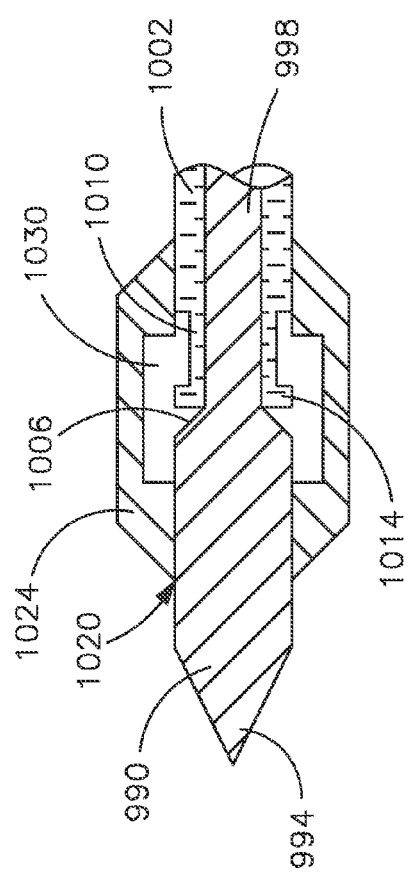
FIG. 33A is a partial side cross-sectional view of another embodiment of the bi-directional suture passing instrument, in which an expandable sleeve is used to detachably couple the shuttling element to the needle.
Figure 33B:
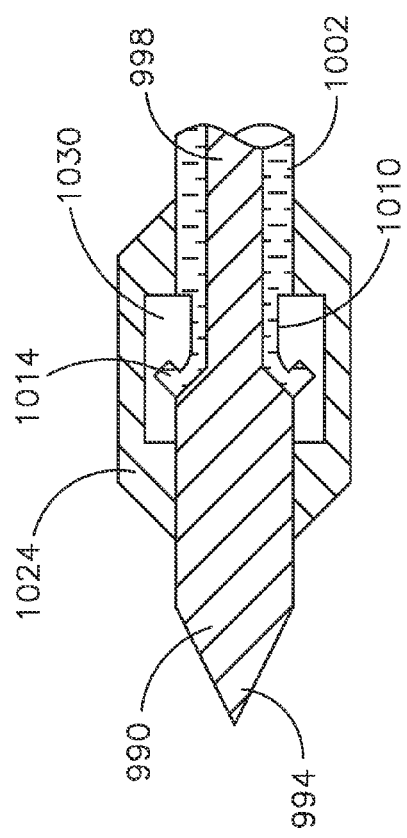
FIG. 33B is a partial side cross-sectional view of the instrument illustrated in FIG. 33A, showing the expandable sleeve deployed by forcing it against the proximal end of the needle head, to thereby couple the shuttling element to the needle.

In another embodiment, and in reference to FIGS. 33A and 33B, an expandable sleeve can be utilized instead of a deployable wire stop to detachably couple the shuttling element to the distal portion of the needle. As shown in FIG. 33A, the bi-directional suture instrument 10 may include a needle 990 having a head 994 extending from a shaft 998, and a sleeve 1002 disposed around the shaft 998 of the needle 990. As shown, the proximal side of the head 994 includes a chamfered surface 1006 that interacts with the sleeve 1002. The distal end of the sleeve 1002 has axial slits that define deflectable arms 1010 that are capable of deflecting when biased forward. Each arm 1010 includes a protrusion 1014 that extends radially outward. Either the shaft 998 or the sleeve 1002 can be coupled to an actuation mechanism to thereby allow either the shaft 998 or sleeve 1002 to translate relative to the other.

In operation, the needle 990 may be advanced through a bore 1020 of a shuttling element 1024 as shown in FIG. 33A. Once the head 994 of the needle 990 is properly placed in the bore 1020, the sleeve 1002 may be translated along the shaft 998 to thereby cause the deflectable arms 1010 of the sleeve 1002 to ride up the chamfered surface 1006, as shown in FIG. 33B. When the arms 1010 are deflected, the protrusions 1014 of the arms 1010 extend into a recess 1030 formed in an internal surface of the bore 1020 thereby coupling the shuttling element 1024 to the needle 990. In this regard, the deflectable arms 1010, and shuttling element 1024 may each define engagement features to allow the shuttling element 1024 to be selectively coupled to the needle 990. It should be understood, however that the protrusions 1014 of the arms 1010 may extend to form a buttress against the distal end of the shuttling element 1024.

In another embodiment, and in reference to FIGS. 34A-34D, the sleeve may be expandable by retracting the sleeve from an undercut formed in the needle. As shown in FIG. 34A, the bi-directional suture instrument 10 may include a needle 1050 having a head 1054 extending from a shaft 1058, and a sleeve 1062 disposed around the shaft 1058 of the needle 1050. As shown, the shaft 1058 includes a taper 1066 at its distal end, creating and undercut 1070 with the proximal end of the head 1054. The sleeve 1062 includes a bore 1074 having a taper 1078 at its distal end to form a head 1080 that is configured to engage the undercut 1070 formed in the needle 1050, as shown in FIG. 34A. Either the shaft 1058 or the sleeve 1062 can be coupled to an actuation mechanism to thereby allow either the shaft 1058 or sleeve 1062 to translate relative to the other.

In operation, the needle 1050 may be advanced through a bore 1082 of a shuttling element 1086 as shown in FIG. 34A. Once the head 1054 of the needle 1050 is properly placed in the bore 1082, the sleeve 1062 may be translated backward along the shaft 1058 to disengage the head 1080 of the sleeve 1062 from the undercut 1070 thereby causing the head 1082 of the sleeve 1062 to ride up the shaft 1058, as shown in FIG. 34B. When the sleeve 1062 is retracted, the head 1082 of the sleeve 1062 extends into a recess 1090 formed in an internal surface of the bore 1082 thereby coupling the shuttling element 1086 to the needle 1050. In this regard, the sleeve 1062, and shuttling element 1086 may each define engagement features to allow the shuttling element 1086 to be selectively coupled to the needle 1050. It should be understood, however that the head 1082 of the sleeve 1062 may extend to form a buttress against the distal end of the shuttling element 1086.

As shown in FIGS. 34A and 34B, the head 1080 of the sleeve 1062 may include a peak 1098 that engages the recess 1090 of the shuttling element 1086. As shown in FIG. 34A, when the head 1080 of the sleeve 1062 is interfacing with the undercut 1070 the outer surface of the head 1054 of the needle 1050 is aligned with the outer surface of the sleeve 1062. Alternatively, the head 1080 of the sleeve 1062 may include a protrusion 1102 that engages the recess 1090 of the shuttling element 1086, as shown in FIGS. 34C and 34D. In any of the above expandable sleeve embodiments, the expandable sleeves may have additional buttressing features such as one or more teeth. Those skilled in the art will appreciate that additional buttressing features are preferably rectangular but could be flat, round, triangular, or any other shape currently known in the art. In an additional modification of the above embodiments, the distal tip of the expandable sleeve, including any additional buttressing features, may instead be deployed at a point distal to the shuttling element.

In another embodiment, and in reference to FIGS. 35A and 35B, an expandable split ring stop can be utilized instead of a deployable wire stop to detachably couple the shuttling element to the distal portion of the needle. As shown in FIG. 35A, the bi-directional suture instrument 10 may include a needle 1110 having a head 1114 extending from a shaft 1118, a sleeve 1122 disposed around the shaft 1118, and a split ring stop 1126 disposed around the shaft 1118 between the sleeve 1122 and the head 1114. The proximal side of the head 1114 has a chamfered surface 1132, and the distal end of the sleeve 1122 has a chamfered surface 1136 that each interface with corresponding chamfered surfaces 1140 of the split ring 1126. Either the shaft 1118 or the sleeve 1122 can be coupled to an actuation mechanism to thereby allow either the shaft 1118 or sleeve 1122 to translate relative to the other.

In operation, the needle 1110 may be advanced through a bore 1142 of a shuttling element 1144 as shown in FIG. 35A. Once the head 1114 of the needle 1110 is properly placed in the bore 1142, either the sleeve 1122 may be translated forward along the shaft 1118, or the needle 1110 may be translated backward within the sleeve 1122, forcing the split ring stop 1126 against the needle head 1114. As the sleeve 1122 is translated further forward, the chamfered surface 1136 of the sleeve 1122 and the chamfered surface 1132 of the needle head 1114 engage corresponding chamfered surfaces 1140 of the split ring stop 1126 forcing the split ring 1126 into a recess 1160 formed in an internal surface of the bore 1142 to thereby couple the shuttling element 1144 to the needle 1110, as shown in FIG. 35B. In this regard, the split ring stop 1126, and the shuttling element 1144 may each define engagement features to allow the shuttling element 1144 to be selectively coupled to the needle 1110. It should be understood that the edges of the split ring 1126 may have additional buttressing features such as one or more teeth. Those skilled in the art will appreciate that additional buttressing features are preferably rectangular but could be flat, round, triangular, or any other shape currently known in the art.

In another embodiment, and in reference to FIGS. 36A and 36B, an expandable cage can be utilized instead of a deployable wire stop to detachably couple the shuttling element to the distal portion of the needle. As shown in FIG. 36A, the bi-directional suture instrument 10 may include a needle 1200 having a head 1204 that extends from a shaft 1208, a sleeve 1212 disposed around the shaft 1208 of the needle 1200, and an expandable cage 1216 disposed around the shaft 1208 between the needle head 1204 and the sleeve 1212. The expandable cage 1216 is tube like and has two or more contained axial slots cut along the longitudinal axis of the tube such that the proximal and distal ends of the expandable cage 1216 are solid rings of material. Either the shaft 1208 or the sleeve 1212 can be coupled to an actuation mechanism to thereby allow either the shaft 1208 or sleeve 1212 to translate relative to the other.

In operation, the needle 1200 may be advanced through a bore 1220 of a shuttling element 1224 as shown in FIG. 36A. Once the head 1204 of the needle 1200 is properly placed in the bore 1220, the sleeve 1212 may be translated forward along the shaft 1208 to compress the expandable cage 1216 between the needle head 1204 and the sleeve 1212, thereby forcing the expandable cage 1216 to expand radially outward and into a recess 1232 formed in the bore 1220 of the shuttling element 1224, as shown in FIG. 36B. The expanded cage 1216 couples the shuttling element 1224 to the needle 1200. Alternatively, the needle 1200 may be retracted within the sleeve 1212 to radially expand the cage 1216, thereby coupling the shuttling element 1224 to the needle 1200. In this regard, the expandable cage 1216, and the shuttling element 1224 may each define engagement features to allow the shuttling element 1224 to be selectively coupled to the needle 1200.

The expandable cage may have additional buttressing features and configurations. For example, the expandable cage 1216 may include a protrusion 1233 that engages the recess of the shuttling element, as shown in FIGS. 37A and 37B. Those skilled in the art will appreciate that the additional buttressing features are preferably rectangular but could be flat, round, triangular, or any other shape currently known in the art. Furthermore, the expandable cage 1216 may include an expandable portion 1234 that may be deployed into the recess of the shuttling element, as shown in FIGS. 38A and 38B. As shown, the expandable portion 1234 is formed proximate to the middle of the cage 1216. The expandable portion 1234 is a portion of the cage 1216 that protrudes radially outward when the cage 1216 is compressed.

In another embodiment, and in reference to FIGS. 39A and 39B, a deployable rotating elliptical needle tip can be utilized to detachably couple the shuttling element to the distal portion of the needle. As shown in, the bi-directional suture instrument 10 may include a needle 1270 having an elliptical head 1274 that extends from a shaft 1278, and a sleeve 1282 disposed around the shaft 1278. Though not required, the shaft 1278 may be cylindrical and is rotatable within the sleeve 1282. The elliptical head 1274 has a small diameter side 1286 and a large diameter side 1290.

In operation, the needle 1270 may be advanced through an elliptical bore 1294 of a shuttling element 1298 as shown in FIG. 39A. As shown, the small diameter side 1286 has a diameter that is less than the diameter of the bore 1294. Once the head 1274 of the needle 1270 is through the bore 1294, the needle 1270 and thus the elliptical head 1274 are rotated 90 degrees, via an actuation mechanism, so that the shuttling element 1298 can be trapped between the large diameter side 1290 of the needle head 1274 and a buttress 1302 formed on an external surface of the sleeve 1282, as shown in FIG. 39B. The trapped shuttling element 1298 will then be coupled to the needle 1270. In this regard, the elliptical head 1274, buttress 1302, and the shuttling element 1298 may each define engagement features to allow the shuttling element 1298 to be selectively coupled to the needle 1270. It can be appreciated by those skilled in the art that any oblong shape, such as a rectangle, diamond, etc., could be used in place of an elliptical shape for the needle head, the sleeve, and the shuttling element.

Figure 40B:
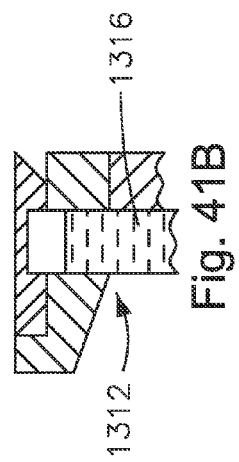

The boom arm housing of the bi-directional suture passer 10, may include configurations other than the one described in FIGS. 20A-20D. For example, in another embodiment, and in reference to FIGS. 40A and 40B, a spring loaded transverse member may be utilized rather than an elastomeric member to retain the shuttling element in the boom arm housing. As shown in FIG. 40A, the bi-directional suture instrument 10 may include a boom arm housing 1300 having a body 1304, a bore 1308 extending through the body 1304, and a locking interface 1312. As shown in FIG. 40A, the locking interface 1312 includes a transverse member 1316 having a bore 1320. The member 1316 is spring loaded so that it can be biased between a locked position, in which the bore 1320 of the member 1316 is not aligned with the bore 1308 of the housing body 1304, and an unlocked position, in which the bore 1320 of the member 1316 is aligned with the bore 1308 of the housing body 1304. As shown in FIG. 40A, when the member 1316 is in the unlocked position, a shuttling element 1330 can enter the boom arm housing 1300. As shown in FIG. 40B, when the member 1316 is in the locked position, a portion 1338 of the member 1316 engages a back side of the shuttling element 1330 to thereby retain the shuttling element within the boom arm housing 1300. An actuation mechanism may be used to selectively bias the member 1316 between the locked and unlocked positions.

The locking interface 1312 may be located near the proximal end of the boom arm housing 1300, as shown in FIGS. 40A and 40B, or substantially in the middle of the boom arm housing 1300 as shown in FIGS. 41A and 41B. If the locking interface 1312 is located proximate to the middle as shown in FIGS. 41A and 41B, then the shuttling element 1330 may include a recess 1342 that is configured to be engaged by the portion 1338 of the member 1316 when the locking interface 1312 is in the locked position, as shown in FIG. 41B.

In another embodiment, and in reference to FIGS. 42A and 42B, a flexible polymeric tube with an internal rope mechanism may be utilized rather than an elastomeric member to retain the shuttling element in the boom arm housing. As shown in FIG. 42A, the bi-directional suture instrument 10 may include a boom arm housing 1350 having a body 1354, a bore 1358 extending through the body 1354, and a locking interface 1362. As shown in FIG. 42A the locking interface 1362 includes a flexible polymeric tube 1366 with an internal rope mechanism 1370. The flexible polymeric tube rests within an internal groove or recess 1374 formed in an internal surface of the bore 1358. Once a shuttling element 1378 has advanced past the recess 1374, the flexible polymeric tube 1366 is contracted by pulling the internal rope 1370 to provide a buttress against the proximal end of the shuttling element 1378, as shown in FIG. 42B. The needle may then be retracted and the shuttling element 1378 will remain behind in the boom arm housing 1350.

The locking interface 1362 may be located near the proximal end of the boom arm housing 1350, as shown in FIGS. 42A and 42B, or substantially in the middle of the boom arm housing 1350 as shown in FIGS. 43A and 43B. If the locking interface 1362 is located proximate to the middle as shown in FIGS. 43A and 43B, then the shuttling element 1378 may include a recess 1382 that is configured to be engaged by the flexible polymeric tube 1366 when the internal rope 1370 has been contracted, as shown in FIG. 43B.

In another embodiment, and in reference to FIGS. 44A-44D, a c-clip may be utilized rather than an elastomeric member to retain the shuttling element in the boom arm housing. As shown in FIG. 44A, the bi-directional suture instrument 10 may include a boom arm housing 1400 having a body 1404, a bore 1408 extending through the body 1404, and a locking interface 1412. As shown in FIGS. 44C and 44D, the locking interface 1412 includes a c-clip 1416 having protrusions 1420 at its distal ends. As shown in FIG. 44A, the c-clip 1416 rests within an external groove or recess 1424 formed in the housing body 1404 such that the protrusions 1420 extend into the bore 1408. The c-clip 1416 acts as a spring and expands, as shown in FIG. 44C, to allow a shuttling element 1428 to pass through the c-clip 1416, as shown in FIG. 44A. Once the shuttling element 1428 has advanced past the c-clip 1416, the c-clip 1416 contracts and the protrusions 1420 on the ends of the c-clip 1416 act as a buttress against the proximal end of the shuttling element 1428, as shown in FIG. 44B. The needle may then be retracted and the shuttling element 1428 will remain behind in the boom arm housing 1400.

The locking interface 1412 may be located near the proximal end of the boom arm housing 1400, as shown in FIGS. 44A and 44B, or substantially in the middle of the boom arm housing 1400 as shown in FIGS. 45A and 45B. If the locking interface 1412 is located proximate to the middle as shown in FIGS. 45A and 45B, then the shuttling element 1420 may include a recess 1432 that is configured to be engaged by the protrusions 1420 of the c-clip 1416 when the c-clip 1416 has been contracted, as shown in FIG. 45B.

In another embodiment, and in reference to FIGS. 46A and 46B, a leaf spring finger may be utilized rather than an elastomeric member to retain the shuttling element in the boom arm housing. As shown in FIG. 46A, the bi-directional suture instrument 10 may include a boom arm housing 1450 having a body 1454, a bore 1458 extending through the body 1454, and a locking interface 1462. The locking interface 1462 is a leaf spring finger 1466 having an arm 1470 extending from a front wall 1474 of the body 1454, and a protrusion 1478 extending up from the arm 1470. The finger 1466 is deflectable and biases down into a recess 1482 defined by an internal surface of the bore 1458 as a shuttling element 1486 advances into the bore 1458. Once the shuttling element 1486 has advanced past the protrusion 1478, the finger 1466 biases up, and the protrusion 1478 acts as a buttress against the proximal end of the shuttling element 1486, as shown in FIG. 46B. The needle may then be retracted and the shuttling element 1486 will remain behind in the boom arm housing 1450.

The locking interface 1462 may be located near the proximal end of the boom arm housing 1450, as shown in FIGS. 46A and 46B, or substantially in the middle of the boom arm housing 1450 as shown in FIGS. 47A and 47B. If the locking interface 1462 is located proximate to the middle as shown in FIGS. 47A and 47B, then the shuttling element 1486 may include a recess 1490 that is configured to be engaged by the protrusion 1478 of the finger 1466 when the finger 1466 is biased upwards, as shown in FIG. 47B.

In another embodiment, and in reference to FIGS. 48A and 48B, a wire buttress may be utilized rather than an elastomeric member to retain the shuttling element in the boom arm housing. As shown in FIG. 48A, the bi-directional suture instrument 10 may include a boom arm housing 1500 having a body 1504, a bore 1508 extending through the body 1504, and a locking interface 1512. The locking interface 1512 is a wire stop 1516 that is manually extended from a bore 1518 into the bore 1508 to act as a buttress against the proximal end of a shuttling element 1520. Once the shuttling element 1520 has advanced past the bore 1518, the wire 1516 is deployed by advancing the wire 1516 above the shuttling element 1520 thereby providing a buttress against the proximal end of the shuttling element 1520, as shown in FIG. 48B. The needle may then be retracted and the shuttling element 1520 will remain behind in the boom arm housing 1500.

The locking interface 1512 may be located near the proximal end of the boom arm housing 1500, as shown in FIGS. 48A and 48B, or substantially in the middle of the boom arm housing 1500 as shown in FIGS. 49A and 49B. If the locking interface 1512 is located proximate to the middle as shown in FIGS. 49A and 49B, then the shuttling element 1520 may include a recess 1524 that is configured to be engaged by the wire 1516 when the wire 1516 is extended, as shown in FIG. 49B. The wire 1516 may be any shape including cylindrical, square, etc.

In another embodiment, and in reference to FIGS. 50A and 50B, a spring loaded gate may be utilized rather than an elastomeric member to retain the shuttling element in the boom arm housing. As shown in FIG. 50A the bi-directional suture instrument 10 may include a boom arm housing 1550 having a body 1554, a bore 1558 extending through the body 1554, and a locking interface 1562. The locking interface 1562 includes a gate 1566 that is biased upwards by a spring 1570. As shown, the gate 1566 includes an angled surface 1574 at its upper end, and extends partially into the bore 1558 when it is biased upwards. The gate 1566 acts as a buttress against the proximal end of a shuttling element. In operation, the needle or shuttling element contact the angled surface 1574 of the gate 1566 to thereby bias it downwards. As the gate is biased down, the shuttling element may enter the bore 1558, and once fully in, the gate 1566 may be biased upwards by the spring 1570 to thereby couple the shuttling element to the boom arm housing 1550. The needle may then be retracted, while the shuttling element remains behind in the boom arm housing 1550.

In another embodiment, and in reference to FIGS. 51A-51E, a series of grooves and traps may be utilized to detachably couple the shuttling element to the needle, and detachably couple the shuttling element to the boom arm housing. As shown, the bi-directional suture instrument 10 may include a tube-like shuttling element 1600 having a body 1604 defining a bore 1608 that is engaged by a needle 1612. The needle 1612 includes a body 1616 having engagement features such as a plurality of external ribs 1620 extending up from the body 1616, and a plurality of triangular traps 1624 formed in the body 1616 proximal to the ribs 1620. The traps 1624 are spaced apart from the ribs 1620 a distance to allow the shuttling element 1600 to rest on the body 1616. The body 1604 of the shuttling element 1600 includes axial slots 1628 that are configured to align with each rib 1620 of the needle 1612. A plurality of ribs 1632 extend from an external surface of the body 1604 and are aligned with the slots 1628. The shuttling element 1600 also includes triangular traps 1640 formed on the proximal and distal ends of the shuttling element body 1604. The traps 1640 on the distal end of the shuttling element 1600 are offset from the ribs 1620 of the needle 1612 and are biased to accept and capture the proximal tips of the ribs when it is desirable for the shuttling element 1600 to be coupled to the needle 1612. The needle 1612 and the coupled shuttling element 1600 may then be advanced to the boom arm housing.

The boom arm housing 1650 includes a body 1654 that defines a bore 1658. The bore 1658 defines axial slots that are configured to align with external ribs 1632 of the shuttling element 1604. Within the bore 1658 of the housing 1650 is a counter force element, such as a spring, that is configured to interact with the distal tip of the shuttling element 1600 and the distal tip of the needle 1612. The counterforce element includes a series of axial slots and triangular traps that are configured to interact with the external ribs 1620 of the needle 1612, and a preferably flat surface that is configured to interact with the distal end of the shuttling element 1604. Additionally, the boom arm housing 1650 includes a series of triangular traps that are located distal to the axial slots within the bore 1658 that are configured to interact with the triangular traps on the proximal end of the shuttling element 1604.

In operation, the shuttling element 1604 enters the bore 1658 of the boom arm housing 1650 by aligning the external ribs 1632 of the shuttling element 1604 with the axial slots of the housing 1650. As the needle 1612 is advanced further the external ribs 1620 on the needle 1612 align with the axial slots in the counterforce element, allowing the needle 1612 to advance through the counterforce element. Simultaneously the shuttling element 1604 is advanced past the axial slots within the boom housing 1650 and encounters the flat surface of the counter-force element, which pushes the shuttling element 1604 toward the proximal end of the boom tip, causing the shuttling element 1604 to rotate as the triangular traps 1640 on the proximal ends of the shuttling element 1604 interact with and are captured by the triangular traps on the distal end of the axial slots within the boom housing 1650. This rotation of the shuttling element 1604 aligns the axial slots 1628 within the shuttling element 1604 with the axial slots of the counterforce element and the external ribs 1620 of the needle 1612, allowing the needle 1612 to be freely retracted from the boom arm housing 1650 and retracted into the protective sheath embodied by the body, leaving the shuttling element 1604 detachably coupled to the distal boom housing 1650, thereby maintaining the shuttling element 1604 and connected suture strand on the underside of the tissue adjacent the defect.

The boom arm is then manipulated, e.g., rotated, with the needle 1612 safely shielded, to another area on the underside of the tissue adjacent the defect, e.g., on an opposite underside of the defect, and, once optimally relocated, the needle 1612 is translated distally again with respect to the handle using the thumb ring and maintaining the thumb ring lock and thumb ring lock cap in an unlocked position, thereby forcing the needle 1612 to pass through from the top side to the underside of the tissue at a second site adjacent to the defect and cause the distal end of the needle 1612 to re-engage the shuttling element 1604. The external ribs 1620 on the needle 1612 translate within the axial slots 1628 on the interior of the shuttling element 1604 in a distal motion. As the needle 1612 is further advanced the triangular traps 1624 on the proximal side of the distal end of the needle 1612 contact the triangular traps 1640 on the proximal end of the shuttling element 1604 and engage the shuttling element 1604, causing the shuttle 1604 to rotate. In this rotated position the external ribs 1620 on the needle 1612 are no longer aligned with the axial slots 1628 on the interior of the shuttling element 1604 and are instead aligned with the triangular traps 1640 on the distal end of the shutting element 1604, allowing the shuttling element 1604 to be recaptured by the needle 1612, thereby coupling the shuttling element 1604 to the needle 1612 upon retraction of the needle 1612.

In another embodiment, and in reference to FIGS. 52A-52L, threaded engagement features and threaded locking interfaces may be utilized to detachably couple the shuttling element to the needle, and detachably couple the shuttling element to the boom arm housing. As shown in FIGS. 52A and 52B, the bi-directional suture instrument 10 may include a cannulated needle 1670, and a dual ended shuttling element 1674 that is selectively coupled to the needle 1670. The needle 1670 includes a body 1678 having a bore or channel 1682 extending through the body 1678. The distal end of the bore 1682 includes an engagement feature such as internal threads 1686. Detachably coupled to the distal end of the needle 1670 is the shuttling element 1674.

The shuttling element 1674 includes a body 1690 that defines a radial groove 1694 for fastening a suture to the shuttling element 1674, a first head 1698 extending rearward from the body 1690, and a second head 1702 extending forward from the body 1690. The first head 1698 includes an engagement feature such as external threads 1706 that are configured to engage the internal threads 1686 of the needle 1670. The second head 1702 includes a locking mechanism, such as external threads 1710 and a needle point 1714 forward of the external threads 1710. The external threads 1706 and the external threads 1710 have opposite threads. For example, external threads 1706 are left handed threads, and external threads 1710 are right handed threads, which will allow the needle 1670 to become detached from the shuttling element 1674. The internal and external threads may have different pitches.

The shuttling element 1674 is preferably decoupleable from the needle 1670 within a boom arm housing, such as boom arm housing 1718, via actuation of a tip actuator. Boom arm housing 1718 includes a body 1722 having a bore 1726 that extends therethrough. The distal end of the bore 1726 includes a locking interface, such as internal threads 1730 that are configured to engage the external threads 1710 of the shuttling element 1674. The proximal end of the shuttling element 1674 includes a gap 1740 to create clearance for the suture that is attached to the shuttling element 1674.

In operation, an operator engages the shuttling element 1674 with attached suture onto the needle 1670 and, optionally, places the suture through a suture tensioner. An operator grasps the handle with his index and middle finger and disposes his thumb through the thumb ring, with the actuator in a position retracted proximally from the handle. The distal portion of the boom arm is placed through a tissue defect, such as a fissure through the annulus fibrosis of an intervertebral disc, from a top side of the tissue to an underside of the tissue, and is rotated or otherwise positioned adjacent the defect in an optimum configuration for passing a suture adjacent to the tissue defect for the purposes of approximating the defect. The thumb ring is translated distally with respect to the handle, thereby advancing the actuator and the needle 1670 distally with respect to the handle and causing the distal end of the needle 1670 and the shuttling element 1674 attached thereto, as well as the suture attached to the shuttling element 1674, to pass through the tissue adjacent to the defect and force contact to be made between the shuttling element 1674 and the boom arm housing 1718. When the distal tip of the shuttling element 1674 contacts the proximal end of the internal threads 1674 of the boom arm housing 1718, the tip actuator is actuated (i.e. right hand turning) causing the needle 1670 and shuttling element 1674 to be rotated, thereby engaging the external threads 1710 of the shuttling element 1674 with the internal threads 1674 of the boom arm housing 1718. Further rotation of the needle 1670 cause a decoupling of the threaded shuttling element 1674 from the needle 1670, leaving the shuttling element 1674 coupled to the boom arm housing 1718. In other words, at some point, as the needle 1670 is rotated, the shuttling element 1674 stops rotating in the boom arm housing 1718, and the needle 1670 continues to rotate causing the needle 1670 to disengage from the shuttling element 1674. This disengagement is enabled because of the opposite threading of the external threads 1706 and external threads 1710 of the shuttling element 1674.

The needle 1674 is then retracted into the protective sheath embodied by the body. The boom arm is then manipulated., e.g., rotated, with the needle 1670 safely shielded, to another area on the underside of the tissue adjacent the defect, e.g., on an opposite underside of the defect, and, once optimally relocated, the needle 1670 is translated distally again with respect to the handle using the thumb ring, thereby forcing the needle 1670 to pass through from the top side to the underside of the tissue at a second site adjacent to the defect and cause the distal end of the needle 1670 to contact the proximal edge of the external threads 1706 of the shuttling element 1674. The tip actuator is then re-actuated (i.e. left hand turning), causing the needle 1670 to rotate in the opposite direction, thereby engaging the internal threads 1686 of the needle 1670 with the external threads 1706 on the proximal end of the shuttling element 1674, and coupling the shuttling element 1674 to the needle 1670. Further rotation of the needle 1670 causes the shuttling element 1674 to decouple from the boom arm housing 1718. The thumb ring is then retracted proximally with respect to the handle, causing the corresponding retraction of the actuator and the needle 1670, and thereby causing the distal end of the needle 1670 and the shuttling element 1674 with suture to pass from the underside of the tissue adjacent the defect out through the topside of the tissue adjacent the defect. The steps can be repeated one or more times as desired, depending on the size of the defect and the characteristics of the tissue.

In another embodiment, and in reference to FIGS. 53A-53C, the needle includes external threads rather than internal threads. As shown in FIG. 53A, the bi-directional suture instrument 10 may include a needle 1750, and a shuttling element 1754 that is selectively coupled to an exterior surface of the needle 1750. The needle 1750 includes a body 1758 having an engagement feature such as external threads 1766 proximate to its distal end. Detachably coupled to the distal end of the needle 1750 is the shuttling element 1754.

The shuttling element 1754 includes a body 1770 having an axial bore 1774 extending therethrough. As shown, the bore 1774 includes an engagement feature, such as internal threads 1778 that are configured to engage the external threads 1766 of the needle 1750. The shuttling element body 1754 also includes a locking mechanism, such as external threads 1780. The internal threads 1778 and the external threads 1780 have opposite threads. For example, internal threads 1778 are left handed threads, and external threads 1780 are right handed threads, which will allow the needle 1670 to become detached from the shuttling element 1674.

The shuttling element 1754 is preferably decoupleable from the needle 1750 within a boom arm housing, such as boom arm housing 1784, via actuation of a tip actuator. Boom arm housing 1784 includes a body 1788 having a bore 1792 that extends therethrough. The bore 1792 includes a locking interface, such as internal threads 1796 that are configured to engage the external threads 1780 of the shuttling element 1754. The shuttling element 1754 may be coupled to the boom arm housing 1784, as shown in FIGS. 53B and 53C in a similar manner as the embodiment described in reference to FIGS. 52A-52L. It should be understood, that the shuttling element 1754 is not limited to the configuration described, and may be dual ended as described in FIGS. 52A-52L, with the first head having a bore that defines internal threads configured to engage the external threads 1766 of the needle 1750.

In another embodiment, and in reference to FIGS. 54A-54N, wings may be utilized rather than threads to detachably couple the needle to the shuttling element, and the shuttling element to the boom arm housing. As shown, the bi-directional suture instrument 10 may include a winged needle 1800 that is detachably coupled to a winged shuttling element

1804. As shown, the needle 1800 includes a body 1808 having an engagement feature, such as wings 1812 extending radially outward from an external surface of the body 1808 adjacent a distal top of the needle 1800. Each wing 1812 includes an angled front surface 1816. As shown, the wings 1812 extend on opposite sides of the needle body 1808 and are configured to engage the shuttling element 1804.

The shuttling element 1804 includes a body 1820 having a locking mechanism such as wings 1824 extending radially outward from an external surface of the body 1820 adjacent a needle like distal end 1828, and a bore 1832 extending into the body 1820 from the proximal end of the body 1820. Each wing 1824 includes an angled front surface 1830 to allow the shuttling element 1804 to easily pass through tissue. The shuttling element 1804 includes a bore 1832 having a pair of axial slots 1836 that lead into an engagement feature, such as radial slots 1840, which are configured to be engaged by wings 1812 of the needle 1800 to detachably couple the shuttling element 1804 to the needle 1800.

The shuttling element 1804 and needle 1800 may be advanced into a boom arm housing, such as boom arm housing 1850. As shown, the boom arm housing 1850 is similar to the proximal end of the shuttling element 1804. In other words, the boom arm housing 1850 includes a bore 1854 that defines axial slots 1858 to lead into a locking interface, such as radial slots 1862, which are configured to be engaged by wings 1824 of the shuttling element 1804.

In operation, the needle 1800 is coupled to the shuttling element 1804 by aligning the wings 1812 with the axial slots 1836 of the shuttling element 1804. The needle 1800 is then advanced through the slots 1836 and into the radial slots 1840. The needle is then rotated 180 degrees (right hand turning) and the interface between the wings 1812 and the radial slots 1840 couples the shuttling element 1804 to the needle 1800. The shuttling element 1804 and the needle 1800 are then translated toward the boom arm housing 1850. The shuttling element 1804 engages the boom arm housing 1850 by aligning the wings 1824 of the shuttling element 1804 with the axial slots 1858 of the boom arm housing 1850. The shuttling element 1804 is further advanced until the wings 1824 engage the radial slots 1862 of the boom arm housing 1850. The needle 1800 with the shuttling element 1804 are then rotated to thereby selectively couple the shuttling element 1804 to the boom arm housing 1850. The needle 1800 may then be retracted thereby leaving the shuttling element 1804 in the boom arm housing 1850. The steps can be repeated one or more times as desired, depending on the size of the defect and the characteristics of the tissue.

Alternatively the engagement features of the embodiment shown in FIGS. 54A-54N may be reversed. For example, as shown in FIG. 55 the bi-directional suture passing instrument 10 may include a needle 1870, that is detachably coupled to a shuttling element 1874. As shown, the needle 1870 includes a body 1878 having an engagement feature, such as a recess 1882 extending radially inward from an external surface of the body 1878. The recess 1882 extends proximally to a radial slot 1886 that defines a back wall 1890. As shown, the recess 1882 is configured to engage the shuttling element 1874.

The shuttling element 1874 includes a body 1894 having a bore 1898 and a locking mechanism that is substantially identical to the engagement feature of the needle 1870. The bore 1898 includes an axial protrusion that define an engagement feature, such as a radial slot, that is configured to be engaged by the recess and back wall of the needle 1870 to thereby detachably couple the shuttling element 1874 to the needle 1870.

The shuttling element 1874 and needle 1870 may be advanced into a boom arm housing, such as boom arm housing 1906. As shown, the boom arm housing 1906 is similar to the proximal end of the shuttling element 1874. In other words, the boom arm housing 1906 includes a bore 1910 that defines an axial protrusion 1912 that define an engagement feature, such as a radial slot, that is configured to be engaged by the recess and back wall of the shuttling element 1874 to detachably couple the shuttling element 1874 to the boom arm housing 1906.

As shown in FIGS. 56A-56D, the bi-directional suture passer 10 may include other features and designs. For example, as shown in FIG. 56A, the bi-directional suture passer 10 may include a handle 1920 a member 1924 extending through the handle 1920, and a boom arm 1928 extending from an end of the member 1924. The bi-directional suture passer 10 may also include a driver 1932 translatable within a bore of the member 1924. As shown in FIG. 56B, the driver 1932 includes a knob 1936, a shaft 1940 extending from the knob 1936, and a needle 1944 extending from a distal end of the shaft 1940. The needle 1944 is similar to the needle described in reference to FIGS. 53A-53C and includes an engagement feature comprising externally extending threads 1948 for coupling the needle 1944 to a shuttling element such as shuttling element 1950 shown in FIG. 53C. The threads of the needle 1944 and shuttling element 1944 may engage each other either in a ratcheting type connection or a rotation type connection.

As shown in FIG. 56C the shuttling element includes a body 1951 having a needle engaging portion 1952 and a tissue engaging portion 1953. As shown, the needle engaging portion 1953 includes a bore 1954 having an internal surface that defines an engagement feature such as threads. The threads of the needle engaging portion 1953 are configured to engage the threads 1948 of the needle 1944 to detachably couple the needle 1944 to the shuttling element 1950. As shown, the tissue engaging portion 1953 extends distally and includes a locking mechanism such as external threads 1955. Threads 1955 are configured to engage a locking feature defined by a boom arm housing 1956 (shown in FIG. 56D) of the boom arm 1928.

As shown in FIG. 56D, the boom arm housing 1956 has a bore 1960 extending therethrough. The bore 1960 has an internal surface that defines internal threads 1964. The boom arm 1928 also includes slots 1970 that extend through the body of the boom arm 1928. The slots 1970 allow the boom arm housing 1956 to separate slightly when the shuttling element 1950 is being disposed within the bore 1960. Therefore, for embodiments that utilize threads, the amount of turning may be reduced because the shuttling element may be ratcheted in. To remove the shuttling element from the boom arm housing 1956, the shuttling element may be turned or rotated to unthread the shuttling element form the boom arm housing 1956.

In reference to FIG. 57A-57E, the bi-directional suture passing instrument 10 may be configured to create a pathway in a bony structure through which the suture can be passed. As shown, the bi-directional suture instrument 10 may include a boom arm 2000 having an awl tip 2004 configured to allow the boom arm 2000 to create a pathway in a bony structure through which the suture can be passed. Alternatively, the bi-directional suture instrument 10 may include a needle 2008 having an awl tip 2012 configured to enable the tip of the needle 2008 to create a pathway in a bony structure through which the suture can be passed. It should be understood that both the boom arm and the needle can include an awl tip.

As shown in FIG. 57B, an impaction rod 2016 may be attached to the instrument 10, and may be configured to contact an impact wall formed on the boom arm 2000. Alternatively, the impaction rod 2016 may include grips 2020, as shown in FIGS. 57C-57E, that are configured to grip and hold the needle 2008 when the needle 2008 is to be impacted. A bi-directional suture passing instrument 10 having such features may be used to repair annulus rim tears.

The bi-directional suture instrument 10 may be used to repair soft tissue defects using a variety of different suture passing configurations, such as those illustrated in FIGS. 58A-58F. For example a simple stitch 2100 as shown in FIG. 58A, a box mattress stitch 2104 as shown in FIG. 58B, a mattress stitch 2108 as shown in FIG. 58C, a reverse mattress stitch 2112 as shown in FIG. 58D, a vertical mattress stitch 2116 as shown in FIG. 58E, and a reverse vertical mattress stitch 2120 as shown in FIG. 58F. The final configuration of suture surrounding the defect may be a single straight loop, a mattress stitch or combination of mattress stitches, or may include a loop comprising any of a number of stitch patterns for soft tissue repair known to the art of arthroscopic, laparoscopic, orthopedic, cardiovascular, or general surgery.

As shown in FIG. 58A, the simple stitch 2100 is formed by passing the suture through the full thickness of tissue on one side of a defect and retrieved through the full thickness of tissue on the other side of the defect. The suture may first be passed from inside to outside (i.e., a first side to a second side of the tissue), and then retrieved from outside to inside (i.e., a second side to a first side) of the tissue, or may first be passed from outside to inside then inside to outside of the tissue. Any combination of outside-to-inside and inside-to-outside passes may be used.

As shown in FIG. 58B, the box stitch 2104 is formed by passing the suture horizontally across the defect and then from the proximal side of the disc to the distal side of the disc. The suture is then passed back across the defect and the free end of the suture is then tied into a knot to complete the stitch. The knot sits on the outside of the annulus defect.

As shown in FIG. 58C, the mattress stitch 2108 is formed by passing the suture from the proximal side of the disc to the distal side of the disc, and then across the defect at an angle toward the proximal side of the disc. The steps are repeated and the free end of the suture is then tied into a knot to complete the stitch. The knot sits on the outside of the annulus defect. As shown in FIG. 58D, the knot sits o the inside of the annulus wall below the defect for a zero profile closure for the reverse mattress stitch 2112.

As shown in FIGS. 58E and 58F, the vertical mattress stitch and the reverse vertical mattress stitch may be formed by passing the suture across the defect on the proximal side of the disc, and then across the defect at an angle toward a distal side of the disc. The steps are repeated and the stitch is completed. As shown, the knot may be either outside of the annulus defect, as shown in FIG. 58E, or inside of the defect as shown in FIG. 58F.

The bi-directional suture instrument 10 may also be configured to pass a suture for soft tissue repair near a bony element, such as a vertebral body, is shown in FIGS. 58G-58I. As shown, a free end 2200 of the suture is passed through the full thickness of the annulus wall on the side of the defect furthest away from the vertebral body nearest the defect and then passed through a hole that is formed through the vertebral body via a transosseus approach next to the defect. The hole can be created using an awl tip or awl tipped needle as described above in reference to FIG. 57A-57D, or can be predrilled. The suture may first be passed through the vertebral body and then through the full thickness of the annulus.

Such a method may also be configured for other soft tissues adjacent a bony element, such as reattachment of torn rotator cuff tendons to the lesser tuberosity of the humerus.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description. For example, other engagement features may be utilized to detachably connect the needle to the shuffling element and other mechanisms may be utilized to detachably connect the shuttling element to the boom arm housing, such as a Morse taper coupling, a magnetic hold, a press fit coupling, and a variety of other mechanical connections known in the art. Furthermore, any features of one described embodiment can be applicable to the other embodiments described herein. For example, each shuffling element described, may be tubular and capable of fitting over the needle, or each may include a needle like tip with a proximal end configured to be coupled to the needle.

What is claimed:

1. A bi-directional suture passing instrument configured to approximate soft tissue defects, the suture passing instrument comprising:
   a body member defining a needle receiving channel;
   a boom arm extending from the body member, the boom arm having a boom arm housing that is spaced from the body member, wherein a tissue-receiving gap is disposed between the boom arm housing and the body member;
   a needle reciprocally translatable within the channel of the body member between an advanced position in which a distal end of the needle extends into the boom arm housing, and a retracted position in which the distal end of the needle is refracted from the boom arm housing, the needle defining a tip that is configured to penetrate tissue; and
   a shuttling element configured to detachably couple to the needle, and to the boom arm housing, the shuttling element defining a needle-like tip such that when the shuttling element is detachably coupled to the needle and the needle is translated toward the advanced position the needle-like tip of the shuttling element is configured to penetrate tissue that is disposed within the tissue-receiving gap, so that the shuttling element can pass through the tissue and into the boom arm housing,
   wherein (i) when the shuttling element is detachably coupled to the needle, rotation of the needle relative to the boom arm housing causes the shuttling element to detachably couple to the boom arm housing, and (ii) when the shuttling element is detachably coupled to the boom arm housing and the needle, rotation of the needle relative to the boom arm housing releases the shuttling element from the boom arm housing.

2. The bi-direction suture passing instrument of claim 1, wherein (i) the needle includes an engagement feature, (ii) the shuttling element includes an engagement feature, and (iii) when the shuttling element is detachably coupled to the boom arm housing, rotation of the needle relative to the shuttling element causes the engagement feature of the needle to engage the engagement feature of the shuttling element to detachably couple the needle to the shuttling element.

3. The bi-directional suture passing instrument of claim 2, wherein (i) the shuttling element includes a locking mechanism, (ii) the boom arm housing includes a locking interface, and (iii) when the shuttling element is detachably coupled to the needle, rotation of the needle relative to the boom arm housing causes the locking mechanism of the shuttling element to engage the locking interface of the boom arm housing to detachably couple the shuttling element to the boom arm housing.

4. The bi-directional suture passing instrument of claim 3, wherein engagement feature of the shuttling element and the locking mechanism of the shuttling element are oppositely oriented threads.

5. The bi-directional suture passing instrument of claim 3, wherein (i) the locking mechanism of the shuttling element and the locking interface of the boom arm housing are threads, (ii) the threads of the shuttling element extend from an external surface of the shuttling element, (iii) the threads of the boom arm housing extend from an internal surface of a bore that is defined by the boom arm housing, and (iv) the threads of the shuttling element are configured to engage the threads of the boom arm housing.

6. The bi-directional suture passing instrument of claim 3, wherein (i) the engagement feature of the needle includes a wing extending out from a body of the needle, (ii) the shuttling element includes a bore that defines an axial slot configured to receive the wing of the needle, (iii) the axial slot extends into the engagement feature of the shuttling element, (iv) the engagement feature of the shuttling element includes a radial slot, and (v) rotation of the needle causes the wing of the needle to engage the radial slot of the shuttling element to thereby detachably couple the shuttling element to the needle.

7. The bi-directional suture passing instrument of claim 6, wherein (i) the locking mechanism of the shuttling element includes a wing extending out from a body of the shuttling element, (ii) the boom arm housing includes a bore that defines an axial slot configured to receive the wing of the shuttling element, (iii) the axial slot extends into the locking interface of the boom arm housing, (iv) the locking interface of the boom arm housing includes a radial slot, and (v) rotation of the shuttling element causes the wing of the shuttling element to engage the radial slot of the boom arm housing to thereby detachably couple the shuttling element to the boom arm housing.

8. The bi-directional suture passing instrument of claim 2, wherein the engagement features of the needle and the shuttling element are threads, and the threads of the needle are configured to engage the threads of the shuttling element.

9. The bi-directional suture passing instrument of claim 8, wherein the threads of the needle extend from an external surface of the needle.

10. The bi-directional suture passing instrument of claim 9, wherein (i) the shuttling element defines a bore, (ii) the threads of the shuttling element extend from an internal surface of the bore, and (iii) the bore is configured to receive the needle.

11. The bi-directional suture passing instrument of claim 10, wherein the bore extends completely through the shuttling element, and the needle is configured to extend through the bore of the shuttling element.

12. The bi-directional suture passing instrument of claim 8, wherein the needle includes a bore, and the threads of the needle extend from an internal surface of the bore.

13. The bi-directional suture passing instrument of claim 12, wherein (i) the threads of the shuttling element extend from an external surface of the shuttling element, and (ii) the bore of the needle is configured to receive the shuttling element.

14. The bi-directional suture passing instrument of claim 1, further comprising a tip actuator coupled to the needle, wherein rotation of the tip actuator causes the needle to rotate.

15. The bi directional suture passing instrument of claim 1, further comprising an actuation member coupled to a proximal end of the needle, wherein translation of the actuation member causes the needle to translate.

16. The bi-directional suture passing instrument of claim 1, wherein either the boom arm housing or the needle include an awl tip.

17. The bi-directional suture passing instrument of claim 1, wherein the needle-like tip of the shuttling element is tapered.

18. A bi-directional suture passing instrument configured to approximate soft tissue defects, the suture passing instrument comprising:
　　a body member having a needle receiving channel;
　　a boom arm extending from a distal end of the body member, the boom arm having a boom arm housing that is spaced from the body member, wherein a tissue receiving gap is disposed between the boom arm housing and the body member;
　　a needle reciprocally translatable within the channel of the body member between an advanced position in which a distal end of the needle extends into the boom arm housing, and a retracted position in which the distal end of the needle is refracted from the boom arm housing, the needle defining a tip configured to penetrate tissue and the needle further defining an engagement feature on an external surface of the needle; and
　　a shuttling element configured to carry a suture across the tissue receiving gap, the shuttling element further configured be detachably coupled to the boom arm housing such that the suture passes through the tissue receiving gap, the shuttling element having a bore that defines an engagement feature,
　　wherein (i) the engagement features of the needle and the shuttling element engage each other to thereby detachably couple the shuttling element to the needle, when the needle is received within the bore of the shuttling element, and (ii) when the shuttling element is detachably coupled to the needle, and the needle is translated toward the advanced position, the shuttling element is configured to penetrate tissue so that the shuttling element can pass through the tissue and into the boom arm housing.

19. The bi-directional suture passing instrument of claim 18, wherein the engagement feature of the needle is a fin that extends radially outward from the external surface of the needle, and the engagement feature of the shuttling element is a groove that is configured to receive the fin.

20. The bi-directional suture passing instrument of claim 18, wherein the engagement feature of the needle is a rib extending up from the external surface of the needle, and the engagement feature of the shuttling element is a recess that is configured to receive the rib.

21. The bi-directional suture passing instrument of claim 18, wherein (i) the shuttling element further includes a locking mechanism, (ii) the boom arm housing defines a locking interface, (iii) the locking mechanism is a protrusion defining a slot, and (iv) the slot is configured to engage the locking interface of the boom arm housing.

22. The bi-directional suture passing instrument of claim 18, wherein (i) the shuttling element further includes a locking mechanism, (ii) the boom arm housing defines a locking interface, (iii) the locking mechanism is a recess defined by the shuttling element, and (iv) the recess being configured to receive the locking interface defined by the boom arm housing.

23. The bi-directional suture passing instrument of claim 18, wherein the other of the needle and the shuttling element also is configured to penetrate tissue.

24. A bi-directional suture passing instrument configured to approximate soft tissue defects, the suture passing instrument comprising:
- a body member defining a needle receiving channel;
- a boom arm extending from the body member, the boom arm having a boom arm housing that is spaced from the body member, wherein a tissue-receiving gap is disposed between the boom arm housing and the body member;
- a needle reciprocally translatable within the channel of the body member between an advanced position in which a distal end of the needle extends into the boom arm housing, and a retracted position in which the distal end of the needle is retracted from the boom arm housing;
- a shuttling element configured to detachably couple to the needle, and to the boom arm housing; and
- an actuator configured to rotate the shuttling element,
- wherein (i) when the shuttling element is detachably coupled to the needle, rotation of the shuttling element by the actuator along a first direction relative to the boom arm housing causes the shuttling element to detachably couple to the boom arm housing, and (ii) when the shuttling element is detachably coupled to the boom arm housing, rotation of the shuttling element by the actuator along a second direction that is opposite to the first direction relative to the boom arm housing causes the shuttling element to release from the boom arm housing.

25. The bi-directional suture passing instrument of claim 24, wherein the shuttling element includes a locking mechanism, and the boom arm housing defines a locking interface, the locking mechanism is configured to engage the locking interface to thereby lock the shuttling element to the boom arm housing.

26. The bi-directional suture passing instrument of claim 25, wherein the locking mechanism is a recess that is configured to receive the locking interface.

27. The bi-directional suture passing instrument of claim 24, wherein the actuator is coupled to the needle.

28. The bi-directional suture passing instrument of claim 27, wherein rotation of the needle causes the shuttling element to rotate when the needle is coupled to the shuttling element.

* * * * *